United States Patent [19]

Avery et al.

[11] Patent Number: 5,216,175
[45] Date of Patent: Jun. 1, 1993

[54] ANTIMALARIAL ANALOGS OF ARTEMISININ

[75] Inventors: Mitchell A. Avery, Palo Alto; Wesley K. M. Chong, Menlo Park; James E. Bupp, Redwood City, all of Calif.

[73] Assignee: SRI International, Menlo Park, Calif.

[21] Appl. No.: 498,252

[22] Filed: Mar. 23, 1990

[51] Int. Cl.$^5$ .......................................... C07D 491/18
[52] U.S. Cl. ................................................. 549/279
[58] Field of Search ....................................... 549/279

[56] References Cited

U.S. PATENT DOCUMENTS

| | | | |
|---|---|---|---|
| 4,350,638 | 9/1982 | Lee | 549/275 |
| 4,963,683 | 10/1990 | Avery et al. | 546/63 |
| 4,992,561 | 2/1991 | Roth et al. | 549/279 |

FOREIGN PATENT DOCUMENTS

| | | |
|---|---|---|
| 0330520 | 8/1989 | European Pat. Off. |
| 87/03330 | 12/1987 | PCT Int'l Appl. |
| 8804660 | 12/1987 | PCT Int'l Appl. |

OTHER PUBLICATIONS

Avery et al., *J. Chem. Soc., Chem. Commun.* (1990) No. 21, pp. 1487-1489.
Avery et al., *Tetrahedron Letters* (1990) 31(1):1799-1802.
Katsuhara *J. Organ. Chem.* (1967) 32(3):797-799.
Caine et al., *J. Organ. Chem.* (1984) 49:2647-2648.
Weisz et al. *J. Organ Chem* (1984) 49:2648-2650.
Oppolzer et al., *Helv. Chim. Acta* (1978) 61:2755-2762.
Stowell et al., *Org. Synthesis* (1984) 62:140-148.
Brossi et al., *J. Med. Chem.* (1988) 31:645-650.
Francotte et al., *Helv. Chim. Acta* (1987) 70:1569-1582.
Lee et al., *Tetrahedron Letters* (Mar. 1973) No. 12, pp. 965-968.
Rosch et al., *Organomet. Chem.* (1980) 195:47-53.
Trost et al., *J. Amer. Chem. Soc.* (1983) 105:4494-4496.
Rosch et al., *Angew. Chem. Int. Ed. Engl.* (1981) 20:581-582.
Desjardins et al., *Antimicrob. Agents Chemother.* (1979) 16(6):710-718.
Milhous et al., *Antimicrob. Agents Chemother.* (1979) 27(4):525-530.
Roush et al., *J. Amer. Chem. Soc.* (1984) 106:721-723.
Claus et al, *Org. Syn.* (1985) 64:150-156.
Imakura et al., *J. Chem. Soc. Chem. Commun.* (1988) pp. 372-374.
Bates et al., *J. Organ. Che.* (1989) 54:1784-1785.
Winder et al., (1978) Journal of the American Chemical Society 100:295-296.
Ireland et al., (1984) Journal of the American Chemical Society 106:3668-3670.
Klayman (1985) Science 228:1049-1055.
Klayman (1979) Chinese Medical Journal 92:811-816.
Zhou (1986) Pure and Applied Chemistry 58:817-824.
Schmid et al., (1983) Journal of the American Chemical Society 105:624-625.
Avery et al., (1987) Tetrahedron Letters 28 No. 40:4629-4632.
Clark et al., (1985) J. Org. Chem. 50:1994-1996.
Rosch et al., (1981) Angew. Chem. Int. Ed. Engl. 20:581-582.
Xing-Xiang et al., (1986) Tet. Lett. 42:819-828.

*Primary Examiner*—Marianne M. Cintins
*Assistant Examiner*—Catherine S. Kilby Scalzo
*Attorney, Agent, or Firm*—Morrison & Foerster

[57] ABSTRACT

Polyoxoheterocyclic tetracycles related to the Chinese antimalarial natural product qinghaosu (artemisinin) are disclosed. These materials have a

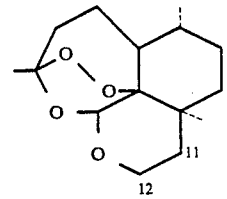

core structure with an oxygen (carbonyl or alkyl ether) at position 12 and in some cases one or two alkyl or aralkyl substituents at position 11. These materials have antimalarial properties.

13 Claims, No Drawings

ANTIMALARIAL ANALOGS OF ARTEMISININ

STATEMENT OF GOVERNMENT INTEREST

This invention was made in the performance of United States Government Contracts DAMD-17-85-C-5011, DAMD-17-88-C-8007 and DAMD-17-88-C-8048. The United States Government may have certain rights to this invention.

CROSS-REFERENCE TO RELATED APPLICATIONS

This application is related to three prior applications each made by coinventor Mitchell Avery and colleagues and each commonly owned with the present application. The prior applications are:
U.S. Ser. No. 943,555 filed Dec. 18, 1986; now abandoned;
U.S. Ser. No. 108,138 filed Oct. 13, 1987; now abandoned;
and U.S. Ser. No. 108,145 filed Oct. 13, 1987, now abandoned.

BACKGROUND OF THE INVENTION

1. Field of the Invention

This invention is in the field of organic chemistry. More particularly, it relates to methods for the synthesis of oxygen-containing heterocyclic organic compounds, materials formed by these methods, and intermediates generated in the methods. In one application, this method is used to prepare analogs of the antimalarial agent known as qinghaosu ("QHS") or artemisinin.

2. Description of Related Art

The three prior applications noted above all related generally to the same project which is dealt with herein. The present application covers recent advances over the work covered by these earlier applications.

This invention relies on ozonolysis of vinylsilanes to give rise to polyoxaheterocyclic compounds. A reference of which we are aware which involves ozonolysis of a vinylsilane is that of George Buchi et al., *Journal of the American Chemical Society*, Vol 100, 294 (1978). Another reference of interest is by R. Ireland et al., *Journal of the American Chemical Society*, Vol 106:3668, (1984), which relates to silylation.

We also call to the Examiner's attention the publications of some of this related work appearing at M. Avery et al., *Tet Lett*, Vol 28:(40), 4629, (1987).

Other art of interest to the present invention relates to the ancient antimalarial natural product known as qinghaosu. The antimalarial qinghaosu has been used in China in the form of crude plant products since at least 168 B.C. Over the last twenty years, there has been an extensive interest in this material. This has led to an elucidation of its structure as

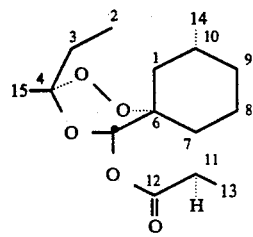

The chemical name artemisinin has been applied to the material. This name will be used in this application to identify the material.

The carbons in the artemisinin structure have been numbered as set forth above. When reference is made to a particular location in a compound of this general type, it will, whenever possible, be based on the numbering system noted in this structure. For example, the carbon atoms bridged by the peroxide bridge will always be identified as the "4" and "6" carbons, irrespective of the fact that this invention can involve materials having different bridge-length structures in which these carbons would otherwise be properly numbered.

References to artemisinin and to certain of its derivatives include the May 31, 1985 review article by Daniel L. Klayman appearing in *Science*, Vol 228, 1049 (1985); and the article appearing in the *Chinese Medial Journal*, Vol 92, No. 12, 811 (1979). Two syntheses of artemisinin have been reported in the literature by Wei-Shan Zhou, *Pure and Applied Chemistry*, Vol 58(5), 817 (1986); and by G. Shmid et al. *Journal of the American Chemical Society*, Vol 105, 624 (1983). Neither of these synthese employs ozonolysis or the unsaturated bicyclic ketones as set forth herein.

In this specification we will at times refer to the following journal articles by way of the following footnotes:

Literature Cited 1. a. J. Katsuhara. *J. Org. Chem.*, 32, 797 (1967). b. D. Caine, K. Procter, and R. Cassell. *J. Org. Chem.*, 49, 2647 (1984).
2. W. Oppolzer and M. Petrzilka. *Helv. Chim. Acta*, 61, 2755 (1978).
3. J. Stowell, D. Keith, and B. King. *Org. Synthesis*, 62, 140 (1984).
4. Brossi, A., Venugopalan, B. Dominguez Gerpe, L., Yeh, H. J. C., Flippin-Anderson, J. L., Buchs, P., Luo, X. D., Milhous, W., and Peters, W. J. Med. Chem. 31, 645 (1988).
5. Francotte, E., and Lohmann, D. Helv. Chim. Acta 70, 1569 (1987).
6. Lee, R. A., McAndrews, C., Patel, K. M., and Reusch, W. Tetrahedron Lett. 965 (1973).
7. Primary reference: L. Rosch and G. Altman. *J. Organomet. Chem.*, 195, 47 (1980). It should be noted that this procedure has failed to work in our hands, as well as others: see B. Trost, J. Yoshida, and M. Lautens. *J. Amer. Chem. Soc.*, 105, 4494 (1983). However, a procedure which works is provided in the experimental. The reagent can be titrated as described or by reaction with peperonal: L. Rosch, G. Altman, and W. Otto. *Angew. Chem. Int. Ed. Engl.*, 20 581 (1981).
8. Desjardins, R. E., Canfield, C. J., Haynes, D. E., and Chulay, J. D. Antimicrob. Agents Chemother, 16, 710–718 (1979).
9. Milhous, W. K., Weatherly, N. F., Bowdre, J. H., and Desjardins, R. E. Antimicrob. Agents Chemother. 27, 525–530 (1979).
10. W. Roush and W. Walts. *J. Amer. Chem. Soc.*, 106, 721 (1984).
11. Claus, R. E., and Schreiber, S. L. Org. Syn. 64, 150 (1985).
12. U.S. patent application Nos.: 1. 10814 (10/13/87); 2. 108138 (10/13/87); 3. 943555 (12/18/86).
13. Y. Imakura, T. Yokoi, T. Yamagishi, J. Koyama, H. Hu, D. R. McPhail, A. T. McPhail, and K.-H. Lee. *J. Chem. Soc. Chem. Commun.* 372 (1988).

14. T. F. Bates, and R. D. Thomas. *J. Org. Chem.*, 54, 1784 (1989).

The interest in antimalarial materials which are improved in terms of activity, strain selectivity and/or ease of production has prompted this continued research effort. The present invention is the result of this effort.

STATEMENT OF THE INVENTION

In one aspect, the present invention provides yet additional antimalarial analogs of artemisinin. These analogs are listed in Table 1. In Table 1, the new analogs are assigned numeric identification which are then used in the later description of the analogs' preparation and biological properties.

TABLE 1

| Analog | Identification Code for Synthesis | Identification Code for Biological Results |
|---|---|---|
| [structure] wherein R is an alkyl of 1 to 10 carbons, or an aralkyl of 7 to 9 atoms. | 14 R = CH₃ | 2800 |
| [structure] | 15 | 4584 |
| [structure] wherein R is a lower (1-4 carbon) alkyl such as methyl, ethyl or propyl; an aralkyl of 7 to 9 carbons; a 1-4 carbon carboxylic acid; a 1-4 carbon alkyl ester of a 1-4 carbon carboxylic acid; or a dialkyl (1-4 carbon each) amino 1-4 carbon alkyl. | 16<br>16a R = CH₃<br>16b R = CH₂—CH₂—CH₃<br>16c R = CH₂—Ph<br>16d R = CH₂—CO₂—tBu<br>16e R = CH₂—CO₂H<br>16f R = CH₂—CH₂—N—(CH₃)₂ | 4585 |
| [structure] | 17 | 4586 |

TABLE 1-continued

| Analog | Identification Code for Synthesis | Identification Code for Biological Results |
|---|---|---|
| (structure with CO2H) | 18 | 4595 |
| (structure with O-O-tBu) | 19 | 4588 |
| (structure with OEt) | 20 | 4598 |
| (structure) | 21 | — |
| (structure with R) | 89 R = n propyl<br>108 R = n hexyl<br>109 R = n tetradecyl<br>110 R = i propyl<br>111 R = CH$_2$CH$_2$CH$_2$—Ph<br>112 R = i amyl<br>120 R = CH$_2$Ph | 4599 | wherein R is a 1-20 carbon linear or branched alkyl or a 7 to 12 carbon aralkyl.

TABLE 1-continued

| Analog | Identification Code for Synthesis | Identification Code for Biological Results |
|---|---|---|
| [structure] wherein R is as set forth immediately above. | 90 R = n-propyl | 4600 |
| [structure] | 22 | 4580 |
| [structure] | 23 | 4589 |
| [structure] | 24 | 4582 |
| [structure] | 25 | 4593 |
| [structure] | 26 | 4590 |

TABLE 1-continued

| Analog | Identification Code for Synthesis | Identification Code for Biological Results |
|---|---|---|
| | 27 | |
| | 28 | |
| | 29 | 4591 |
| | 30 | 4592 |
| | 31 | 4594 |
| | 32 | 4596 |
| | 33 | 4597 |

TABLE 1-continued

| Analog | Identification Code for Synthesis | Identification Code for Biological Results |
|---|---|---|
| (structure) | 52 | |
| (structure) wherein R is hydrogen lower alkyl of 1 to 4 carbon, especially methyl. | 116 | |
| (structure) wherein R is a 1 to 4 carbon alkyl, a 7 to 9 carbon aralkyl, or a 7 to 9 carbon aralkyloxy. | 93 R = CH₃<br>94 R = CH₂—CH₃<br>96 R = O—CH₂—Ph | |
| (structure) | 97 | |
| (structure) | 118 | |

In an additional aspect, the present invention provides an improved simplified synthetic route to artemisinin and its analogs. The improved process, which is shown schematically in Scheme I, has as key steps:

a) reacting

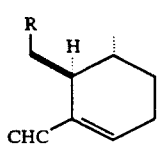

8

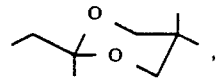

wherein R is R = with tris (trialkylsilyl) aluminum etherate followed by acetic anhydride to yield

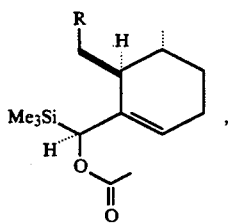

b) treating 9 with lithium dialkylamine to yield

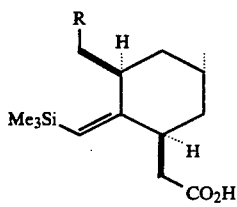

c) subjecting 10 to dianion alkylation with alkyl iodide of the formula R*I, wherein R* is a lower alkyl of from 1 to 4 carbons, optionally including a 14C atom to yield

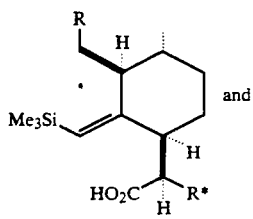

d) subjecting 11 to ozonolysis followed by acidification to yield

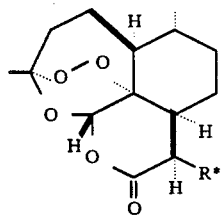

In an additional aspect, this invention provides antimalarial compositions based on the new compounds it enables.

DETAILED DESCRIPTION OF THE INVENTION

1. Total Synthesis of (+)-Artemisinin

Our previous description of the total synthesis of (+)-Artemisinin 12, found in U.S. patent application Ser. No. 06/943,555, and in *Tetrahedron Letters* 28(40): 4629 (1987), has been improved from 18 steps to 11 steps as shown in Scheme I. Commercially available R(+)-pulegone 1 was converted to pulegone epoxide 2 and then to the sulfide 3 as described by others (J. Katsuhara. *J. Org. Chem.*, 32, 797 (1967) and D. Caine, K. Procter, and R. Cassell. *J. Org. Chem.*, 49, 2647 (1984)). Oxidation of the sulfide 3 to the sulfone 4 was accomplished with peracid in $CH_2Cl_2$, as previously reported (W. Oppolzer and M. Petrizilka. *Helv. Chim. Acta.* 61, 2755 (1978)).

The dianon derived from 4 was alkylated with the bromide 13 (J. Stowell, D. Keith, and B. King. *Org. Synthesis*, 62, 140 (1984)) and the crude product desulfurized with Al(Hg) amalgam to afford the ketone 6, in 37–50% combined yield (from 4), as a 9:1 isomeric mixture (2β:2α respectively).

Formation of the hydrazone 7 was accomplished, without epimerization at C-2, by neat reaction of 6 with tosylhydrazide. Bamford-Stevens rearrangement of 7 gave a vinyl anion which on quenching with DMF afforded the aldehyde 8 (70%).

The key improvement to the total synthesis as presented herein is the diasteroselective silylanion addition to 8 with tris(trimethylsily)aluminum.etherate, which gives, on capture by acetic anhydride, the silyl-acetate 9 in excellent yield (88%). Ireland-Claisen ester-enolate rearrangement of 9, following deprotonation by lithium diethylamide (LDEA), provides the key acid 10 in good yield (56%).

The other present improvements to the process are the dianion alkylation of 10 (leading directly to 11) and the subsequent one-pot ozonolysis/acidification/cyclization sequence which provides natural product (12) directly from 11.

Scheme I.
Optimized Total Synthesis of (+)-Artemisinin

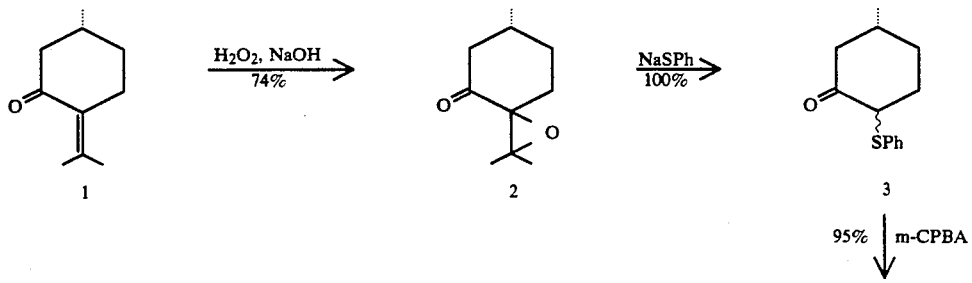

Scheme I.
Optimized Total Synthesis of (+)-Artemisinin

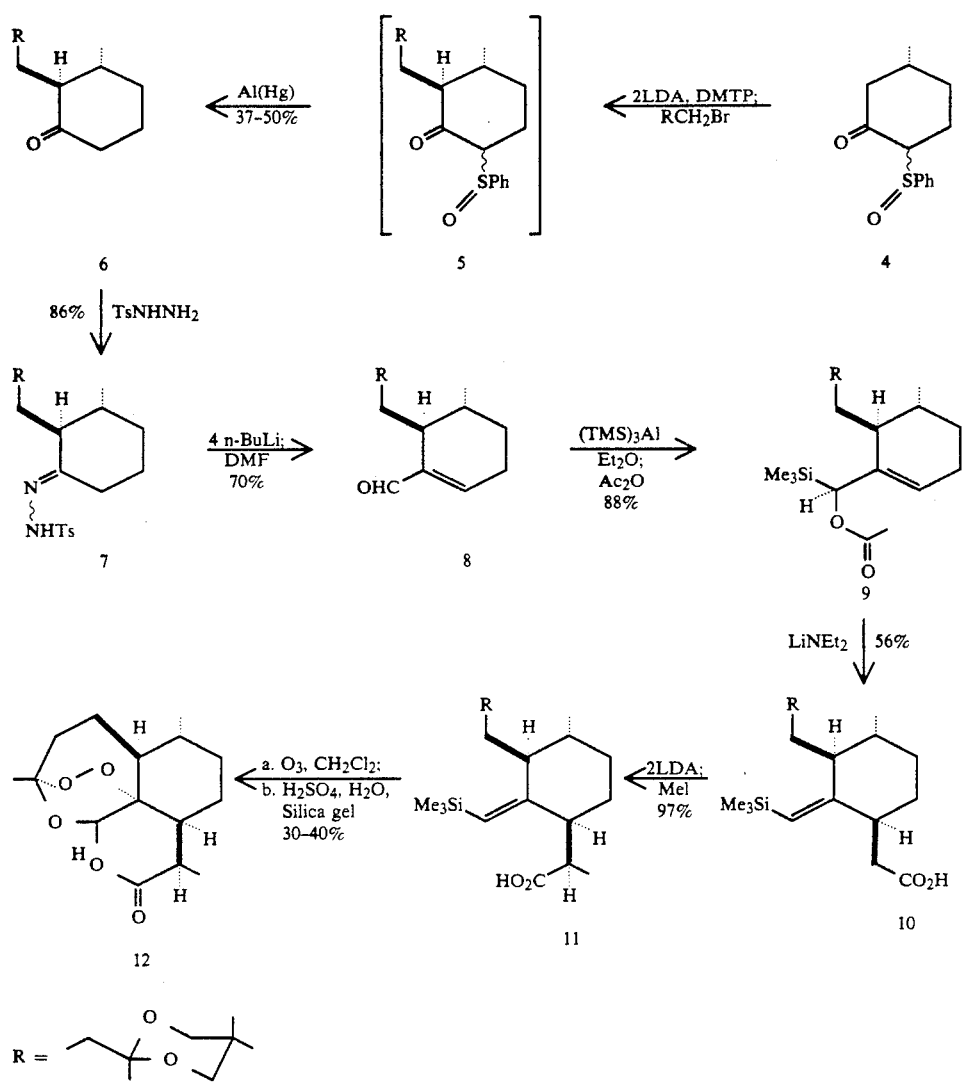

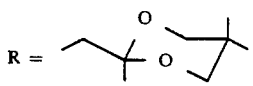

Thus, on treatment of 10 with 2 equivalents of LDA and alkylation with MeI, the diastereomerically pure acid 11 is produced in high yield. Alternately, treatment of 9 with excess LDEA followed by $CH_3I$ provided the ozonolysis precursor 11 directly in good yield. Ozonolysis of 11, followed by in situ deketalization/cyclization with acid-impregnated silica gel, provided in a one-pot procedure the natural product (+)-artemisinin (12, 35%) along with the by-product deoxyartemisinin (6%).

2. Radiolabel Synthesis

In order to conveniently introduce $^{14}C$ into a metabolically stable position of the natural product 12, we began with the acid 10 as illustrated in Scheme I.

By the process already outlined, alkylation of 10 with $^{14}CH_3I$ gave $^{14}C$-11. An ozonolysis/cyclization as before, $^{14}C$-12, was produced as shown below, together with $^{14}C$-deoxy-artemisinin 12a. The labeled natural product 9-$^{14}C$-(+)-artemisinin ($^{14}C$-12) had 7.26 mCi/mmol and was 98.3% radiochemically pure (>99.9% chemical purity).

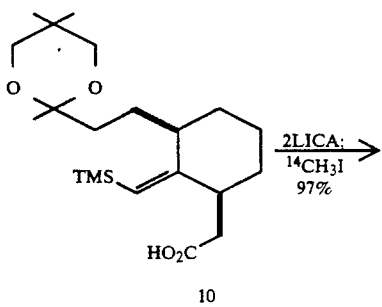

17

-continued

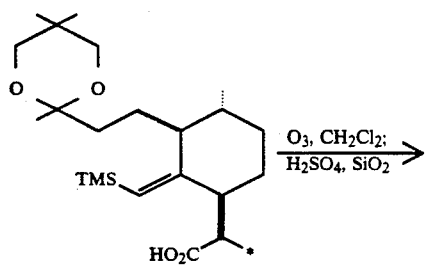

$^{14}C$-11

$\xrightarrow{O_3, CH_2Cl_2;\ H_2SO_4, SiO_2}$

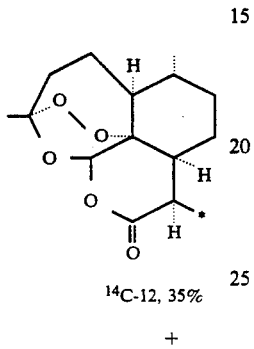

$^{14}C$-12, 35%

+

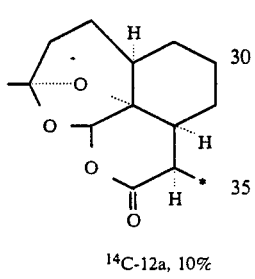

$^{14}C$-12a, 10%

3. Analog Synthesis

We synthesized a number of analogs that may be divided into four major groups: (1) optically active, substituted QHS and dihydro-QHS (arteether, 13) analogs that were produced via branches from our total synthesis; (2) racemic analogs derived from bicyclic synthetic intermediates, 6,9-desmethyl QHS (21) and truncated system 22; (3) seco-analogs of racemic nature with lactone substituents (24–28) and optically active substituted cyclohexanes Artemisinin Analogs

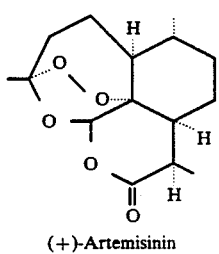

(+)-Artemisinin (12)

18

-continued

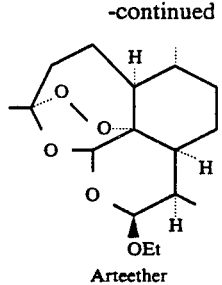

Arteether (13)

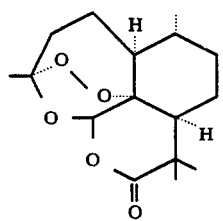

14

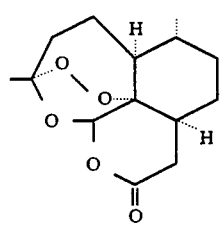

15

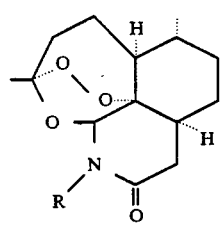

16 (a–f)

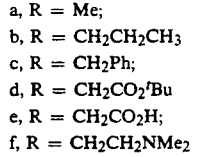

a, R = Me;
b, R = $CH_2CH_2CH_3$
c, R = $CH_2Ph$;
d, R = $CH_2CO_2{}^tBu$
e, R = $CH_2CO_2H$;
f, R = $CH_2CH_2NMe_2$

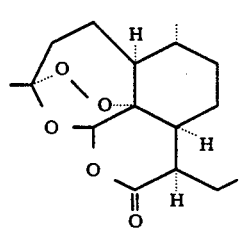

(17)

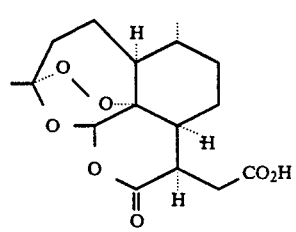

(18)

-continued
(19)
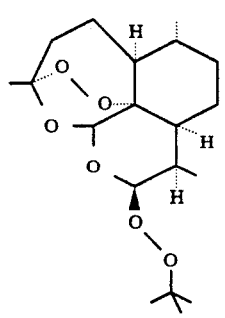
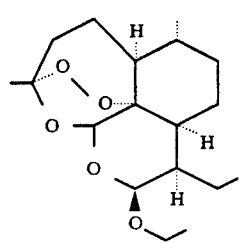
(20)
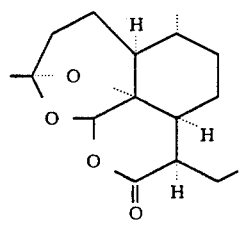
(21)
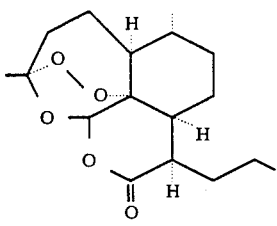
(89)
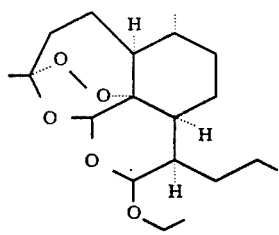
(90)
Analogs via Bicyclics
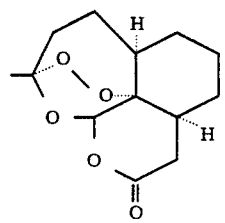
-continued
23
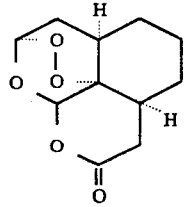
Seco Analogs
24
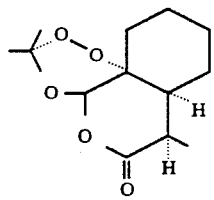
25
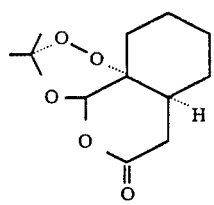
26
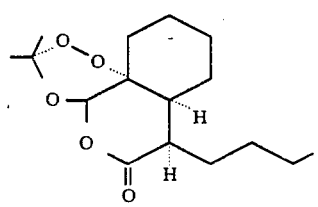
27
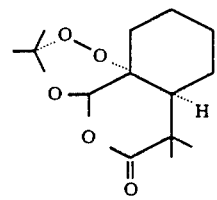
28
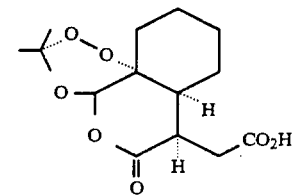
29
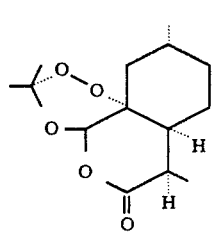

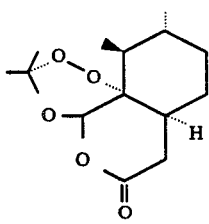

30

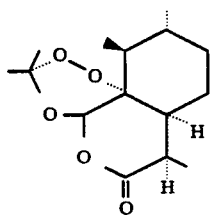

31

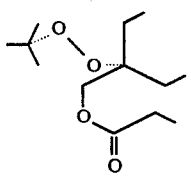

Acyclic Analogs

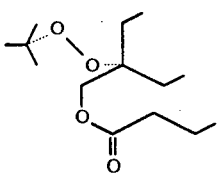

32

33

(29-31); and (4) highly abbreviated and flexible racemic QHS analogs. All of these analogs comprised our first extensive sample group for a structure-activity relationship (SAR) study. (Biological results are set forth in the Examples, below).

Substituted QHS and Dihydro-QHS

The nor-analog 15, aza-analog 16, and homologue 17 were first prepared via appropriate manipulation (see Scheme II) of the intermediate ester 34, available from our total synthetic manifold.

Subsequent to our original preparation of analogs 15, 16 and 17, the problematic alkylation of ester 34 was circumvented by the efficient and stereoselective monoalkylation of the corresponding dianion 10a of acid 10. For example, the LDA-generated dianion of 10 was monomethylated to the correct C9 epimer 40, as shown by correlation to previously obtained material. The basis of this stereoselectivity is unknown, so we are currently examining possible responsible conformations along the reaction coordinate with the aid of computer modelling. The total synthesis of QHS has thus been formally streamlined because there no longer is a need to prepare, alkylate, and cleave the ester 34.

With this new methodology available, the analog 18 was reprepared at a larger scale via alkylation of the LDA-generated dianion of 10. In this case t-butyl bromoacetate was used to provide initially acid-ester 41, which was Scheme II

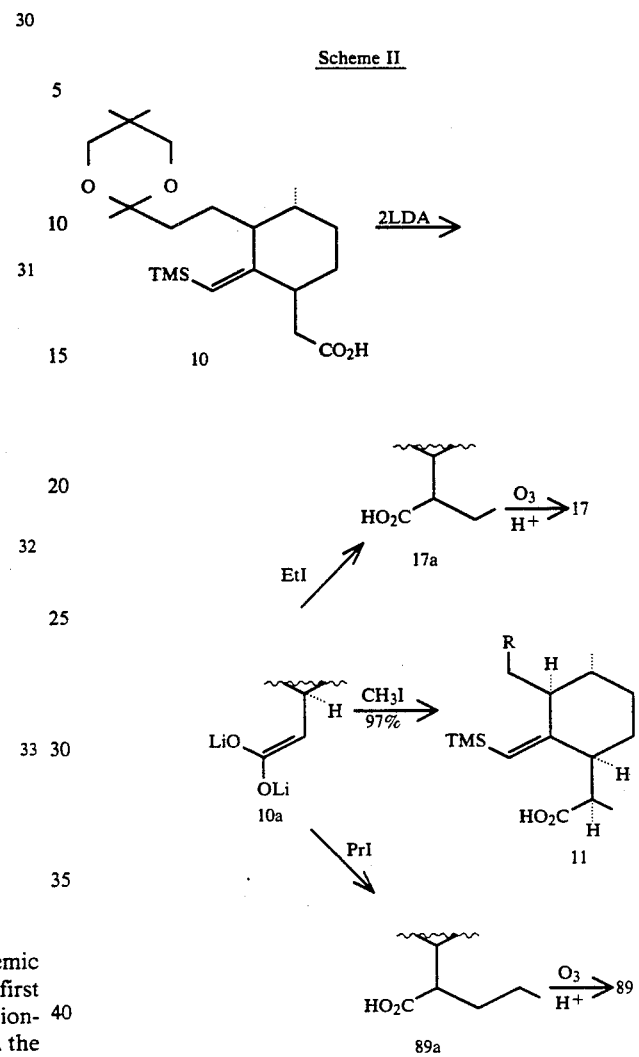

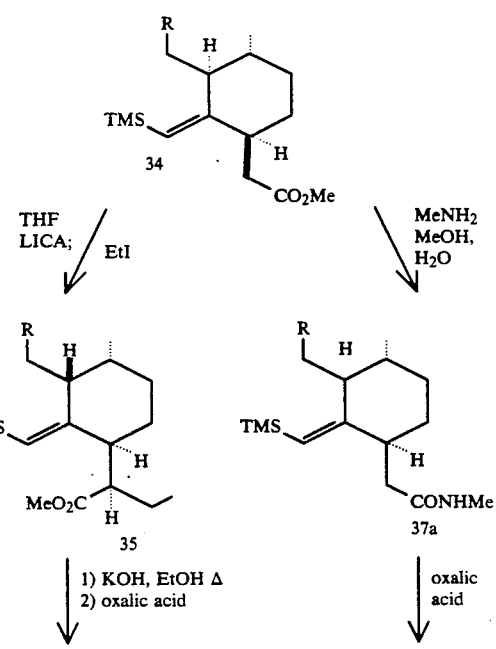

-continued
Scheme II

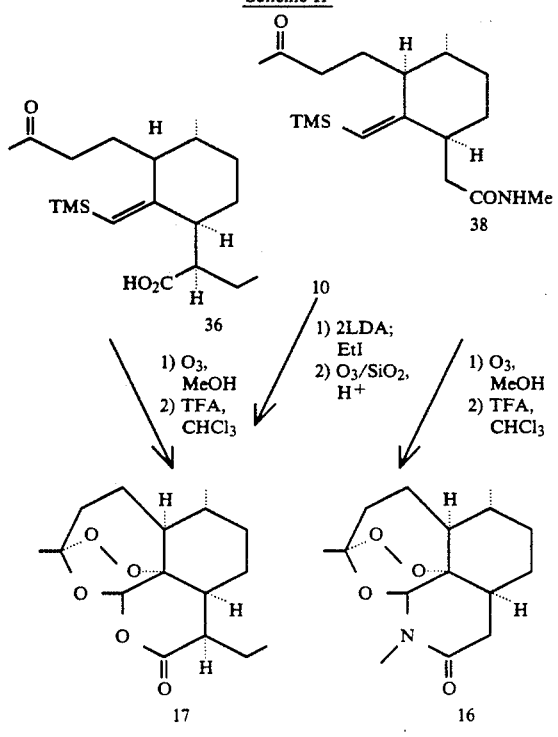

submitted to another improvement in our procedure, i.e., effecting successive ozone addition and acidification in a single reaction vessel to give directly the proper tetracyclic peroxide system 42, in turn subsequently treated with trifluoroacetic acid to cleave the t-butyl ester to the free acetic acid appendage of target 6 in 20% overall yield from 41.

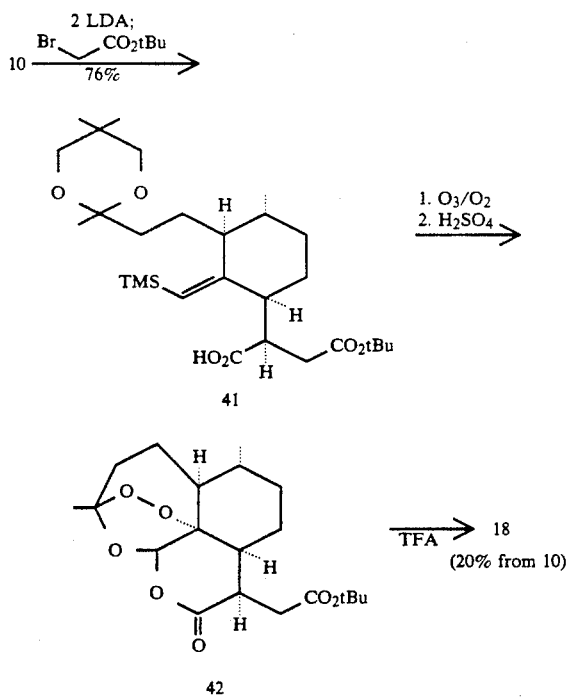

In a similar manner the homologues 17 and 89 were made on a preparative scale via alkylation of 10 to give the ethyl (17a) and propyl (89a) acids. Subsequent exposure of the resultant alkylation products (e.g., 17a, 89a) to ozone, followed by acidification gave the targets 17/89.

This dianion alkylation approach has been found to be nearly general. For example, the longer n-alkyl and substituted alkyl bromides were good alkylation substrates for dianion 10a and gave the acids 102 through 107/119:

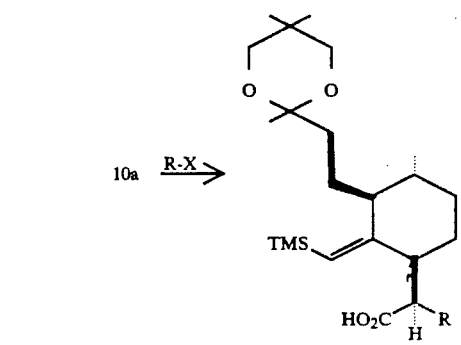

102, R = hexyl, 82%
103, R = tetradecyl, 66%
104, R = (CH$_2$)$_5$CH$_2$OSiMe$_2$$^t$Bu, 27%
105, R = (CH$_3$)$_2$CH, 54%
106, R = CH$_2$CH$_2$CH$_2$Ph, 55%
107, R = CH$_2$CH$_2$CH(CH$_3$)$_2$, 89%
119, R = CH$_2$Ph As expected, these acids underwent successive, one-pot ozonolysis and acid-catalyzed cyclization to afford the 9-substituted analogs of artemisinin 108–112/120:

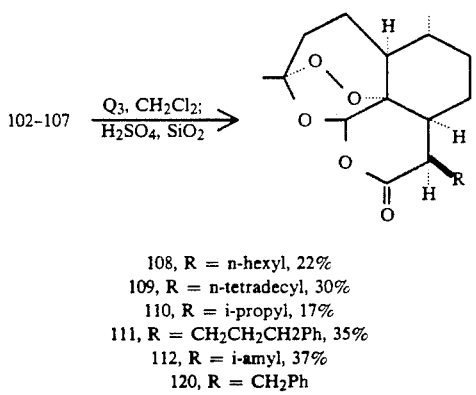

108, R = n-hexyl, 22%
109, R = n-tetradecyl, 30%
110, R = i-propyl, 17%
111, R = CH$_2$CH$_2$CH$_2$Ph, 35%
112, R = i-amyl, 37%
120, R = CH$_2$Ph As shown in Scheme XI, (+)-acid 10 was obtained from the total synthesis route. A cold solution of the corresponding triethylammonium carboxylate was treated with ethyl chloroformate. The resultant mixed anhydride reacted with various primary amines to give the amide 11, which proved satisfactory substrates for reaction with ozone and subsequent acidification to afford the lactam analogs 16. In particular examples, further transformations were warranted for deprotection or derivatization: the N-(2-acetic acid) analog 16e was provided upon hydrolysis of ester 16d with trifluoroacetic acid in dichloromethane. The hydrochloride monohydrate salt 16g proved a little more convenient to handle than amine 16f.

Scheme XI

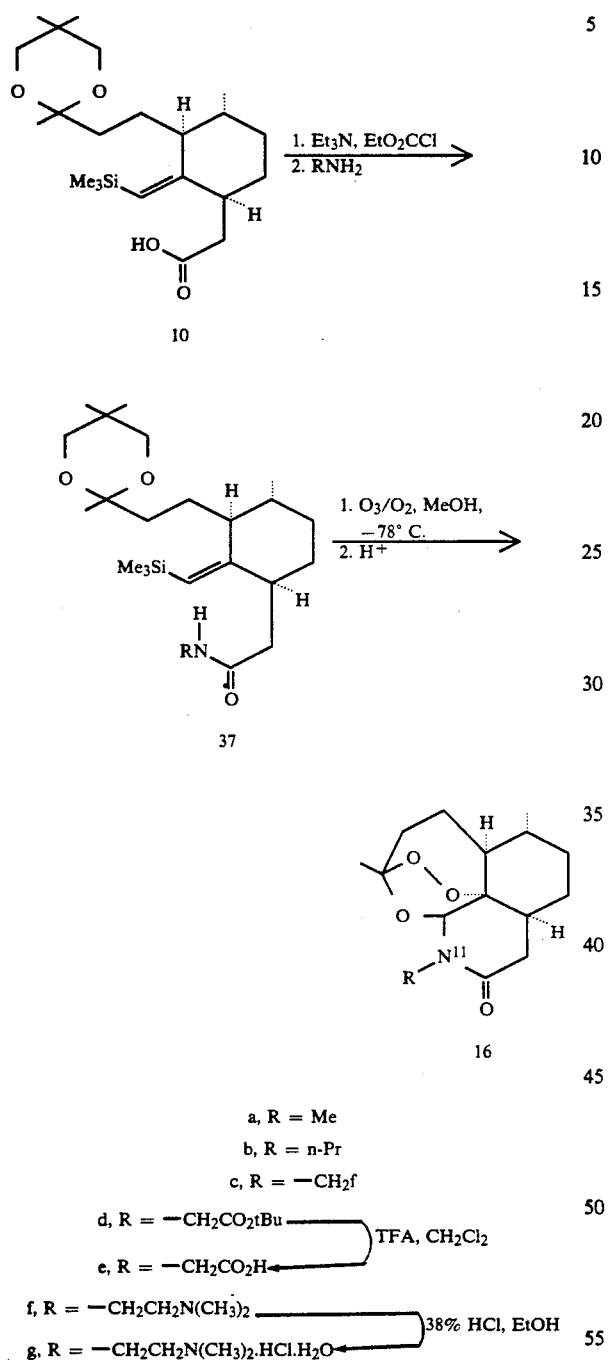

a, R = Me
b, R = n-Pr
c, R = —CH₂f
d, R = —CH₂CO₂tBu ⎫
e, R = —CH₂CO₂H ⎬ TFA, CH₂Cl₂
f, R = —CH₂CH₂N(CH₃)₂ ⎫
g, R = —CH₂CH₂N(CH₃)₂·HCl·H₂O ⎬ 38% HCl, EtOH

Other workers (Brossi, a., Venugopalan, B. Dominguez Gerpe, L., Yeh, H. J. C., Flippin-Anderson, J. L., Buchs, P., Luo, X. D., Milhous, W., and Peters, W., J. Med. Chem. 31: 645 (1988)) have described the higher potency of arteether (13) relative to artemisinin (12). This had forecast the selective reduction of the lactone of our novel analogs as a routine method with the likely potential to increase antimalarial activity. In the past year we have started to examine a few of these lactol derivatives, as discussed below.

Accordingly, reduction of QHS (12) with NaBH₄ by a known method afforded dihydroqinghaosu (DHQHS) 43. Treatment of 43 under anhydrous conditions with acid and t-butylhydroperoxide gave the desired perether 19 in 61% yield. The C-10 ether was shown to be of the β configuration by NMR ($J_{9,10}$=4.5 Hz). The perether 19 was tested for antimalarial activity in vitro.

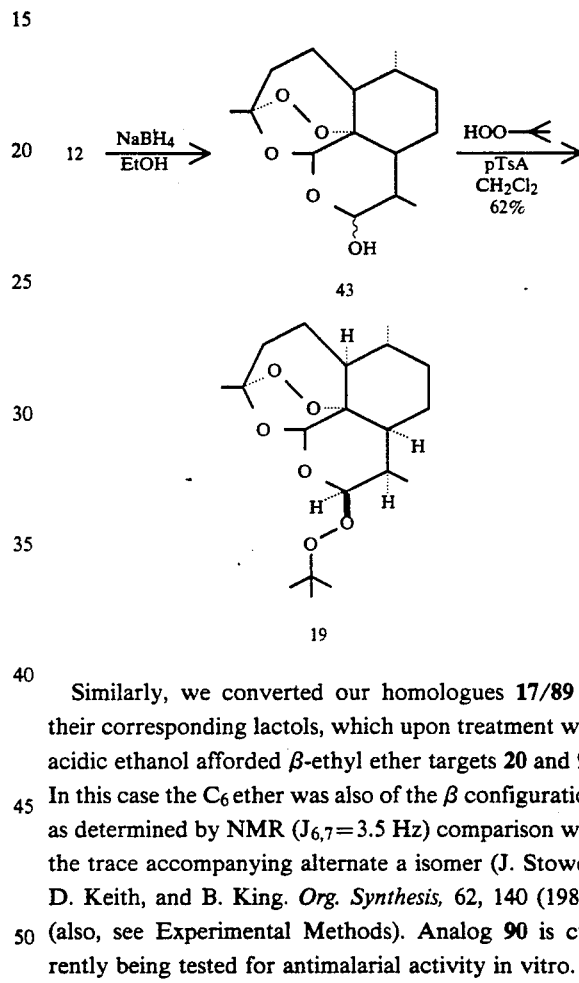

Similarly, we converted our homologues 17/89 to their corresponding lactols, which upon treatment with acidic ethanol afforded β-ethyl ether targets 20 and 90. In this case the C₆ ether was also of the β configuration, as determined by NMR ($J_{6,7}$=3.5 Hz) comparison with the trace accompanying alternate α isomer (J. Stowell, D. Keith, and B. King. Org. Synthesis, 62, 140 (1984)) (also, see Experimental Methods). Analog 90 is currently being tested for antimalarial activity in vitro.

In addition to the per-ether analogs of dihydro-QHS, carbonate analogs have been prepared by acylation of dihydro-QHS (43). While numerous analogs derived from 43 have appeared in the literature, linkage of 43 to cell membrane components has not been disclosed. Thus, we have synthesized the analogs 100 and 101 where 43 is linked to either cholesterol (for 100) or diglycerides such as dipalmitin (for 101). It is expected that much of the damaging action of this class of drugs occurs in the parasite cell membrane, thus 100/101 would be actively taken to and/or incorporated into the site of action. Also, plasma half-life/metabolism may be extended by this approach (via depot into fatty tissue).

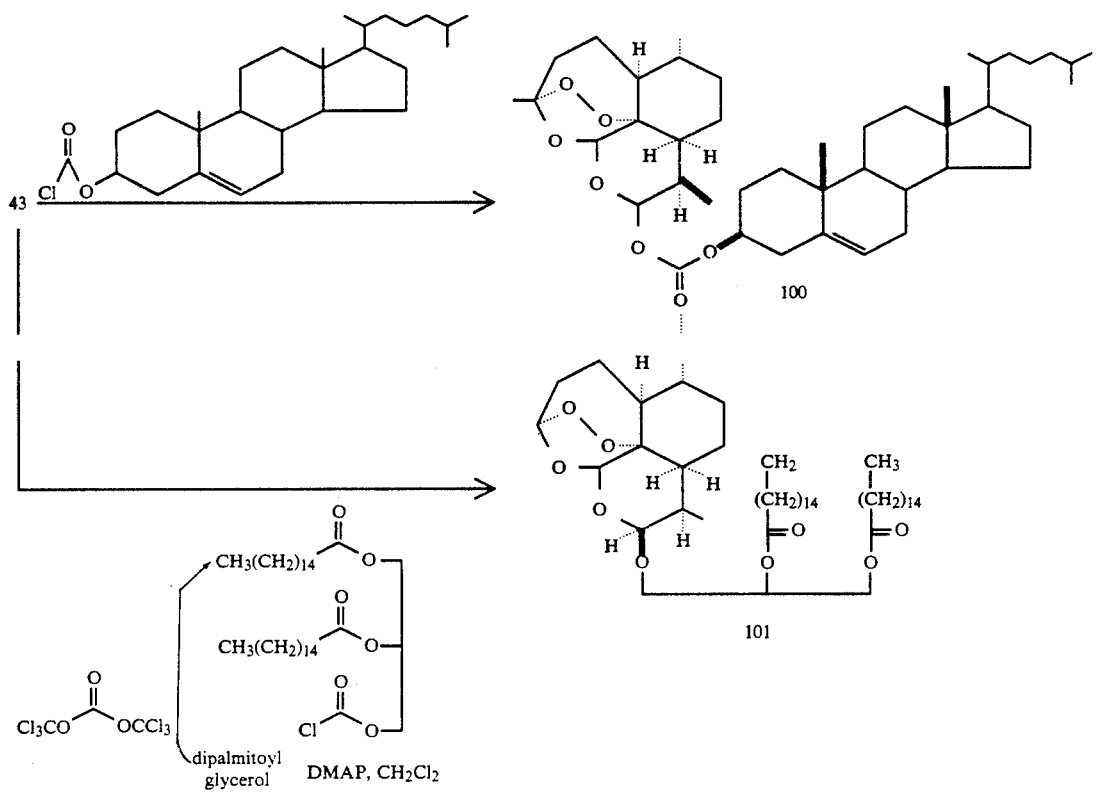

We also found that QHS (12) could be deprotonated and then alkylated with CH$_3$I to afford the gem-dimethyl analog 14. It is presumed that other alkylating agents can be employed in this reaction to give general formulas 91:

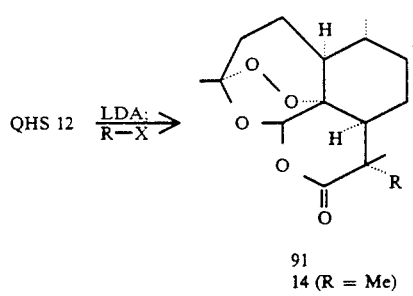

Our interest in these structures (91/14) is that they may have enhanced oral activity (relative to 12). (+)-9-Methylartemisinin 14 is currently undergoing in vitro antimalarial testing and will then be tested orally in mice.

3a. Analogs of Artemisinin Derived from Bicyclo[4.3.1]-decenones

We had previously submitted for biological evaluation the analog (±)-6,9-desmethylartemisinin 22, which was prepared according to the synthesis route in Scheme III. This synthesis is described in U.S. patent application Ser. No. 07/108,145. We have published the preparation of analog 22 with full experimental details in *J. Org. Chem.* 54, 1792 (1989). Approximately 200 mg of 22 was made. Unfortunately, initial effort to resolve 22 into its two optical isomers with cellulose triacetate (Francotte, E., and Lohmann, D. *Helv. Chim. Acta* 70, 1569 (1987)) have failed.

Scheme III

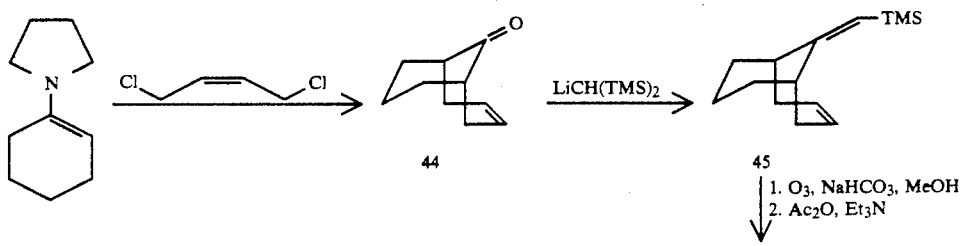

-continued
Scheme III

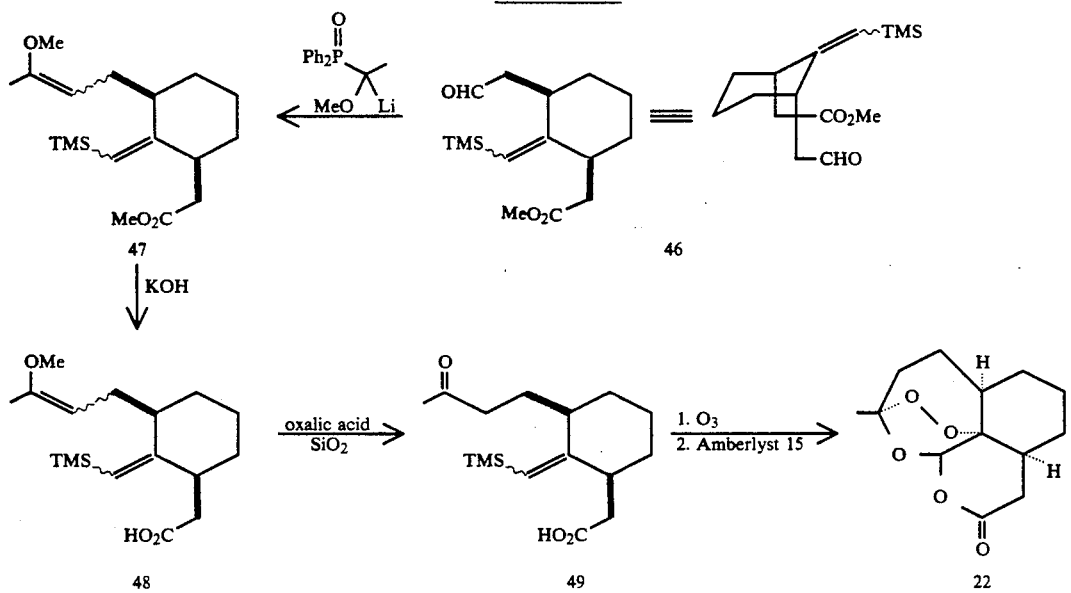

In the preparation of 22, a Wittig-type reaction of 45 to 46 served to incorporate carbons needed to build the tetracyclic system of artemisinin. As seen in Scheme IV, we took a portion of diene 45 and bypassed the introduction of any other carbons. After sequential deprotection of 50 via 51 and 52, closure to a new, more compact tetracyclic peroxide 42 was accomplished with our existing methodology.

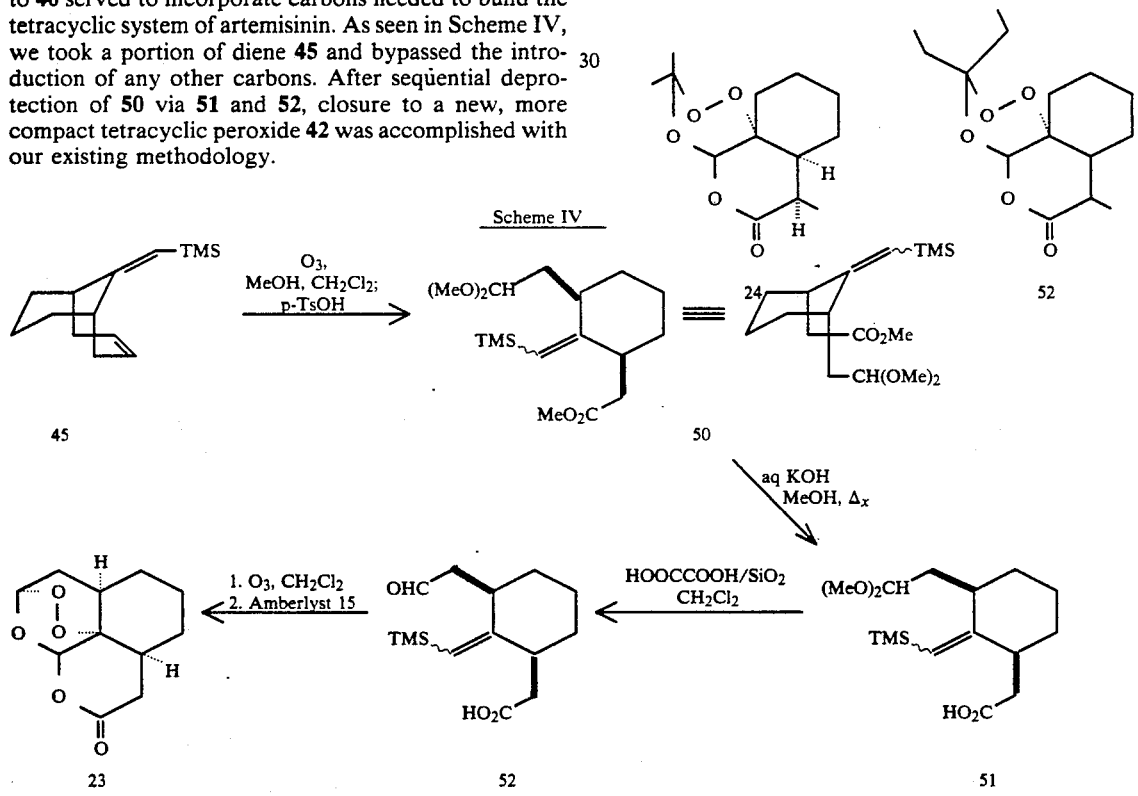

Scheme IV

3b. Tricyclic (seco) Analogs of Artemisinin i. Ring B Seco Analogs

In the past we have synthesized tricyclic analogs of QHS (12), such as 24, from simple materials.

The fact that 24 has about 20% of the activity of 12 and is somewhat easier to synthesize than 12 has stimulated further efforts in this area.

SAR data indicated that additional alkyl groups in the vicinity of the peroxy group (24 versus. 52) reduced activity substantially. Because we wished for similar reasons to examine the lactone ring of 24, we prepared the butyl derivative 26 as shown in Scheme V.

57 in 93% yield. On ozonolysis, 52 was transformed to the hydroperoxide 58 (55%) as expected. Finally 58 was treated in acetone with TFA to give the desired analog 26. The butyl derivative 26 was evaluated for biological activity.

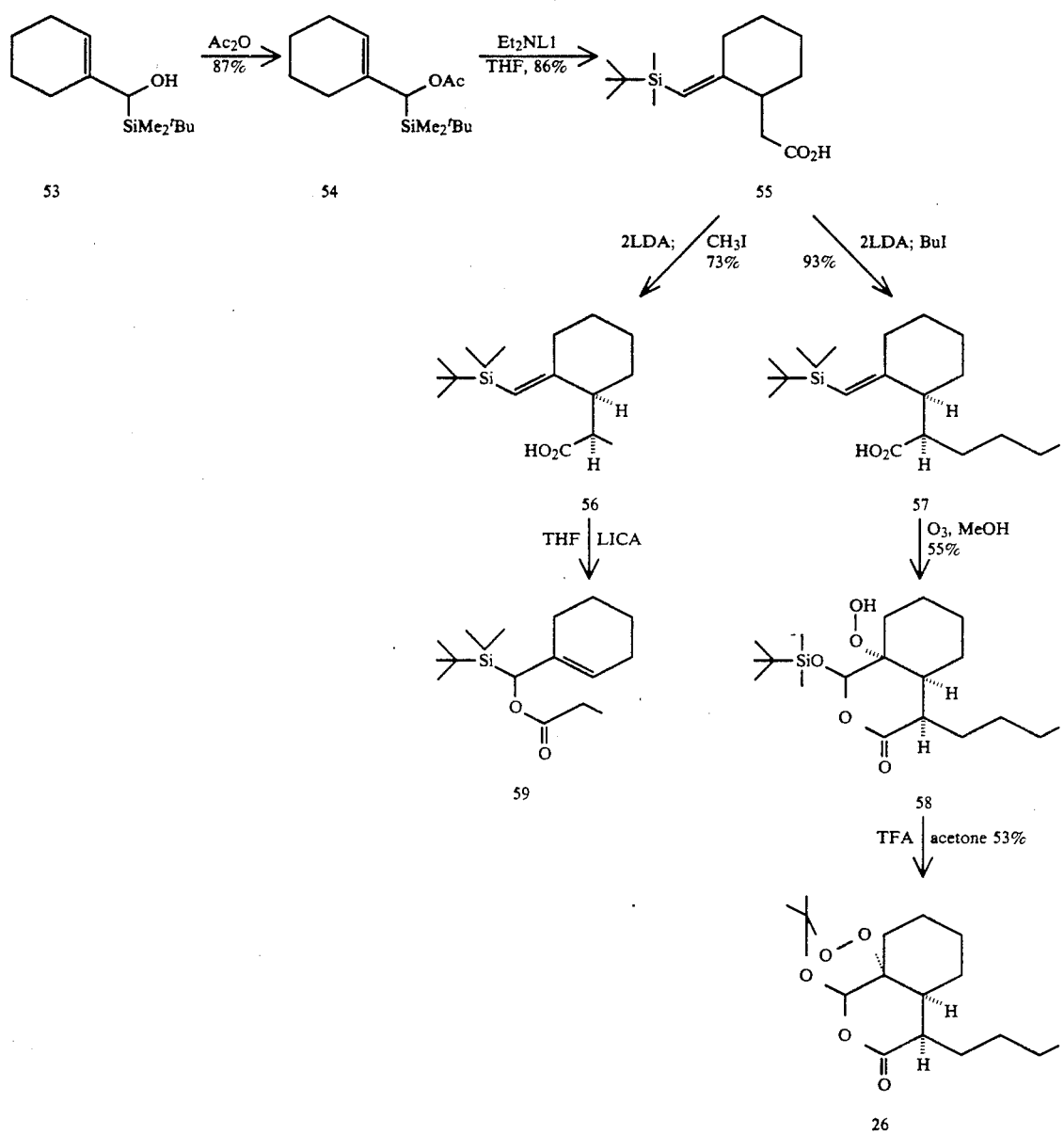

Acetylation of the alcohol 53 gave the ester 54 in 87% yield after distillation. Claisen rearrangement of 54 using lithium diethylamide as base avoided the usual competing self-condensation side reactions seen with other bases and gave the acid 55 in excellent yield (86%). We did not know whether alkylation of the dianion derived from 26 would proceed diastereoselectively, as had occurred in the total synthesis 10→40. Thus, the dianion of 55 was alkylated with methyl iodide and proceeded, quite unexpectedly, with complete diastereo selection to give 56 in 73% yield. The structure 56 was correlated with the known propionate Claisen product, 59→56. We were therefore confident that the alkylation of 55 with butyl iodide would give the desired diastereomer, and so we prepared the acid Other racemic analogs 25, 27, and 28 were prepared as shown in Scheme VI to examine the effects of systematic variation within the lactone ring in some readily made analogs. The alcohol 53 served as the starting material for 25, 27 and 28 in synthetic sequences analogous to those described previously herein. For example, the corresponding acetate 54 was made in quantitative yield and underwent Ireland-Claisen rearrangement to acetic acid 55 in 86% yield. The vinylsilane acid 55 was carefully treated with ozone/oxygen to provide the hydroperoxy lactone 60 in 17% yield; subsequent treatment of 60 in acetone with trifluoroacetic acid gave the desired tricyclic analog 25 in 38% yield.

Access to analogs with a higher degree of substitution was easily obtained: From either the proprionate ester 61 or acetic acid 55, we previously made the proprionic-acid-appendaged 62, which was in turn alkylated to the gem-dimethyl acid 35 in 76% yield (93% based on recycled starting material). The vinylsilane of 63 underwent addition of ozone to eventually afford hydroperoxide 64, and final ring closure was accomplished with trifluoroacetic acid and acetone to afford gem-dimethyl analog 27 in 19% overall yield from 63.

Using an analogous synthetic method, upon esterification of alcohol 29 the hemisuccinate 55 was obtained in 28% yield (64% based on recyclable starting material). The unprecedented Ireland-Claisen rearrangement of a hemisuccinate was effected by excess lithium diethylamide (LDEA) in THF. Upon warming overnight from −78° C., the diacid 66 was produced in 76% yield. The geometry depicted for 66 was expected by analogy to give 62 and was confirmed by NOE difference experiments. Treatment of diacid 66 with ozone led to production of a very labile hydroperoxide 62, which was treated immediately with acid and acetone to give carboxyl analog 28 in 6% overall unoptimized yield from 66.

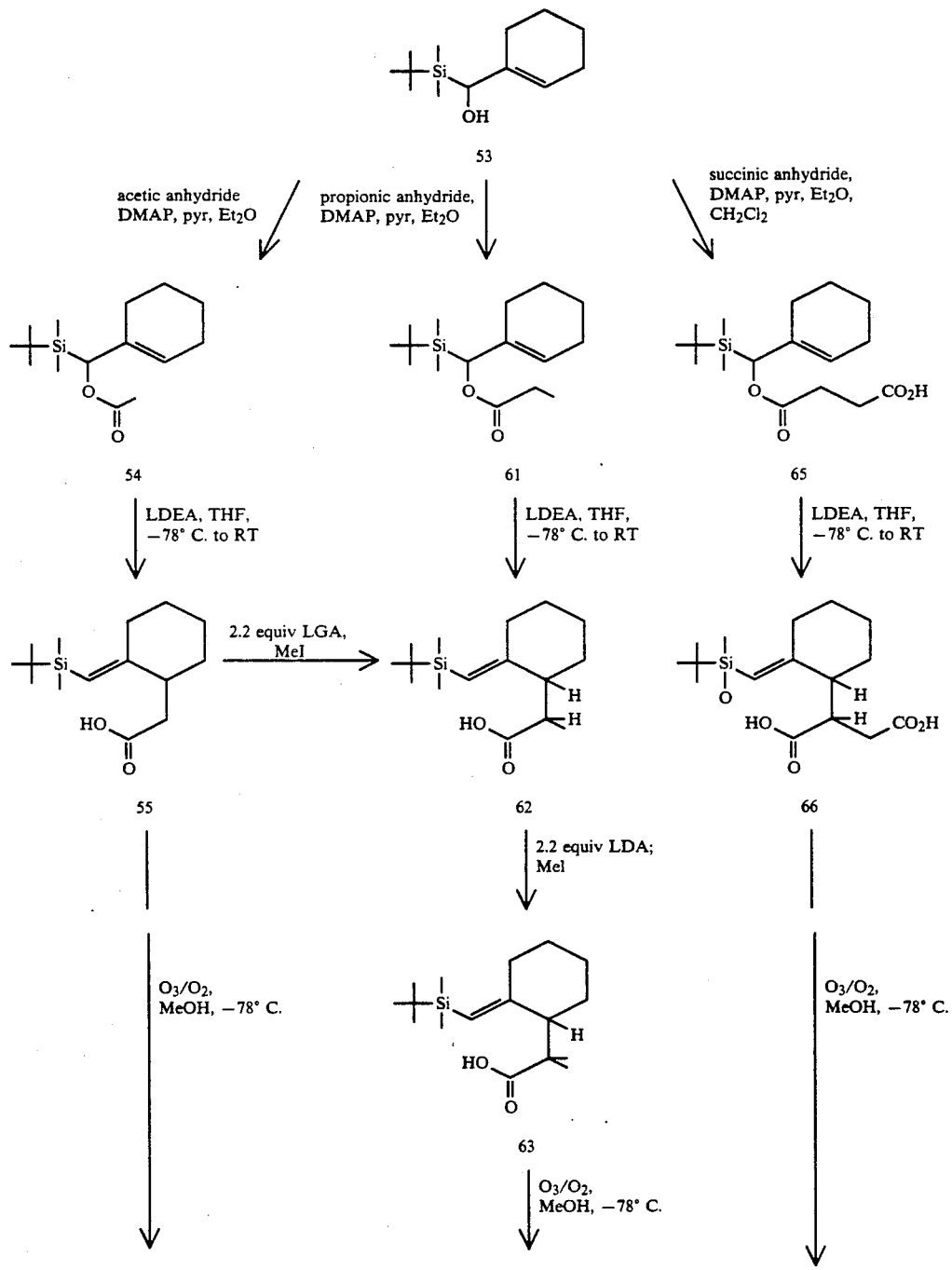

Scheme VI

-continued
Scheme VI

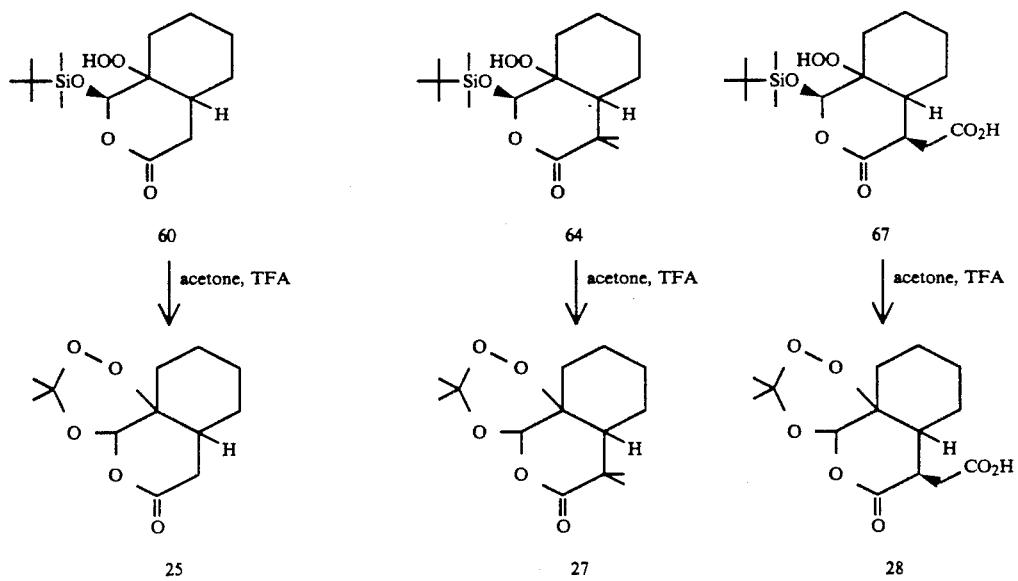

With regard to the class of tricyclic analogs of 12, a major focus of recent efforts has been the synthesis of an optically active tricyclic analog, as previous compounds were all racemates. Accordingly, we designed a synthesis with a homochiral starting material possessing the correct absolute configuration. Thus, analog 29i was synthesized from 3R-methylcyclohexanone 72 (commercially available) as outlined in Scheme VII.

The hydrazone 73 was formed quantitatively in THF upon mixing the ketone 72 with p-toluenesulfonylhydrazide. Evaporation of solvent afforded 73. Shapiro reaction of 73 with alkyllithium in TMEDA gave a vinyl anion, which was quenched with dry DMF to afford the isomeric aldehydes 74/75 in modest yield (1:1 mixture). Attempts to improve this reaction by altering the base were unsuccessful. Silylanion addition to 74/75 followed by in situ acylation gave the propionate esters 76 in good yield. At this stage, isomeric contaminant could not be removed and was simply carried through the synthesis. Thus, Claisen ester enolate rearrangement of 76 gave a complex mixture of acid 77. At this point some chromatographic separation was possible, and 77 had a lower percent isomeric contamination relative to 76. Ozonolysis of 77 followed by cyclization in acetone afforded only one discernible product: the isomeric analog 29i. The fact that 29i had been produced by the sequence in Scheme VII and not 29 was determined by independent synthesis of 29 as shown in Scheme VIIa.

The chiral ketone 113, prepared from isopulegol, was reacted with methoxy-dimethylsilyltrimethylsilylmethyllithium (T. F. Bates, and R. D. Thomas. *J. Org. Chem.* 54, 1784 (1989)) to afford 114 as an E/Z mixture. Simple deprotection/oxidation served to convert 114 to the acid 115. Upon ozonolysis of 115 in methanol, removal of solvent, and addition of either acetone or acetaldehyde and acid catalyst, the tricyclics 29 and known 116 (Y. Imakura, T. Yokoi, T. Yamagishi, J. Koyama, H. Hu, D. R. McPhail, A. T. McPhail, and K.-H. Lee. *J. Chem. Soc. Chem. Commun.* 372 (1988)) were produced. The $^1$H NMR spectra of peroxide 29 (Scheme VIIa) and 29i by differed slightly, while their melting points and $[\alpha]_D$ were quite similar.

The regioisomeric problem upon fragmentation of the tosylhydrazone (i.e., production of mix 74/75) was overcome by increased substitution for increased selectivity. Therefore 3R-pulegone was used as a starting material for synthesis (Scheme VIII). The enolate of pulegone was generated with lithium isopropylcyclohexylamide (LICA) and alkylated with methyl iodide to furnish mainly 2,3-dimethyl-6-isopropylidene cyclohexanone 78 along with by-product 79, Scheme VII

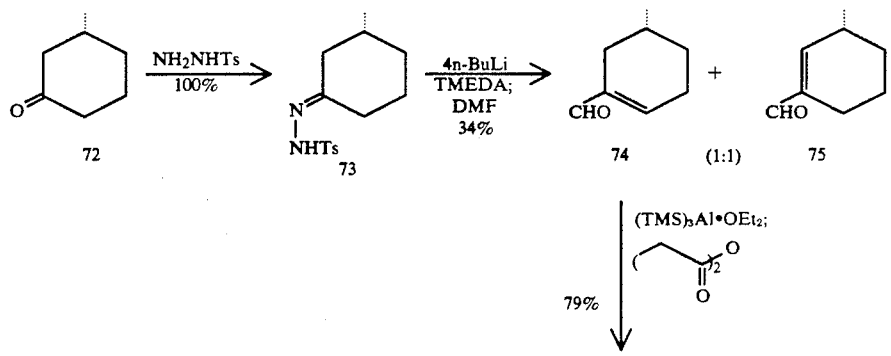

Scheme VII -continued

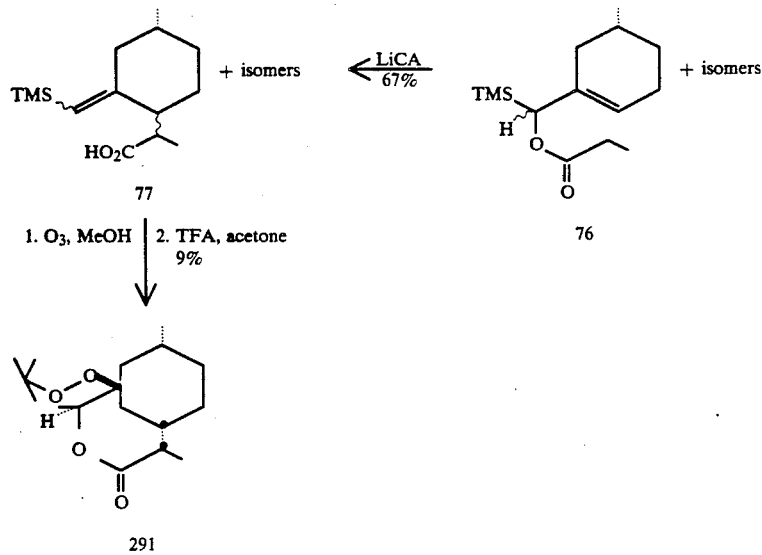

Scheme VIIa

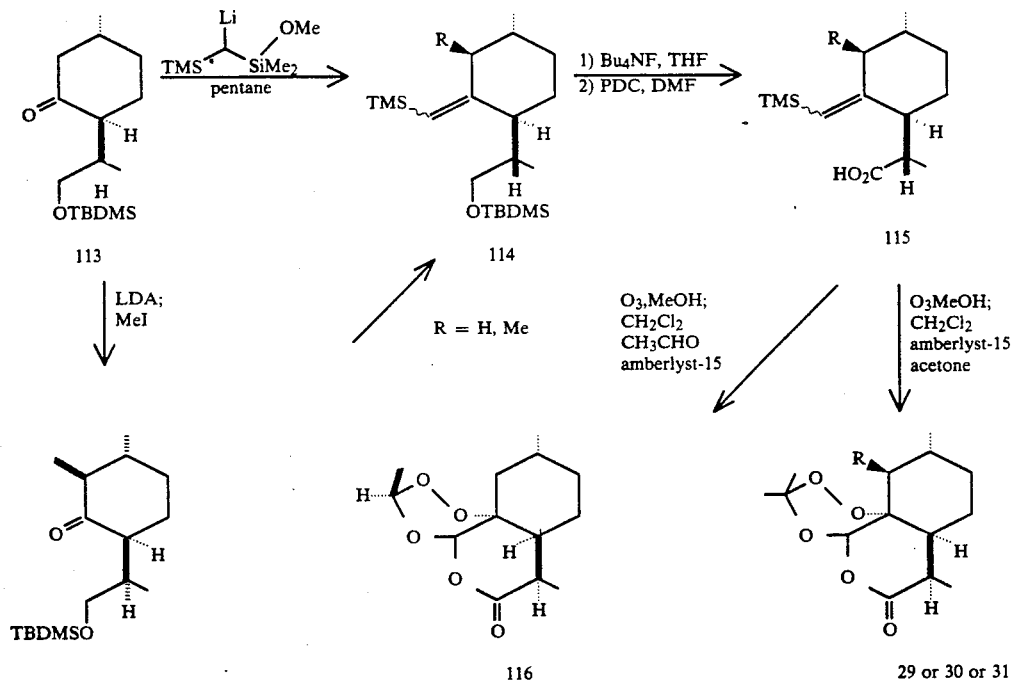

which was previously observed by Reusch et al., (Lee, R. A., McAndrews, C., Patel, K. M., and Reusch, W. Tetrahedron Lett. 965 (1973)) but 79 did not react in the following conversion of crude material. When the mixture containing the isopropylidene 78 was placed in acid and submitted to prolonged heating, acetone distilled prior to the water azeotrope of the epimeric mix of 80:81 (1:1.96, as determined by NMR) in 72% yield. The corresponding tosylhydrazone mix 82 from the mix of 80:81 was made as before and underwent n-butyllithium-effected fragmentation in TMEDA to a regioisomerically pure cyclohexenyl anion, which was capped with dimethylformamide to afford isomeric aldehydes 83 in 76% yield. The mix was treated with tris(trimethylsilyl)aluminum (III) etherate (L. Rosch and G. Altman, J. Organomet. Chem., 195, 47 (1980).It should be noted that this procedure has failed to work in our hands, as well as others: See B. Trost, J. Yoshida, and M. Lautens, J. Amer. Chem. Soc., 105, 4494 (1983). However, a procedure which works is provided in the experimental. The reagent can be titrated as described or by reaction with peperonal: L. Rosch, G. Altman, and W. Otto, Angew. Chem. Int. Ed. Engl., 20 581 (1981)) and followed by acetylation to provide a mixture of all possible diastereomers of 84. The lack of selectivity was surprising in contrast to the total synthesis of QHS, in which a synthetic intermediate substrate differs in the presence of a 6'-methyl instead of a larger alkyl chain. Regardless, the mixture 84 upon exposure to lithium diethylamide rearranged to a mixture of diastereomeric cyclohexylacetic acids, which upon rigorous chromatographic separation furnished geometric isomers of acid 85 in a 1:1 ratio by NMR, in 28% yield. The acid 85 was submitted to single-pot exposure to ozone and acidification to give trioxane 30 in 22% yield. Alternatively the acid 85 was methylated via the corresponding LDA-generated dianion to the propionic acid 86, which was subsequently reacted with ozone and acidified to provide trioxane 31. The two optically active trioxanes 30 and 31 have been assessed for their antimalarial activity. In addition, all three optically active trioxanes, 29, 30 and 31, display temperature-dependent NMR behavior.

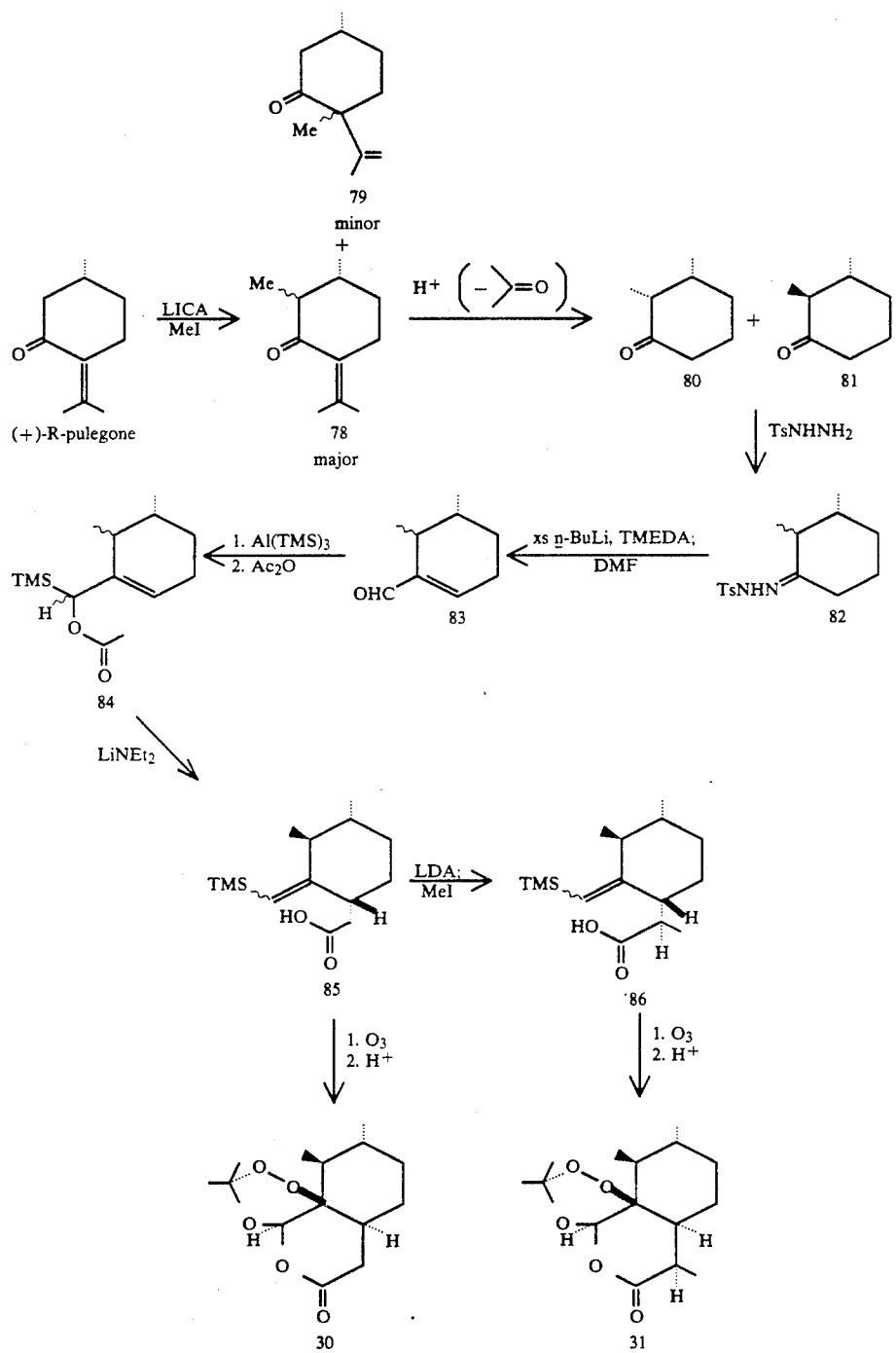

Scheme VIII ii. Ring D Seco Analogs

This novel class of Artemisinin (1) analogs is derived conceptually by scission of the 8a, 9 bond of 1:

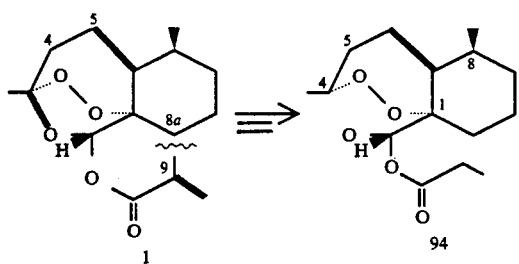

Such compounds are useful as antimalarial agents. While not wishing to be bound by theory, the inventors herein postulate that this is because the crucial peroxy moiety is held in the requisite relative orientation for maximal activity, yet the carbonyl group is capable of rotation into novel orientations unavailable to the natural product. Furthermore, the carbonyl substituent is now readily introduced by simple acylation reactions. Other virtues of this class of compounds is: (1) synthetic accessability (low number of reactions in sequence); (2) wide variety of analogs available (type and position); and (3) optical activity.

As shown in Scheme X, 94 was available from the common, total-synthetic, intermediate 6. Using newly reported methodology for the introduction of vinylsilanes, (T. F. Bates, and R. D. Thomas. *J. Org. Chem.* 54, 1784 (1989)) 6 was reacted smoothly with methoxydimethylsilyltrimethylsilyl methyllithium in pentane to afford the E/Z vinyl-silane 89 in 38% yield. The main by-product in this reaction was the ketone 6 which could be recycled; thus based on recovered 6, the yield of 89 was 83%. Hydrolysis of the ketal 89 occurred without protodesilylation upon exposure to aqueous oxalic acid absorbed on to silica gel to give the ketone 90 in 80% yield. Upon low temperature ozonolysis of 90 in methanol, a remarkably stable dioxetane 91 was produced as evidenced by the $^1$H NMR spectrum (w 6.1, s). On prolonged standing, 91 underwent [2+2]cycloreversion to mainly afford the diketone 98. By contrast, when dioxetane 91 was intercepted with Lewis acid (BF$_3$), a crystalline aldehyde-ketal (92) was produced in good yield (69%).

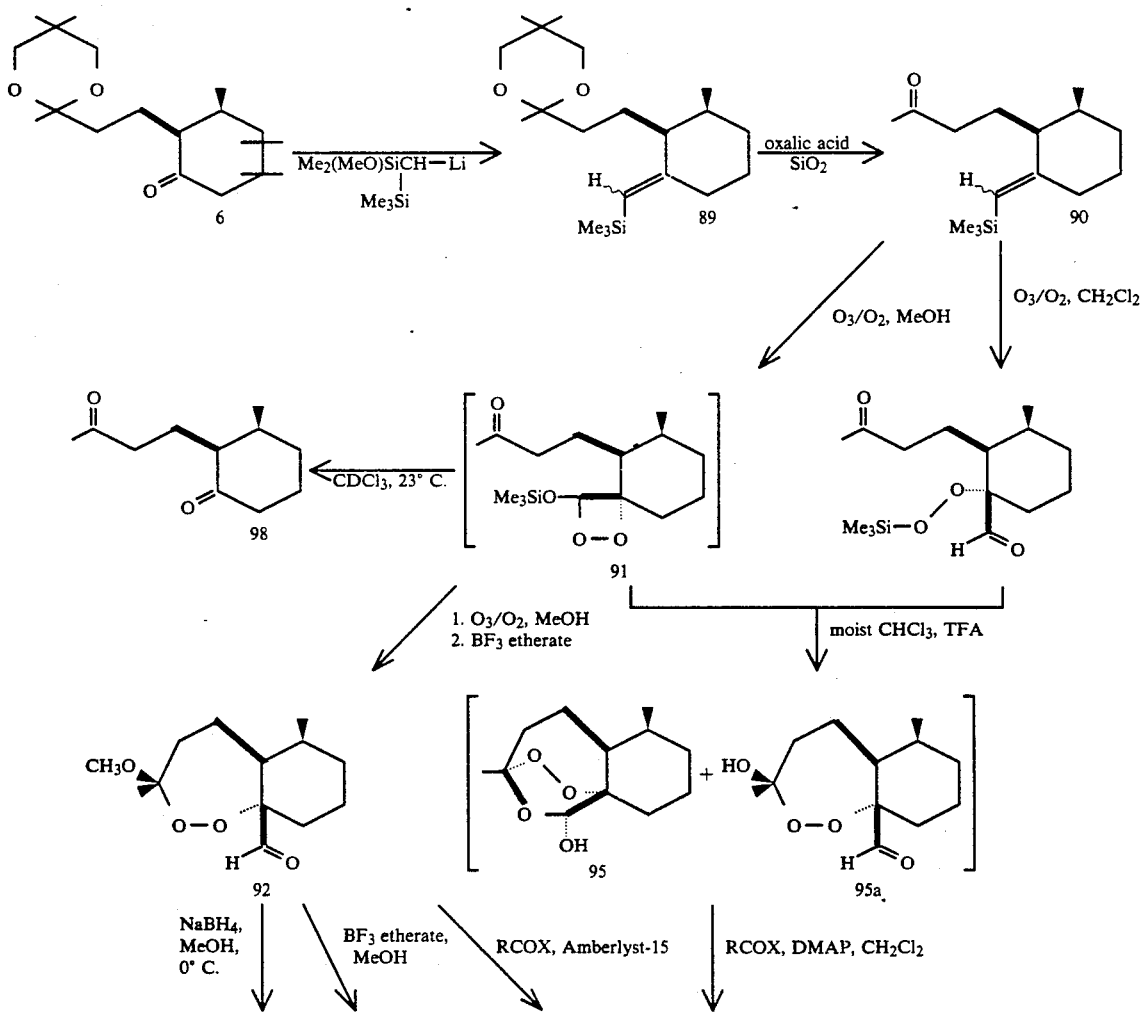

Scheme X

-continued
Scheme X

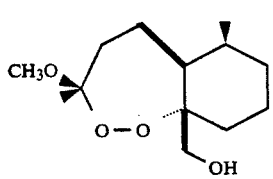 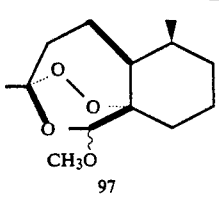 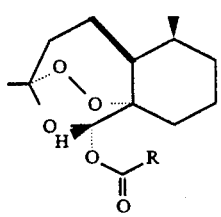

93, R = CH$_3$
94, R = CH$_2$CH$_3$
96, R = OCH$_2$Ph pTsOH, CH$_2$Cl$_2$

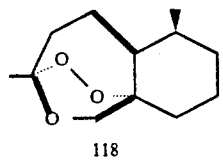

The aldehyde 92 is a useful intermediate due to its chemical stability in storage and ready conversion to artemisinin analogs. On treatment of 92 in propionic anhydride with protic acids (HClO$_4$ or H$_2$SO$_4$) or more conveniently with polymer bound acid (Amberlyst-15), with or without co-solvent (CH$_2$Cl$_2$), the 8a,9-seco analog of artemisinin 94 was obtained in 22% yield. It was also possible to treat the dioxetane 91 under the same conditions to arrive at 94 or 93 by substituting acetic anhydride for propionic anhydride, respectively, and in this fashion the analog 93 was obtained in 30% yield.

Hydrolysis of the dioxetane 91, or of the ketal 92, lead to an inseparable mixture with the expected product 95, which was the bicyclic isomer 95a.

95 ⇌ 95a

The mixture was 1:2 (95:95a), and underwent standard acylation reactions to give, for example, 93 on treatment with Ac$_2$O/pyridine/CH$_2$Cl$_2$. Carbonates were available from 95, such as 96, on treatment with various chloroformates in pyridine/CH$_2$Cl$_2$. In other words, the alcohol 95 could be funneled away from the mixture by reaction with electrophiles, providing the desired tricyclic products.

The bicyclic aldehyde 92 could also be isomerized to the tricyclic ketal 97 under dehydrating conditions in the presence of an alcohol.

Facile reduction of the aldehyde 92 to the alcohol 117 occurred with NaBH$_4$ in MeOH at 0° C. Exposure of 117 to acid in CH$_2$Cl$_2$ led to the expected trans ketalization product 118 in 79% overall yield. The product 118 is, of course, the A, B, and C rings of artemisinin.

3c. Flexible, Abbreviated QHS Analogs

In connection with our efforts to identify minimal structural requirements and to design QHS compounds having increased flexibility, we targeted peroxide esters 32 and 33, which were prepared as rapidly as hoped.

Commercially available 2-ethylbutene was epoxidized with m-chloro-perbenzoic acid to 87, which was ring-opened in situ upon addition of t-butyl hydroperoxide and p-toluenesulfonic acid. The crude peroxide alcohol 88 was divided into equal portions and acylated to either propionate 32 or butyrate 33, respectively. These esters 32 and 33 are being tested for antimalarial activity, but unfortunately exist as oils. Therefore projected analogs in this novel series involve esters of alcohol 88 that will provide solids, if warranted by the antimalarial activity of 32 and 33.

Scheme IX

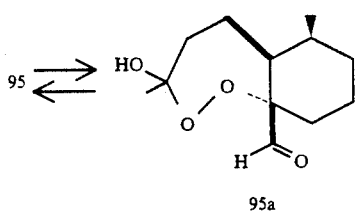

-continued
Scheme IX

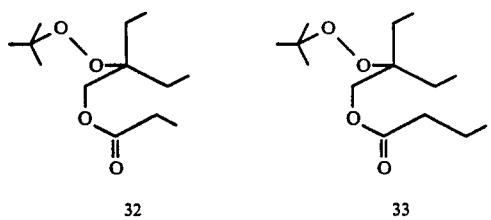

4. Biological Results

In vitro antimalarial activity for various QHS analogs was evaluated and is presented in Tables 2 and 3. The analogs have been segregated arbitrarily here into those compounds in which the tetracyclic skeleton is intact (Table 2) and various ring-cleaved analogs (Table 3). The activities of the conventional malaria therapeutics chloroquine, mefloquine, and pyrimethamine is included for comparison. (The designation "NA" indicates that biological data for those analogs is not currently available).

It may be seen from the tables that the C9-ethyl QHS analog 17 displays relatively high potency (11.7 and 6.17 times as potent as QHS against the W-2 and D-6 clones, respectively, as shown in Table 2) and justifies further scrutiny of lactone substitution. The amide analog 16 is of interest due to its high relative potency (5 and 21.7 times that of QHS against W-2 and D-6 clones, respectively, Table 2), the potential oral stability expected from the replacement of the lactone of QHS by a lactam, and another available site for substitution (via N-alkyls).

The novel ring-cleaved analogs of Table 3 are readily prepared and display activity comparable to that of conventional therapeutics.

TABLE 2

| COMPOUND | SRI CODE NUMBER | IC$_{50}$ (ng/ml) W-2 CLONE | RELATIVE POTENCY | IC$_{50}$ (ng/ml) D-6 CLONE | RELATIVE POTENCY |
|---|---|---|---|---|---|
| Chloroquine | | 31.7 | 7 | 5.33 | 83 |
| Mefloquine | | 2.4 | 88 | 43.7 | 10 |
| pyrimethamine | | 120.8 | 2 | 0.35 | 1269 |
| (+)-artemisinin | | 2.11 | 100 | 4.44 | 100 |
| (+) | 4584 | 0.31 | 650 | 2.32 | 180 |
| (+/−) | 4580 | 3.92 | 48 | 33.70 | 12 |
| (+/−) | 4589 | 88.68 | 2 | 129.45 | 2 |

TABLE 2-continued
IC$_{50}$ Values for Selected Analogs of Artemisinin in Drug-Resistant Strains of *P. falciparum*
| COMPOUND | SRI CODE NUMBER | IC$_{50}$ (ng/ml) W-2 CLONE | RELATIVE POTENCY | IC$_{50}$ (ng/ml) D-6 CLONE | RELATIVE POTENCY |
|---|---|---|---|---|---|
| 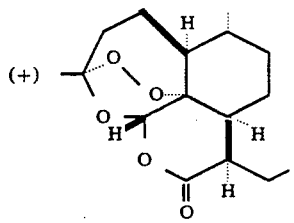 | 4586 | 0.18 | 1226 | 0.72 | 642 |
| 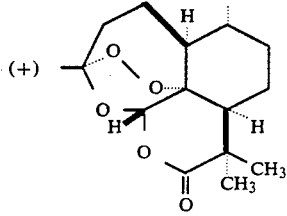 | 2800 | 25.53 | 0.63 | 20.89 | 2.1 |
| 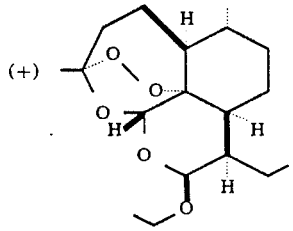 | 4598 | 0.18 | 272 | 0.22 | 550 |
| 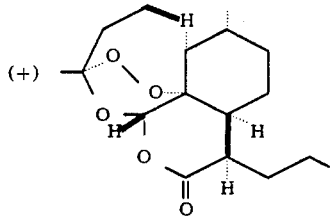 | 4599 | 0.04 | 1225 | 0.22 | 550 |
| 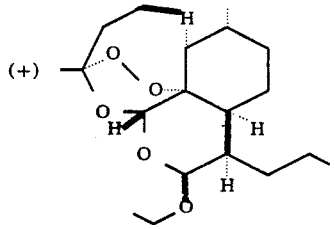 | 4600 | 0.63 | 76 | 0.39 | 120 |
| 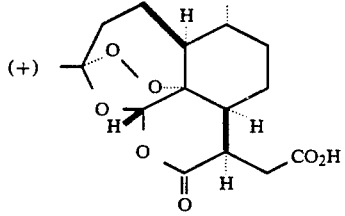 | 4595 | 150.99 | 0.3 | 829.92 | 0.15 |

TABLE 2-continued

IC$_{50}$ Values for Selected Analogs of Artemisinin in Drug-Resistant Strains of *P. falciparum*

| COMPOUND | SRI CODE NUMBER | IC$_{50}$ (ng/ml) W-2 CLONE | RELATIVE POTENCY | IC$_{50}$ (ng/ml) D-6 CLONE | RELATIVE POTENCY |
|---|---|---|---|---|---|
| (+) | 4588 | 0.41 | 656 | 0.53 | 1054 |
| (−) | 4585 | 0.42 | 502 | 2.05 | 214 |
| (+) | 2810 | NA | | NA | |
| (+) | 2811 | NA | | NA | |
| (+) | 2817 | 0.02 | 550 | 0.03 | 467 |
| (+) | 2818 | 63.94 | .0017 | 81.35 | .0017 |

TABLE 2-continued

| | | | | | | |
|---|---|---|---|---|---|---|
| | IC$_{50}$ Values for Selected Analogs of Artemisinin in Drug-Resistant Strains of *P. falciparum* | | | | | |
| COMPOUND | | SRI CODE NUMBER | IC$_{50}$ (ng/ml) W-2 CLONE | RELATIVE POTENCY | IC$_{50}$ (ng/ml) D-6 CLONE | RELATIVE POTENCY |
| (+) [structure] | | 2820 | 0.58 | 84 | 0.27 | 203 |
| (+) [structure] | | 2822 | 0.50 | 98 | 0.35 | 157 |
| (+) [structure] | | 2821 | 0.11 | 445 | 0.09 | 611 |
| (−) [structure] | | 2801 | NA | | NA | |
| (+) [structure] | | 2815 | Inactive | | Inactive | |
| (+) [structure] | | 2805 | 0.18 | 67 | 4.73 | 14 |

TABLE 2-continued

IC$_{50}$ Values for Selected Analogs of Artemisinin in Drug-Resistant Strains of *P. falciparum*

| COMPOUND | SRI CODE NUMBER | IC$_{50}$ (ng/ml) W-2 CLONE | RELATIVE POTENCY | IC$_{50}$ (ng/ml) D-6 CLONE | RELATIVE POTENCY |
|---|---|---|---|---|---|
| (−) 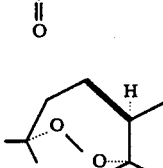 | 2812 | 96.03 | 0.11 | 74.23 | 1.88 |
| (−) 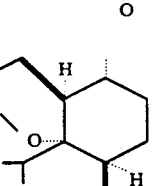 | 2803 | 0.07 | 171 | 0.45 | 149 |
| (−) 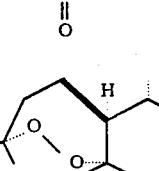 | 2804 | — | | 122.21 | 5.5 |
| (−) 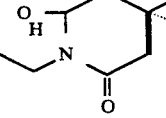 | 2809 | NA | | NA | |

TABLE 3

In Vitro IC$_{50}$ Values for Selected Tricyclic Artemisinin Analogs in Drug-Resistant Strains of *P. falciparum*

| COMPOUND | SRI CODE NUMBER | IC$_{50}$ (ng/ml) W-2 CLONE | RELATIVE POTENCY | IC$_{50}$ (ng/ml) D-6 CLONE | RELATIVE POTENCY |
|---|---|---|---|---|---|
| (+/−) 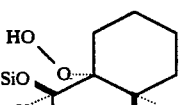 | 4581 | 2890.5 | 0 | 3016.4 | 0 |
| (+/−) 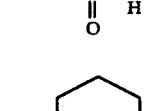 | 4593 | 178.01 | 0.5 | 188.61 | 0.4 |

TABLE 3-continued

In Vitro IC$_{50}$ Values for Selected Tricyclic Artemisinin Analogs in Drug-Resistant Strains of *P. falciparum*

| COMPOUND | SRI CODE NUMBER | IC$_{50}$ (ng/ml) W-2 CLONE | RELATIVE POTENCY | IC$_{50}$ (ng/ml) D-6 CLONE | RELATIVE POTENCY |
|---|---|---|---|---|---|
| (+/−) | 4582 | 38.09 | 6 | 22.21 | 20 |
| (+/−) | 4583 | 74.19 | 3 | 29.72 | 15 |
| (+/−) | 4590 | 11.8 | 7 | 13.95 | 5 |
| (−) | 4591 | 9.71 | 9 | 9.65 | 8 |
| (−) | 4592 | NA | | 1.28 | 58 |
| (+) | 4594 | 2.06 | 24 | 5.35 | 23 |

TABLE 3-continued

In Vitro IC$_{50}$ Values for Selected Tricyclic Artemisinin Analogs in Drug-Resistant Strains of *P. falciparum*

| COMPOUND | SRI CODE NUMBER | IC$_{50}$ (ng/ml) W-2 CLONE | RELATIVE POTENCY | IC$_{50}$ (ng/ml) D-6 CLONE | RELATIVE POTENCY |
|---|---|---|---|---|---|
| (−) | 2816 | 1.46 | 75 | 1.29 | 108 |
| (−) | 2819 | Inactive | | Inactive | |
| (+/−) | 4596 | Inactive | | Inactive | |
| (+/−) | 4597 | Inactive | | Inactive | |
| (+) | 2824 | NA | | NA | |
| (+) | 2807 | NA | | NA | |
| (+) | 2806 | NA | | NA | |

TABLE 3-continued

In Vitro IC$_{50}$ Values for Selected Tricyclic Artemisinin Analogs in Drug-Resistant Strains of *P. falciparum*

| COMPOUND | SRI CODE NUMBER | IC$_{50}$ (ng/ml) W-2 CLONE | RELATIVE POTENCY | IC$_{50}$ (ng/ml) D-6 CLONE | RELATIVE POTENCY |
|---|---|---|---|---|---|
| (+) [structure] | 2808 | 236 | 0.47 | 471.5 | — |
| (−) [structure] | 2814 | 4.60 | 24 | 10.98 | 12.7 |
| (+) [structure] | 2823 | — | — | 0.80 | 37 |

4. Use of the Products

The artemisinin analog compounds of this invention all contain the peroxy linkage which can lead to free radical intermediates in vivo; they should have antiprotozoan activities against a broad range of parasites such as Toxoplasma, Leishmania, Trypanosoma, etc., in addition to Plasmodia. In tests they have been demonstrated to have high activity in this application. They offer activity against drug-resistant forms of malaria and can even intervene in cerebral malaria where they can interrupt coma and reduce fever. These materials should also have antihelmenthic activity against such diseases as Schistosoma and Trichinella, etc. (R. Docampo et al., *Free Radicals in Biology*, Vol. VI, Chapter 8, p. 243, 1984, Academic Press, Inc.). In this application, the compounds are generally compounded into vehicles or carriers known in the art for administration to patients in need of such treatment. The mode of administration can be oral or by injection. Typical vehicles are disclosed in *Remington's Pharmaceutical Sciences*, Alfonso R. Gennaro, ed., Mack Publishing Company, Easton, Pa. (1985).

For oral administration, the compounds can be prepared as elixirs and suspensions in sterile aqueous vehicles and also can be presented admixed with binders, carriers, diluents, disintegrants and the like as powders, as pills, or as capsules. Typical liquid vehicles include sterile water and sterile sugar syrup. Typical solid materials include starch, dextrose, mannitol microcrystalline cellulose and the like.

For administration by injection, the materials can be presented as solutions/suspensions in aqueous media such as injectable saline, injectable water and the like. They can also be presented as suspensions or solutions in nonaqueous media such as the injectable oils including injectable corn oil, peanut oil, cotton seed oil, mineral oil, ethyl oleate, benzyl benzoate and the like. The nonaqueous media can, in some cases, permit substantial quantities of the medication to be administered as a depot in the patient's fat layer so as to obtain a prolonged release of the agent to the patient.

The materials of this invention are used in fairly large doses. Commonly, dose levels of from about 100 mg/day to as much as 10,000 mg/day are employed. The actual use level will vary depending upon the particular patient's response to the drug and to the patient's degree of affliction. In a particularly preferred utility, they are used against Plasmodia and, in that use, require dosages from 0.1 to 10 times that used with the natural product artemisinin.

The peroxide link presented by all of these compounds and the free radicals it can produce are useful in a range of industrial chemical settings, as well.

The invention will be further described with reference being made to the following examples. These are provided merely to illustrate one preferred mode for carrying out the preparation of the invention and to illustrate several embodiments of the compounds provided by this invention and are not to be construed as a limitation upon the scope of the invention.

Experimental Methods

Dry tetrahydrofuran (THF) was obtained 1 day after addition of flame dried 4 μ molecular sieves (ca. 2") to freshly opened 1 pint bottles of reagent grade THF (Mallinckrodt, AR grade). Dry diethyl ether was purchased (1 lb cans, anhydrous ether, Mallinckrodt). HPLC grade solvents were routinely used, such as dichloromethane, ethyl acetate, hexane, etc. Other reagents such as amines, were distilled from CaH$_2$ onto molecular sieves and stored under argon. Dry solvent or liquid reagent transfers were done with dry syringes under argon. All reactions were carried out under argon.

EXAMPLE 1

Total Synthesis of Artemisinin

Example 1A: Synthesis of Pulegone oxide (2)

Pure R(+)-pulegone 1 (Fluka purum grade, 152 g) was converted to the epoxide, according to the method of Reference 1, to give 119 g of 2 (74%). This material was sufficiently pure by NMR for use in the next reaction.

Example 1B: 5R-Methyl-2-thiophenylcyclohexanone (3)

The oxide 2 (119 g) from Example 1A was converted to the sulfide 3 by minor modification of the method of Reference 1.

A 60% oil dispersion of NaH (1.416 mole, 56.64 g) under argon was washed with hexane (3×50 mL) in order to remove the oil. Dry THF (1.5L) was added followed by a solution of thiophenol (1.416 mole, 146.5 mL) in dry THF (1.5L). The mixture was stirred at R.T. for 30 min and then the epoxide 2 (119 g) or 708 mmol) in dry THF (1.0L) was added. The resulting mixture was heated at reflux for 24 hr and allowed to cool. Ice (1 Kg) was added and the mixture stirred for 15 min. The mixture was extracted with Et$_2$O (2×500 g) and the combined organic phase was then washed with brine, dried over MgSO$_4$, filtered, and the solvent evaporated in vacuo to give crude 3 (157 g or ca. 100%), which was sufficiently pure (NMR) for the next reaction.

Example 1C: 5R-Methyl-2-phenylsulfinylcyclohexanone (4)

The sulfide 3 was oxidized, as described in Reference 2, to the sulfoxide 4.

Thus, 3 (155.8 g) was converted to crude 4 (241 g). Filtration chromatography on silica gel (723 g of 60–230 mesh) with 35→80% EtOAc/hexane gave pure 4 (158 g or 95%). The sulfoxide was stored under argon in the freezer.

Example 1D: 2,5,5-Trimethyl-2-(2'-(1''R-methyl-3''-oxocyclohex-2''-yl)-ethyl-1,3-dioxane (6)

5R-Methyl-2-phenylsulfinylcyclohexanone (4) (48.4 g, 205 mmoles) in dry THF (300 mL) was added to a solution of lithium diisopropylamide (W. Roush and W. Walts. *J. Amer. Chem. Soc.*, 106, 721 (1984)) (prepared from 63.0 mL [451 mmoles] of diisopropylamine and 189 mL of 2.5M solution of n-BuLi in hexane) in dry THF (300 mL) at −78° C. followed by dry 1,3-dimethyl-3,4,5,6-tetrahydro-2(1H)-pyrimidinone (DMTP) (200 mL). The mixture was stirred at −30° C. for 3 hr and then 2-(2'-bromoethyl)-2,5,5-trimethyl-1,3-dioxane[3] (52.7 mL, 226 mmoles) was added dropwise. The mixture was stirred at −30° C. for 1 hr and then was allowed to warm to room temperature for 1 hr. The mixture was poured into ice-cold, saturated ammonium chloride solution (500 mL) and was extracted with diethyl ether (2×500 mL). The organic layers were washed with water (3×500 mL) and brine (500 mL), dried (MgSO$_4$), and evaporated in vacuo to give 106 g of crude alkylation product (5). This was dissolved in THF (2.5L) to which was added water (300 mL). This solution was added to 60 g of aluminum (−45 +100 mesh), which was activated by sequential washing with 2% aqueous mercuric chloride for 20 sec followed by absolute ethanol and diethyl ether. The mixture was stirred at room temperature until the temperature reached about 35° C., at which point ice was gradually added to a cooling bath to control the exotherm. After 2 hr the mixture was filtered through celite under reduced pressure, the solids being washed with diethyl ether (1L). The filtrate was washed with 5% sodium hydroxide solution (2×1L) and brine (1L). The aqueous phases were sequentially extracted with diethyl ether (1L) and the combined organic phases were dried (MgSO$_4$) and evaporated in vacuo to give 66.0 g of crude material. This was purified by filtration chromatography on 660 g of silica gel 60 (70–230 mesh), eluting with EtOAc/hexane (5:95)→(25:75) to give 16.7 g of the product 6 together with 9.2 g of mixed fractions. The mixed fraction were repurified by flash chromatography on 184 g of silica gel 60 (230–400 mesh), eluting with EtOAc/hexane (7:93)→(25:75) to give an additional 5.0 g of the product 6. Total yield 21.7 g (37%). IR (thin film): 2960 (s), 2940 (m), 2880 (m), 1716 (s) cm$^{-1}$. NMR (400 MHz, CDCl$_3$: δ 3.501 (1H, d, J=11 Hz), 3.496 (1H, d, J=11 Hz), 3.454 (1H, d, J=11 Hz), 3.450 (1H, d, J=11 Hz), 2.30 (3H, m), 2.01 (2H, m), 1.83 (1H, m), 1.65 (6H, m), 1.34 (3H, s), 1.03 (3H, d, J=7 Hz), 0.93 (6H, s). C$_{13}$ NMR (400 MHz, CDCl$_3$): δ 213.2, 99.1, 70.5, 70.3, 57.1, 41.6, 41.4, 38.4, 33.5, 33.3, 29.9, 25.6, 22.7, 21.7, 20.8, 20.5. MS (m/e):268 (M$^+$), 253 (M-Me).

Analysis: Found: C, 71.73; H, 10.33. C$_{16}$H$_{28}$O$_3$ requires C, 71.64; H, 10.45%.

(Note: The ketone 6 was contaminated with the inseparable C-2a isomer (9:1 ratio).)

Example 1E: 2,5,5-Trimethyl-2-(2'-(1''R-methyl-3''-oxocyclohex-2''-yl)-ethyl) -1,3-dioxane p-tosylhydrazone (7)

A mixture of the ketone (6) (41.6 g, 155 mmoles), dry THF (1L), p-tosylhydrazine (31.8 g, 171 mmoles), and dry pyridine (41.6 mL) was evaporated in vacuo and kept at 40 mm Hg for 20 hr. The crude material was purified by filtration chromatography on 677 g of silica gel 60 (70–230 mesh), eluting with EtOAc/hexane (20:80)→(40:60) to give the product 7 (58.0 g, 86%) as a gummy solid. IR (CHCl$_3$): 3120 (m), 2955 (s), 2875 (s), 1735 (m), 1635 (2), 1605 (w), 1500 (w) cm$^{-1}$. NMR (400 MHz, CDCl$_3$): δ 7.81 (2H, d, J=8 Hz), 7.40 (1H, broad), 7.24 (2H, d, J=8 Hz), 3.44 (4H, m), 2.37 (3H, s), 2.19 (3H, m), 1.54 (8H, m), 1.27 (3H, s), 1.24 (3H, d, J=5 Hz), 0.94 (3H, s), 0.88 (3H, s). MS (m/e): 437 (M+H$^+$), 421 (M-Me).

Example 1F: 2,5,5-Trimethyl-2-[2'-(1''R-methyl-3''-formylcyclohex-3''-en-2''-y l)-ethyl-1,3- dioxane (8)

To a solution of the hydrazone 7 (23.8 g, 54.6 mmole) in dry TMEDA (400 mL) at −78° C. under argon was added n-BuLi (136.5 mL of 1.6M solution in hexane, 218.4 mmoles). The mixture was stirred at room temperature for 90 min and then was cooled to 0° C. After slow addition of dry DMF (54 mL), the mixture was stirred at 0° C. for 30 min and then was poured into ice-cold saturated ammonium chloride solution (2.0L). The product was extracted with ethyl acetate (2×1.0L) and washed with saturated ammonium chloride solution (1.0L), water (1.0L), and brine (1.0L). The combined organic extracts were dried (Na$_2$SO$_4$) and evaporated in vacuo to give 21.5 g of crude material, which was purified by flash chromatography on 215 g silica gel 60

(230–400 mesh) eluting with EtOAc/hexane (15:85), to give the product 8 (10.7 g, 70% as a pale yellow oil. IR (thin film): 2960 (s), 2870 (m), 2710 (w), 1685 (s), 1635 (w) cm$^{-1}$. NMR (400 MHz, CDCl3): δ 9.38 (1H, s), 6.73 (1H, t, J=4 Hz), 3.472 (1H, d, J=11 Hz), 2.28 (2H, m), 1.91 (1H, m), 1.71 (5H, m), 1.39 (2H, m), 1.31 (3H, s), 0.94 (3H, s), 0.89 (3H, s), 0.86 (3H, d, J=7 Hz). $^{13}$C NMR (400 MHz, CDCl$^3$): δ 194.7, 151.2, 99.0, 70.3, 41.6, 37.7, 35.0, 29.9, 28.5, 27.5, 26.1, 23.9, 23.0, 22.7, 21.0, 18.6, 14.1. MS (m/e): (M-Me).

(Note: This aldehyde is unstable and should be stored, for short periods, under argon in the freezer. It should be used as soon as possible.)

Example 1G:
2,5,5-Trimethyl-2-(2'-(1"R-methyl-3"-trimethylsilylhydroxyomethyl-cyclohex-3"-en-2"-yl)-ethyl)-1,3-dioxane acetate ester (9)

(a) Tris(trimethylsilyl)aluminum etherate

A mixture of Fluka aluminum powder (20 g, 100–200 micron), Fluka aluminum granules (5 g, 0.15-1.7 mm), dry diethyl ether (200 mL), and iodine (2.0 g) was magnetically stirred under argon in a 3-neck 500 mL r.b. flask until the iodine color had disappeared. Mercury (20 g) was added, followed by chlorotrimethylsilane (120 mL, 945 mmole). The mixture was stirred at room temperature for 3 hr and lithium wire (Aldrich, 3.2 mm diam. −0.01% Na, 1 mole, 7.0 g, 155 cm) was added in small pieces (0.3-0.5 cm). The stirred mixture was heated in an oil bath at 35°–40° C. for 48 hr. After allowing to cool, the mixture was filtered by suction through dry celite under argon directly in a r.b. flask. Complete transference was ensured by washing the reaction flask and filter funnel with dry diethyl ether and the combined filtrates were evaporated in vacuo. The residue was kept under high vacuum for 2 hr. Pentane (50 mL) was added and the mixture was swirled. After the solid had settled the solution was decanted via syringe and transferred to a new flask under argon. Another portion of pentane (50 mL) was added to the solid material and the procedure was repeated, combining the two pentane solutions. As the pentane solution of tris(trimethylsilyl)aluminum etherate is highly pyrophoric, all operations involving synthesis, storage, and use of the material were carried out under an inert atmosphere. The solution is indefinitely stable stored under argon in a freezer. The solution may be assayed by reaction with 1-formylcyclohexene, freshly prepared from 1-hydroxymethylcyclohexene by manganese dioxide oxidation. The aluminum reagent is added dropwise to 1.0 mmole of the aldehyde in dry diethyl ether (2 mL) under argon at −78° C. The transient red color with each drop no longer appears when the reaction is complete but the reaction is best monitored by thin layer chromatography, the starting material being readily visualized by UV while the product is not, even though the R$_f$s are similar. On a run following the procedure above, 0.67 mL of the aluminum reagent was required for the assay, indicating a concentration of 1.5N. This figure can be variable, however, depending on the batch of aluminum used and other factors.

(b)
2,5,5-Trimethyl-2-(2'-(1"R-methyl-3"-trimethylsilylhydroxyometh yl-cyclohex-3"-en-2"-yl)-ethyl)-1,3-dioxane acetate ester (9)

To the aldehyde (8) (10.6 g, 37.9 mmoles) in dry diethyl ether (100 mL) under argon at −78° C. was added tris(trimethylsilyl)aluminum etherate (40.0 mmoles, 100 mL of 0.4M solution in pentane). After stirring at −78° C. for 10 min, acetic anhydride (18.9 mL, 200 mmoles) was added followed by 4-dimethylaminopyridine (200 mg). The mixture was stirred at room temperature for 16 hr and then was poured into ice-cold saturated sodium potassium tartrate solution (300 mL). This was extracted with diethyl ether (2×300 mL). and washed with saturated sodium potassium tartrate solution (300 mL) and brine (300 mL). The combined organic layers were dried (MgSO4) and evaporated in vacuo to give 22.2 g of crude material. This was purified by flash chromatography on 222 g of silica gel 60 (230–400 mesh), eluting with EtOAc/hexane (5:95)→(10:90) to give 13.2 g (88%) of the product 9 as a colorless oil. IR (CHCl3): 3000 (m), 2960 (s), 2930 (s), 2875 (s), 1725 (s), 1645 (w) cm$^{-1}$. NMR (400 MHz, CDCl3): δ 5.84 (1H, m), 5.25 (1H, m), 3.40 (4H, m), 2.05 (3H, s), 2.05–1.20 (10H, m), 1.32 (3H, s), 1.01 (3H, s), 0.88 (6H, m), 0.02 (9H, s). MS (m/e): 396 (M+), 395 (M-H). Analysis: Found: C, 65.24; H, 10.13. C22H40SiO4+1/2 H2O requires C, 65.19, H, 10.12%.

Example 1H:
2,5,5-Trimethyl-2-(2'-(4"-carboxymethyl)-1"R-methyl-3"-trimethylsilyl methylenecyclohex-2"-yl)ethyl)-1,3-dioxane (10)

To freshly distilled dry diethylamine (10.3 mL, 100 mmole) in dry distilled THF (300 mL) at 0° C. under argon was added n-BuLi (63 mL or 100 mmoles of a 1.6M solution in hexane). The mixture was stirred at 0° C. for 10 min and then was cooled to −78° C. The ester 9 (19.8 g, 50 mmole) in dry distilled THF (50 mL) was added dropwise over 20 min and the mixture was stirred at −78° C. for 4 hr followed by room temperature for 4 days. Then the mixture was poured into ice-cold, saturated ammonium chloride solution (1L) with 25 mL of 5N hydrochloric acid and extracted with chloroform (3×300 mL). The organic extracts were washed with brine (1L), dried (MgSO4), and evaporated in vacuo to give 29.8 g of crude material. This was purified by flash chromatography on 400 g of silica gel 60 (230–400 mesh), eluting with (1% HOAc/EtOAc)/hexane (10:90)→(25:75) to give the product 10 (11.0 g, 56%). IR (CHCl3): 3575 (w), 3030 (w, broad), 3000 (m), 2955 (s), 2870 (m), 1710 (s), 1610 (w) cm$^{-1}$. NMR (CDCl3): δ 5.34 (1H, s), 3.48 (4H, m), 2.79 (1H, m), 2.51 (2H, m), 2.10 (1H, m), 1.84 (4H, m), 1.60 (4H, m), 1.39 (1H, m), 1.34 (3H, s), 1.13 (1H, m), 0.99 (3H, s), 0.91 (3H, d, J=7 Hz), 0.87 (3H, s), 0.07 (9H, s). MS (m/e): 396 (M+), 381 (M-Me). High-resolution MS: Found: 396.270. C22H40SiO4 requires 396.269.

Example 1I:
2,5,5-Trimethyl-2-(2'-(4"-(1'''-carboxyethyl)-1"R-methyl-3"-tri methylsilyl methylenecyclohex-2"-yl)-ethyl)-1,3-dioxane (11)

To a solution of diisopropylamine (413 mL, 2.96 mmole) in dry THF (5 mL) under argon at 0° C. was added n-buli (2.96 mmoles, 1.91 mL of 1.55M solution in hexane). The mixture was stirred at 0° C. for 15 min and then cooled to −78° C. The acid (10) (532 mg, 1.34 mmol) in dry THF (2 mL) was added via syringe and the mixture was allowed to warm to room temperature over 30 min. The mixture was heated at 50° C. for 2 hr and recooled to 0° C. Methyl iodide (210 mL, 3.36 mmoles) was added via syringe and the mixture was stirred at room temperature for 1 hr. The mixture was poured into ice-cold, saturated ammonium chloride solution (20 mL) and extracted with chloroform (2×20 mL). The organic layers were washed with brine (20 mL), dried (MgSO$_4$), and evaporated in vacuo to give 640 mg of crude material. This was purified by flash chromatography on 64 g of silica gel 60 (230-400 mesh), eluting with (1% HOAc/EtOAc)/hexane (20:30) to give the product (12) (535 mg, 97%) as a colorless gum. IR (CHCl$_3$): 3600 (w), 3500 (w), 3000 (s), 2950 (s), 2870 (s), 2650 (w, broad), 1705 (s), 1605 (m) cm$^{-1}$. NMR (400 MHz, CDCl$_3$): δ 5.31 (1H, s), 3.52 (2H, d, J=11 Hz), 3.41 (1H, d, J=1188 Hz), 3.39 (1H, d, J=11 Hz), 2.77 (1H, dq, J=12, 7 Hz), 2.34 (1H, m), 2.10 (1H, ddd, J=1, 2, 10 Hz), 1.82 (4H, m), 1.64 (1H, m), 1.56 (2H, m), 1.45 (1H, m), 1.39 (1H, m), 1.33 (3H, s), 1.10 (1H, d, J=7 Hz), 0.98 (3H, s), 0.92 (3H, d, J=7 Hz), 0.86 (3H, s), 0.09 (9H, s). MS (m/e): 410 (M+), 395 (M-Me). Exact mass calc. for C$_{23}$H$_{42}$SiO$_4$: 410.285. Found: 410.286.

Example 1J: (+)-Artemisinin (12)

The following reactions were carried out with hood lights off.

To a solution of the ketal-acid 11 (170 mg; 0.426 mmol) in CH$_2$Cl$_2$ (40 mL) at −70° C. was bubbled a stream of O$_3$/O$_2$ (7 p.s.i., 0.4 L/min, 70 v) for 2 min. The mixture was analyzed by TLC (3:7 EtOAc/hexane), and shown to be complete. At this point the reaction mixture was purged with argon, BHT was added (20 mg), followed by silica gel (4.5 g) and 3M H$_2$SO$_4$ (2 mL). The mixture was warmed to 22° C. and stirred efficiently for 4 days. Solid NaHCO$_3$ (2 g) was added, the mixture was stirred 30 min, filtered, and the filter cake washed well with EtOAc/CH$_2$Cl$_2$ (1:9). The solvent was evaporated to give crude 12 (124 mg), which was then flash chromatographed on silica gel (10 g) with EtOAc/hexane (3:7) to afford pure 12 (42 mg or 35% as a white solid which could be crystallized from hexane. The spectroscopic (NMR, IR, MS), physical (m.p., rotation), and chromatographic (TLC) properties of this product were identical with an authentic sample of (+)-artemisinin. In addition to 12, the above chromatography provided a slightly less polar substance (12 mg or 10%) which was shown to be (+)-deoxyartemisinin by spectroscopic comparison to an authentic sample.

EXAMPLE 2

Radiolabelled Artemisinin Analogs

Example 2A:
2,5,5-Trimethyl-2-(2'-(4''-(1'''-carboxy-2'''-14C-ethyl)-1''R-methyl-3''-tri-methylsilylmethylenecyclohex-2''-yl)-ethyl)-1,3-dioxa ne ($^{14}$C-11)

A solution of diisopropylamine (2.2 mmol) in anhydrous THF (4 mL) was cooled to 0° C. and treated with n-buLi (1.42 mL of 1.55M in hexane, 2.2 mmol). The resulting solution was stored at 0° C. for 15 min. Next, the solution was cooled to −78° C. and a solution of (1) (396 mg, 1 mmol) in THF (2 mL) was added slowly. The resulting solution was allowed to warm to room temperature and then heated to 50°-55° C. for 2 hr. The resulting solution was freeze-degassed and carbon-14 methyl iodide (350 mg, 2.44 mmol, 117 mCi, 48 mCi/mmol) added by vacuum transfer at −196° C. The resulting solution was stirred under a closed system at the vapor pressure of THF at room temperature for 1 hr. Next, the excess $^{14}$CH$_3$I and THF solvent were removed by vacuum transfer for waste disposal. The dry residue of crude product was treated with saturated ammonium chloride (10 mL) and extracted with chloroform (4×10 mL). The lower organic phases were washed in succession with saturated sodium chloride (10 mL). The crude product was purified with a column of silica gel (Baker "Flash," 25 g) eluting with a varying concentration of hexane/(1% acetic acid in ethyl acetate) from 80/20 to 60/40. Evaporation left 377 mg of $^{14}$C-11 (42.3 mCi, 92% yield).

Example 2B: 16-$^{14}$C-(+)-Artemisinin ($^{14}$C-12) and 15-$^{14}$C-(+)-deoxyartemisinin ($^{14}$C-12a)

Ozone (7 psi, 0.4 L/min, 70 v) was bubbled into a solution of (2) (0.92 mmol) in CH$_2$Cl$_2$ (100 mL) at −78° C. for 4 min. The excess ozone was purged with argon bubbling and the solution treated with BHT (35 mg) in CH$_2$Cl$_2$ (1 mL). Next, silica gel (9.5 g) was added followed by 3M H$_2$SO$_4$ (3.5 mL). The resulting mixture was allowed to warm to room temperature and stirred for 16 hr. The mixture was treated with sodium bicarbonate (3 g) and stirred for 1 hr. The crude product was isolated by filtration, rinsing with CH$_2$Cl$_2$/EtOAc (90/10) (100 mL). The solvent was removed in vacuo and the crude product placed on a column of Baker "flash" silica gel (32 g) and eluted with a varying concentration of hexane/ethyl acetate from 95/5 to 90/10. After elution with 200 mL of 95/5 and 400 mL of 90/10, 2.5 mCi of deoxy compound ($^{14}$C-12a) was collected from 50 mL of 90/10. The next 20 mL of 90/10 gave 0.2 mCi of a mixture of ($^{14}$C-12) and ($^{14}$C-12a) and the next 100 mL of 90/10 gave 7.8 mCI of product $^{14}$C-12. Analysis by autoradiography revealed product $^{14}$C-12 to be 95.3% radiopure. This was repurified by the above procedure yielding 7.26 mCi of 98.3% radiopure product $^{14}$C-12 by autoradiography (17% yield). The specific activity was 46.5 mCi/mmol.

EXAMPLE 3

2,5,5-Trimethyl-2-(2'-(5''(2'''-N-methylacetamide)-1''R-methyl-6'' E-trimethyl silylmethylenecyclohexyl)ethyl)-1,3-dioxane (37)

To a solution of the methyl ester 34 (394 mg or 0.96 mmol) in methanol (15 mL) was added aq. methylamine (40%, 6 mL). The mixture was refluxed under argon for 10 h, then stirred overnight at room temperature. The reaction mixture was poured into sat. aq. NH$_4$Cl (150 mL) and extracted with EtOAc (3×70 mL). The combined organic layer was washed with sat. aq. NH$_4$Cl (1×100 mL), dried over MgSO$_4$, and filtered; the solvent was evaporated to give crude 37. PTLC chromatography on four plates (SiO$_2$, 1.5 mm) with 1:1 EtOAc/hexane afforded the pure amide 37 as a glass, 150 mg or 38% yield.

NMR (400 MHz): δ 0.05 (s, 9H), 0.81 (s, 3H), 0.90 (d, J=7.0 Hz, 3H), 1.08 (s, 3H), 1.36 (s, 3H), 2.12 (m, 1H), 2.24 (dd, J=6.8, 13.4 Hz, 1H), 2.40 (dd, J=9.1, 13.4 Hz, 1H), 2.70 (d, J=4.8 Hz, 3H), 2.85 (m, 1H), 3.38 (dq, J=2.2, 3.3, 11.2 Hz, 2H), 3.61 (dd, J=8.8, 11.2 Hz, 2H), 5.38 (s, 1H), 6.10 (bs, 1H). IR (neat oil): 3300, 2980, 1640, 1550, 1250, 1120, 1090, and 840 cm$^{-1}$. EIMS: m/e 409 (M+), 394, 324, 308, 305, 265, 253.

EXAMPLE 4

(1S, 3R, 4R)4-Methyl-N-methyl-(3'-oxobutyl)-2E-trimethylsilylmethylene cyclohexylacetamide (38)

To a slurry of 230–400 mesh silica gel 60 (400 mg) and $CH_2Cl_2$ (4 mL) was added 10% aq. oxalic acid (160 μL). The mixture was stirred under argon until complete mixing was evident, then the ketal 37 (150 mg, 0.367 mmol) in $CH_2C_{12}$ (4 mL) was added. The mixture was stirred for 20 h, filtered, and washed with EtOAc (3×15 mL). The combined organic layer was dried over $MgSO_4$ and filtered; the solvent was removed to give crude 26. Chromatography on one PTLC plate ($SiO_2$, 1.5 mm) with 93:7 $CHCl_3$/MeOH afforded the pure keto-amide 38 as a white solid, 104 mg (88%).

NMR (400 MHz, $CDCl_3$): δ 0.06 (s, 9H), 0.92 (d, J=7.1 Hz, 3H), 2.15 (s, 3H), 2.29 (dq, J=7.1, 13.9 Hz, 2H), 2.36 (dq, J=5.0, 11.5, 16.5 Hz, 1H), 2.51 (dq, J=5.0, 11.5, 16.5, Hz, 1H), 2.75 (d, J=4.8 Hz, 3H), 2.85 (q, J=7, 14 Hz, 1H), 5.43 (s, 1H). IR ($CDCL_3$): 3470, 2960, 1710, 1660, 1600, 1520, 1410, 1360, 1250, 850, 840 $cm^{-1}$. EIMS: m/e 323 (M+), 308, 280, 266, 253, 238, 234.

EXAMPLE 5

(−)-Octahydro-3,6,11-trimethyl-3,12-epoxy-12H-pyridino-[4.3-j] 1,2-benzo dioxepin-10(3H)-one (16)

Ozonized oxygen (0.4 L/min, 7 psi., 70 V) was bubbled through a solution of the keto-amide 38 (74 mg or 0.229 mmol) in MeOH (15 mL) at −78° C. until a blue color remained (about 2 min). After 5 min, argon was passed through the solution (15 min), and then the solvent was removed by rotary evaporation (bath temperature ca. 20° C.). The residual oil was placed under high vacuum for 2 h, dissolved in $CHCl_3$ (3 mL), and then treated with $CF_3CO_2H$ (30 μL). After 4 h at ambient temperature, solid $NaHCO_3$ (500 mg) was added. The mixture was stirred for 15 min then filtered, and the solvent was evaporated. Chromatography on one PTLC plate ($SiO_2$, 1.0 mm) with 6:4 EtOAc/hexane gave 16 as an oil (35 mg or 54% yield). Crystallization from pet. ether gave pure 4, mp 78°–80° C. $[α]_D^{22} = -12.2°$ (c=1.17, $CHCl_3$).

$^1H$ NMR (400 MHz): δ 0.97 (d, J=6.2 Hz, 3H), 1.34 (s, 3H), 1.76 (dt, J=4.8, 13.6 Hz, 1H), 1.95 (dq, J=2.9, 6.0, 9.5 Hz, 1H), 2.00 (dq, J=2.9, 4.4, 15.2 Hz, 1H), 2.10, (d, J=17.5 Hz, 1H), 2.39 (m, 1H), 2.96 (s, 3H), 3.10 (dd, J=5.4, 17.5 Hz, 1H), 5.18 (s, 1H). $^{13}C$ NMR: d 19.79, 25.06, 25.35, 28.96, 29.00, 33.50, 33.96, 37.88, 39.15, 51.34, 79.52, 79.90, 104.69, 168.67. IR ($CHCl_3$): 3005, 2940, 2880, 1640, 1455, 1410, 1385, 1370, 1330, 1295, 1260, 1160, 1150, 1095, 1035, 950, 895, 870 $cm^{-1}$. CIMS: m/e 299 ($M+NH_4^+$), 282 ($M+H^+$), 264, 240, 222. Anal. Calcd. for $C_{15}H_{23}NO_4$: C, 64.06; H, 8.18. Found: C, 64.05; H, 8.11.

EXAMPLE 6

(1"S,2"R,5"S.3'''R)2-[2'-(5"-(3'''-t-Butyl 3'''-Carboxyproprionate)))-2"-methyl-6"E-trimethylsilylmethylenecyclohexyl)ethyl]-2,5,5-trimethyl-1,3-dioxane (41)

To a solution of diisopropylamine (308 μL, 2.2 mmol) in dry THF (4 mL) under argon at 0° C. was added n-buli (2.2 mmol, 1.42 mL of 1.55M solution in hexane). The resulting solution was stirred at 0° C. for 15 min and then cooled to −78° C. The acid 10 (396 mg, 1.00 mmol) in dry THF (2 mL) was added via syringe and the resulting solution allowed to warm to ambient temperature over a 30-min period. The solution was heated to 50° C. for 2 h and then cooled to −78° C.. Next, t-butyl bromoacetate (323 μL, 2 mmol) was added and the resulting solution stirred at 0° C. for 1 h and at ambient temperature for 30 min. The solution was treated with aq. $NH_4$ (10 mL), extracted with EtOAc (3×200 mL) and dried over $MgSO_4$, and evaporated to furnish 711 mg of crude product. This was applied to a column of 80 g of silica gel 60 (230–400 mesh), eluting with (1% HOAc/EtOAc):hexane (20:80) to give product 41 (388 mg, 76%).

NMR (400 MHz): δ 0.098 (s, 9H), 0.82 (s, 3H), 0.91 (d, J=6.8 Hz, 3H), 0.99 (s, 3H), 1.30 (s, 3H), 1.39 (s, 9H), 2.10 (m, 1H), 2.30 (m, 1H), 2.48 (d, J=3.5 Hz, 1H), 2.50 (s, 1H), 3.36 (m, 2H), 3.51 (m, 2H), 5.28 (s, 1H). IR ($CDCl_3$): 1725, 1710 $cm^{-1}$. EIMS: m/e 510 (M+), 495, 476, 474, 454, 439, 437. Exact mass. calcd. for $C_{28}H_{50}SiO_6$: 510.338. Found: 510.340.

EXAMPLE 7

Preparation of 9-Alkylartemisinin Analogs

Method A: Alkylation to Cyclohexylacetic Acids 102–107, 119 and subsequent ozone addition/acid closure To a solution of two equivalents of lithium diisopropylamide ∼0.5M in THF at 0° C. was added a solution of acid 10 ∼0.5M in THF. The resultant solution was allowed to warm to ambient temperature, then warmed to 65° C. for 2 h, allowed to cool to ambient temperature and treated with alkylating agent (1.2 equiv.). After 1 h, the solution was stirred with 10% aq. HCl and sat. aq. $NH_4$ and extracted with $CHCl_3$. The separated organic layer was washed with sat. aq. $NH_4$, dried over $Na_2SO_4$ and evaporated to afford crude acids 102–107, 119 which were routinely purified via flash column chromatography with silica gel and EtOAc/hex. These acids 102–107, 119 were each submitted to the previously described general method conditions for ozone addition and subsequent acid-catalyzed formation of tetracycles 108–112, 120.

EXAMPLE 8

Method B: Alkylation of 9-Desmethylartimisinin

To a solution of 1.1 equivalents of lithium diisopropylamide ∼0.5M in THF at −78° C. was added dropwise a solution of 9-desmethylartemisinin ∼0.5M in THF over 10 min. After 1 h at −78° C., alkylation agent (1.1 equivalents) was added. The resultant mixture was allowed to warm to 0° C. slowly, and then poured into sat aq $NH_4$ and $Et_2O$. The ethereal layer was separated, washed with sat. aq. $NH_4$, dried over $Na_2SO_4$ and evaporated to provide crude solid, which was routinely purified via flash column chromatography with silica gel and EtOAc/hex.

EXAMPLE 9

[1"S, 2"R, 5"S,3'''R]-2-[2'-(2"-Methyl-5"-(2'''-(3'''-phenylpropionic acid))-6"E-trimethylsilylmethylenecyclohexyl)ethyl]-2,5,5-trimethyl-1, 3-dioxane (119)

According to Method A, Example 7, from acid 10 (341 mg, 0.863 mmol) was obtained acid 119 as a white foam, 306 mg (73%, 78% based on recovered starting material. NMR (400 MHz, CDCl₃): δ 0.15 (s, 9H), 0.89 (s, 3H), 0.98 (d, 3H, J=7.0 Hz), 1.02 (s, 3H), 1.23–1.36 (m, 2H), 1.40 (s, 3H), 1.61–1.74 (m, 3H), 1.80–2.02 (m, 5H), 2.19 (bd, 1H, J=10.8 Hz), 2.47–2.54 (m, 1H), 2.62 (dd, 1H, J=12.1, 13.6 Hz), 2.98 (dd, 1H, J=3.3, 13.6 Hz), 3.04 (ddd, 1H, J=3.3, 11.9, 11.9 Hz), 3.40–3.49 (m, 2H), 3.59 (dd, 2H, J=1.5, 11.6 Hz), 7.14–7.28 (m, 5H). IR: 3670–2260 (broad), 2960, 2875, 1700, 1250, 870–840 (broad) cm⁻¹. EIMS: m/e (rel int) 486 (1), 194 (46), 129 (100).

EXAMPLE 10

[1″S,2″R,5″S,3‴R]-2-[2′-(2″-Methyl-5″-(2‴-octanoic acid)-6″E-trimethyl silylmethylenecyclohexyl)ethyl]-2,5,5-trimethyl-1,3-dioxane (102)

Prepared according to Method A, Example 7, from acid 10 (0.57 g or 1.44 mmol) and hexyl bromide (0.5 mL). The acid 102 was obtained as a clear glass, 568 mg or 82% yield. 1H-NMR (400 MHz, CDCl₃): δ 0.12 (s, 9H), 0.87 (t, 3H, J=7.1 Hz), 0.88 (s, 3H), 0.94 (d, 3H, J=7.1 Hz), 1.03 (s, 3H), 1.10–1.30 (m, 10H) 1.35 (s, 3H), 1.38–1.50 (m, 3H), 1.56 (br dt, 1H, J=4.2, 12.8 Hz), 1.68 (dq, 1H, J=3.5, 12.0 Hz), 1.84 (m, 1H), 1.92 (m, 1H), 2.11 (br dd, 1H, J=2.5, 10.8 Hz), 2.40 (br dd, 1H, J=3.8, 11.9 Hz), 2.72 (br ddd, 1H, J=3.0, 11.5, 11.5 Hz), 3.43 (dt, 2H, J=1.4, 11.5 Hz), 3.56 (dd, 2H, J=1.4, 11.5 Hz), 5.32 (s, 1H). IR: 3600–2500, 1700, 1600, 1450, 1380, 1250, 1220, 1130, 1100, 850 cm⁻¹. DCIMS-NH₃ (m/e): 498 (M+NH₄), 481 (M+H), 394, 377, 305. Anal. Calcd for C₂₈H₅₂SiO₄: C, 69.95; H, 10.90. Found: C, 70.16; H, 10.91.

EXAMPLE 11

[1″S,2″R,5″S,3‴R]-2-[2′-(2″-Methyl-5″-(2‴hexadecanoic acid)-6″E-trimethylsilylmethylenecyclohexyl)ethyl]-2,5,5-tri methyl-1,3-dioxane (103)

Prepared according to Method A, Example 7, from acid 10 (0.5 g or 1.26 mmol) and tetradecyl bromide (0.90 mL, 3 mmol). The acid 103 was obtained as a white foam, 491 mg or 66% yield. 1H NMR (400 MHz, CDCl₃): δ 0.12 (s, 9H), 0.88 (s, 3H), 0.88 (overlapped t, 3H), 0.94 (d, 3H, J=7.1 Hz), 1.03 (s, 3H), 1.10–1.33 (m, 23H), 1.35 (s, 3H), 1.38–1.50 (m, 3H), 1.56 (br ddd, 1H, J=3.8, 12.9, 12.9 Hz), 1.69 (dq, 1H, J=3.5, 11.4 Hz), 1.80–2.00 (m, 3H), 2.11 (br dd, 1H, J=2.5, 10.5 Hz), 2.40 (br dd, 1H, J=4.3, 11.5 Hz), 2.71 (br t, 1H, J=11.5 Hz), 3.43 (dt, 2H, J=1.2, 11.5 Hz), 3.56 (dd, 2H, J=1.2, 11.5 Hz), 5.31 (s, 1H). IR: 3500–2500, 1700, 1600, 1450, 1380, 1250, 1130, 1100, 850 cm⁻¹. DCIMS-NH₃ (m/e): 610 (M+NH₄), 593 (M+H), 524, 506, 489, 417. Anal. Calcd for C₃₆H₆₈SiO₄: C, 72.91; H, 11.56. Found: C, 72.89, H, 11.70.

EXAMPLE 12

[1′S,2″R,5″S,3‴R]-2-[2′-(2″-Methyl-5″-(2‴-(8‴-t-butyldimethylsilyloxy octanoic acid)-6″E-trimethylsilylmethylenecyclohexyl)ethyl]-2,5,5-trimethyl-1,3- dioxane (104)

Prepared according to Method A, Example 7, from acid 10 (800 mg, 2.02 mmol) and 6-bromo-1-t-butyldimethylsilyloxyoctane (2 mL, 6 mmol). The acid 104 was obtained as a thick glass, 330 mg or 27% yield (large amounts of desilylation occurred). 1H NMR (400 MHz, CDCl₃): δ 0.05 (s, 6H), 0.12 (s, 9H), 0.88 (s, 3H), 0.89 (s, 9H), 0.94 (d, J=7.0 Hz, 3H), 1.03 (s, 3H), 1.10–1.30 (m, 8H), 1.35 (s, 3H), 1.68 (dq. 1H, J=4.0, 12.0 Hz), 1.89 (m, 3H), 2.12 (dd, 1H, J=2.8, 11.0 Hz), 2.40 (br dd, 1H, J=4.0, 12.0 Hz), 2.72 (br t, 1H, J=12.0 Hz), 3.30–3.70 (m, 6H), 5.31 (s, 1H). DCIMS-NH₃ (m/e): 611 (M+H), 525, 507, 455, 435, 389.

EXAMPLE 13

[1″S,2″R,5″S,3‴R]-2-[2′-(2″-methyl-5″-(2‴-(3‴-methylbutanoicacid))-6″E-trimethylsilylmethylenecyclohexyl)-ethyl]-2,5,5-trimethyl-1,3-dioxane (105)

Prepared according to Method A, Example 7, from acid 10 (579 mg or 1.46 mmol) and isopropyl iodide (0.5 mL, 5 mmol). The acid 105 was obtained as a white foam, 346 mg or 54% yield. 1H NMR (400 MHz, CDCl₃): δ 0.12 (s, 9H), 0.89 (s, 3H), 0.95 (t, 6H, J=6.8 Hz), 1.00 (d, 3H, J=7.1 Hz), 1.03 (s, 3H), 1.38 (s, 3H), 1.49 (m, 1H), 1.60 (m, 1H), 1.68 (m, 1H), 1.88 (m, 6H), 2.09 (br dd, 1H, J=2.7, 10.6 Hz), 2.65 (br d, 1H, J=12.0 Hz), 2.79 (br dd, 1H, J=2.7, 10.6 Hz), 3.43 (m, 2H), 3.56 (d, 2H, J=11.0 Hz), 5.41 (s, 1H). IR: 3500,−2500, 1700, 1600, 1460, 1380, 1250, 1220, 1100, 850, 750 cm⁻¹. DCIMS-NH₃ (m/e): 511 (M+TMS), 456 (M+NH₄), 439 (M+H), 370, 352, 335. Anal. Calcd for C₂₅H₄₆SiO₄: C, 68.44; H, 10.57. Found: C, 68.75; H, 10.44.

EXAMPLE 14

[1″S,2″R,5″S,3‴R]-2-[2′-[2″-Methyl-5″-(2‴-(5‴-phenylpentanoic acid))-6″E-trimethylsilylmethylenecyclohexyl)ethyl]-2,5,5-trimethyl-1, 3-dioxane (106)

Prepared according to Method A, Example 7, from acid 10 (0.55 g or 1.39 mmol) and 1-bromo-3-phenylpropane (0.5 mL). The acid 106 was obtained as a foam, 394 mg or 55% yield. 1H NMR (400 MHz, CDCl₃); δ 0.098 (s, 9H), 0.87 (s, 3H), 0.93 (d, 3H, J=7.1 Hz), 1.02 (s, 3H), 1.37 (m, 2H), 1.40–2.00 (m, 12H), 2.08 (br dd, 1H, J=2.8, 11.5 Hz), 2.39 (br dd, 1H, J=4.8, 12.0 Hz), 2.59 (br t, 2H, J=6.8 Hz), 2.74 (br t, 1H, J=11.5 Hz), 3.41 (br dt, 2H, J=1.4, 11.0 Hz), 3.55 (dd, 2H, J=3.1, 11.5 Hz), 5.29 (s, 1H), 7.10–7.30 (m, 5H). IR: 3600–2400, 1700, 1600, 1450, 1380, 1250, 1220, 1130, 1100, 850, 750, 710 cm⁻¹. DCIMS-NH₃ (m/e): 587 (M+TMS), 515 (M+H), 446, 428, 411, 359, 339. Anal. Calcd for C₃₁H₅₀SiO₄: C, 72.32; H, 9.79. Found: C, 72.68; H, 9.77.

EXAMPLE 15

[1″S,2″R,5″S,3‴R]-2-[2′-(2″-methyl-5″-(2‴-(5‴-methylhexanoic acid))-6″E-trimethylsilylmethylene-cyclohexyl)ethyl]-2,5,5-trimethyl-1,3-dioxane (107)

Prepared according to Method A, Example 7, from acid 10 (0.55 g or 1.39 mmol) and isoamyl bromide (0.4 mL). The acid 107 was obtained as a clear glass, 578 mg or 89% yield. 1H NMR (400 MHz, CDCl₃): δ 0.124 (s, 9H), 0.85 (dd, 6H, J=2.8, 6.6 Hz), 0.89 (s, 3H), 0.94 (d, 3H, J=7.0 Hz), 1.03 (s, 3H), 1.05–1.30 (m, 5H), 1.35 (s, 3H), 1.38–2.00 (m, 9H), 2.12 (br dd, 1H, J=2.5, 10.5 Hz), 2.41 (br dd, 1H, J=4.0, 11.7 Hz), 2.67 (ddd, 1H, J=3.0, 11.7, 11.7 Hz), 3.43 (br dt, 2H, J=1.5, 9.7 Hz), 3.55 (br d, 2H, J=11.5 Hz), 5.33 (s, 1H). IR: 3500–2400, 1700, 1600, 1460, 1380, 1270, 1250, 1220, 1130, 1100, 850, 750 cm⁻¹. DCIMS-NH₃ (m/e): 539 (M+TMS), 467 (M+H), 380, 363, 291. Anal. Calcd for C₂₇H₅₀SiO₄: C, 69.48; H, 10.80. Found: C, 69.91; H, 10.81.

EXAMPLE 16

(+)-Octahydro-3,6-dimethyl-3,12-epoxy-9-hexyl-12H-pyrano[4.3-j]-1,2-benzo dioxepin-10(3H)-one (108)

Prepared according to Method A, Example 7, from acid 102 (0.54 g or 1.12 mmol). The peroxide 108, 84.5 mg or 22% yield, was obtained as a white solid which was recrystallized from cold hexane, m.p. 80.5°–82° C. $[\alpha]_D^{21} = +44.5$ (c=0.40, CDCl$_3$). 1H NMR (400 MHz, CDCl$_3$): 0.89 (br t, 3H, J=6.9 Hz), 1.00 (d, 3H, J=5.9 Hz), 1.08 (m, 1H), 1.25-1.44 (m, 9H), 1.45 (s, 3H), 1.80 (m, 3H), 2.04 (m, 3H), 2.43 (ddd, 1H, J=3.7, 13.1, 14.6 Hz), 3.20 (m, H), 5.86 (s, 1H). IR (CHCl$_3$): 1740, 1380, 1190, 1120, 1040, 1010, 890, 840 cm$^{-1}$. DCIMS-NH$_3$ (m/e): 370 (M+NH$_4$), 353 (M+H), 335, 317, 307, 289, 279. Anal. Calcd for C$_{20}$H$_{32}$O$_5$: C, 68.15; H, 9.15. Found: C, 68.30; H, 9.31.

EXAMPLE 17

(+)-Octahydro-3,6-dimethyl-3,12-epoxy-9-tetradecyl-12H-pyrano [4.3-j]-1,2-benzodioxepin-10(3H)-one (109)

Prepared according to Method A, Example 7, from acid 103 (480 mg or 0.809 mmol). The peroxide 109, 113 mg or 30% yield, was obtained as white platelets which were recrystallized from hexane, m.p. 65°–66° C. $[\alpha]_D^{22} = +45.7$ (c=0.56, CDCl$_3$). 1H NMR (400 MHz, CDCl$_3$): 0.89 (t, 3H, J=7.0 Hz), 1.00 (d, 3H, J=6.0 Hz), 1.08 (m, 1H), 1.20–1.43 (m, 23H), 1.45 (s, 3H), 1.80 (m, 3H), 2.04 (m, 3H), 2.43 (ddd, 1H, J=3.8, 13.0, 14.7 Hz), 3.19 (m, 1H), 5.85 (s, 1H). IR (CHCl$_3$): 1735, 1380, 1185, 1120, 1040, 1010, 890, 840 cm$^{-1}$. DCIMS-NH$_3$ (m/e): 482 (M+NH$_4$), 465 (M+H), 447, 436, 419, 391. Anal. Calcd for C$_{28}$H$_{48}$O$_5$: C, 72.37; H, 10.41. Found: C, 72.27; H, 10.64.

EXAMPLE 18

(+)-Octahydro-3,6-dimethyl-3,12-epoxy-9-(1'-methyl)ethyl-12H-pyrano[4.3-j]-1,2-benzodioxepin-10(3H)-one (110)

Prepared according to Method A, Example 7, from acid 105 (250 mg or 0.57 mmol). The peroxide 110, 30 mg or 17% yield, was obtained as a white crystalline solid which was recrystallized from hexane, m.p. 113°–114° C. $[\alpha]_D^{22} = +85.0°$ (c=0.20, CH$_2$Cl$_2$). 1H NMR (400 MHz, CDCl$_3$): 0.95 (d, 3H, J=6.8 Hz), 1.01 (d, 3H, J=5.9 Hz), 1.10-1.20 (m, 2H), 1.21 (d, 3H, J=6.5 Hz), 1.35-1.52 (m, 2H), 1.46 (s, 3H), 1.75 (ddd, 1H, J=3.3, 6.4, 13.2 Hz), 1.84 (ddd, 1H, J=3.6, 6.6, 13.5 Hz), 1.92 (ddd, 1H, J=4.4, 4.4, 13.1 Hz), 2.04 (m, 3H), 2.43 (ddd, 1H, J=4.0, 14.4, 16.0 Hz), 2.97 (dd, 1H, J=4.7, 8.8 1H), 5.84 (s, 1H). IR (CHCl$_3$): 1740, 1385, 1185, 1115, 1040, 1015, 975, 890, 845 cm$^{-1}$. DCIMS-NH$_3$ (m/e): 328 (M+NH$_3$), 311 (M+H), 293, 275, 265, 247, 237, 219. Anal. Calcd for C$_{17}$H$_{26}$O$_5$: C, 65.78; H, 8.44. Found: C, 65.63; H, 8.47.

EXAMPLE 19

(+)-Octahydro-3,6-dimethyl-3,12-epoxy-9-(3'-phenyl)-propyl-12 H- pyrano[4.3-j]-1,2-benzodioxepin-10(3H)-one (111)

Prepared according to Method A, Example 7, from acid 106 (380 mg or 0.74 mmol). The peroxide 111 was obtained as a white solid, 101 mg or 35% yield, which was recrystallized from ether/hexane, m.p. 137°–138° C. $[\alpha]_D^{22} = +34.8°$ (c=0.617, CDCl$_3$). 1H NMR (400 MHz, CDCl$_3$): δ 0.99 (d, 3H, J=5.9 Hz), 1.05 (m, 1H), 1.20–1.50 (m, 4H), 1.45 (s, 3H), 1.50-1.20 (m, 10H), 2.43 (m, 1H), 2.60 (m, 1H), 2.70 (m, 1H), 3.23 (m, 1H), 5.85 (s, 1H), 7.10–7.35 (m, 5H). IR (CH$_2$Cl$_2$): 1740, 1200, 1120, 1040, 1010, 890, 840 cm$^{-1}$. DCIMS-NH$_3$ (m/e): 404 (M+NH$_4$), 387 (M+H), 369, 351, 341, 323, 313. Anal. Calcd for C$_{23}$H$_{30}$O$_5$: C, 71.48; H, 7.82. Found: C, 71.47; H, 7.78.

EXAMPLE 20

(+)-Octahydro-9β-benzyl-3,6-dimethyl-3,12-epoxy-12H-pyrano [4.3-j]-1,2- benzodioxepin-10(3H)-one (120; 16-phenylartemisinin)

According to the general method of the preceding example, acid 119 (146 mg, 0.300 mmol) was converted to the desired tetracycle and purified via flash column chromatography with silica gel and EtOAc/hexane to give 28 mg (26%) of 120 as white crystals, mp 63°–64° C. $[\alpha]_D^{22} = +29.5$ (c=0.880, CHCl$_3$). NMR (400 MHz, CDCl$_3$): δ 0.84–0.93 (m, 1H), 0.95 (d, 3H, J=6.3 Hz), 1.16 (ddd, 1H, J=3.3, 13.4 13.4 Hz), 1.23–1.32 (m, 2H), 1.35-1.51 (m, 5H), 1.53-1.62 (m, 6H), 1.73 (dq. 1H, J=3.6, 13.7 Hz), 1.91–2.01 (m, 2H), 2.04 (ddd, 1H, J=2.9, 4.8, 14.6 Hz), 2.39 (ddd, 1H, J=4.0, 13.2, 14.7 Hz), 2.61 (dd, 1H, J=11.3, 14.7 Hz), 3.57 (dd, 1H, J=4.8, 14.5 Hz), 3.65 (dt, 1H, J=4.8, 11.3 Hz), 5.88, (s, 1H), 7.18–7.34 (m, 5H). IR (CHCl$_3$): 1737, 1118, 1040, 1005 cm$^{-1}$. CIMS (NH$_4^+$): m/e (rel int) 376 (M+ + NH$_4$+, 35), 359 (M+ + H$^+$, 40), 343 (42), 323 (51), 313 (50), 285 (100). Anal. Calcd for C$_{21}$H$_{26}$O$_5$: C, 70.37; H, 7.31. Found: C, 70.52; H, 7.21.

EXAMPLE 21

(+)-Octahydro-3,6-dimethyl-3,12-epoxy-9-(3-methylbutyl)-12H-pyrano[4.3-j]-1,2-benzodioxepin-10(3H)-one (112)

Prepared according to Method A, Example 7. From acid 107 (566 mg, 1.21 mmol) was obtained 150 mg (37%) of white crystals, which recrystallized from EtOAc/hexane in successive crops to provide analytically pure white fluffy crystals, mp 117°–118° C. $[\alpha]_D^{20} = +56.4$ (c=0.525, CHCl$_3$). NMR (400 MHz, CDCl$_3$): δ 0.91 (ABt, 6H, J=11.8 Hz, CH(CH$_3$)$_2$), 1.01 (d, 3H, J=5.9 Hz, 6-CH$_3$), 1.04-1.18 (m, 3H, 1.23-1.44 (m, 4H), 1.45 (s, 3H, 3-CH$_3$), 1.48-1.63 (m, 2H), 1.75-1.86 (m, 3H), 1.97-2.12 (m, 3H), 2.44 (ddd, 1H, J=4.3, 13.3, 14.6 Hz), 3.17 (dt, 1H, J=5.2, 9.0 Hz), 5.86 (s, 1H, H12). IR (CH$_2$Cl$_2$): 2960, 2882, 1740, 1385, 1190, 1120, 1045, 1010 cm$^{-1}$. CIMS (NH$_3$): m/e (rel int) 356 (M+NH$_4^+$, 32), 339 (M+H$^+$, 63), 321 (60), 293 (50), 265 (100). Anal. Calcd. for C$_{19}$H$_{30}$O$_5$: C, 67.43; H, 8.93. Found C, 67.49; H, 8.85.

EXAMPLE 22

(+)-Octahydro-9-allyl-3,6-dimethyl-3,12-epoxy-12H-pyrano [4.3-j]-1,2-benzodioxepin-10(3H)-one (16-Vinylartemisinin)

According to Method B, Example 8, from 9-desmethylartemisinin (100 mg, 0.37 mmol) and allyl bromide (1.5 equiv) was obtained desired material as white hexagonal plates, 57 mg (50%) mp 132.5°–133° C., along with recovered starting material (24%). $[\alpha]_D^{22} = +81.2°$ (c=0.505, CHCl$_3$). NMR (400 MHz, CDCl$_3$); δ 1.00 (d, 3H, J=5.1 Hz), 1.05-1.19 (m, 1H), 1.36-1.51 (m, 5H), 1.51-1.59 (m, 2H), 1.63-1.73 (m, 2H), 1.82 (ddd, 1H, J=0.91, 4.2, 14.5 Hz), 1.91–2.01 (m, 1H), 2.08 (ddd, 1H, J=2.8, 4.4, 14.6 Hz), 2.20 (ddd, 1H, J=1.2, 4.2, 10.6 Hz), 2.36-2.55 (m, 2H), 2.90 (dddd, 1H, J=1.5, 1.5, 4.2, 11.2 Hz), 5.10–5.17 (m, 2H), 5.78 (dddd, 1H, J=5.5, 8.2, 8.8, 10.1 Hz), 5.94 (s, 1H). IR (CH$_2$Cl$_2$): 1735, 1115, 1040, 1003 cm$^{-1}$. DCIMS (NH$_3$): m/e (rel int) 326 (M+NH$_4$$^+$, 100), 309 (M+H, 77), 291 (45), 235 (33). Anal. Calcd for C$_{17}$H$_{24}$O$_5$: C, 66.21; H, 7.84. Found: C, 66.06; H, 7.89.

EXAMPLE 23

General Procedure for the Preparation of Amides 37

To a solution of acid 10a ~ 0.05M in CH$_2$Cl$_2$ was added triethylamine (2.2 equiv.). After cooling to 0° C., ethyl chloroformate (1.1 equiv.) was added dropwise. After 15 min at 0° C., amine (1.5 equiv.) was added and the resultant mixture allowed to warm to ambient temperature. After 1 h, the solution was stirred with 10% HCl:sat. aq. NH$_4$ (1:15, v:v), separated, dried over K$_2$CO$_3$, and concentrated under reduced pressure to provide crude amides 37.

EXAMPLE 23A: [1″S,3″S,5″R]-2′-[3″-(2″′-(N-Propyl 2″″-acetamide))-6″-methyl-2″Z-trimethylsilylmethylenecyclohexyl]ethyl-2,5,5-trimethyl-1,3-dioxane (37b)

Obtained from acid 10a (209 mg, 0.583 mmol) and n-propylamine (freshly distilled, 72 )µL, 1.5 equiv.) according to the general procedure as a yellow oil, 206 mg (81%), which was used without further purification. An analytical sample was prepared via flash column chromatography with silica gel and EtOAc/hex. $[\alpha]_D^{22}$ = +39.9 (c=5.17, CH$_2$Cl$_2$). NMR (400 MHz, CDCl$_3$): 0.08 (s, 9H), 0.86 (s, 3H), 0.88–0.98 (m, 6H), 1.09 (s, 3H), 1.39 (s, 3H), 1.40–1.51 (m, 3H), 1.60–1.75 (m, 8H), 2.11–2.17 (br m, 1H), 2.26 (dd, 1H, J=6.4, 13.6 Hz, 2.44 (dd, 1H, J=9.2, 13.6 Hz), 2.83–2.91 (br m, 1H), 3.09–3.25 (m, 2H), 3.41 (dt, 2H, J=1.9, 11.4 Hz), 3.62 (dd, 2H, J=5.0, 11.4 Hz), 5.42 (s, 1H), 6.06 (br s, 1H, NH). IR: 3300, 2980, 2965, 2880, 1655, 1255, 860, 750 cm$^{-1}$). EIMS: m/e (rel int) 437(10), 422(21), 281(78), 129(83), 73(100). Anal. Calcd. for C$_{25}$H$_{47}$NO$_3$Si: C, 68.60; H, 10.82; N, 3.20. Found: C, 68.86; H, 11.11; N, 3.02.

Example 23B: [1″S,3″S,5″R]-2′-[3″-(2″′-(N-Benzyl 2″″-acetamide))-6″-methyl-2″Z-trimethylsilylmethylenecyclohexyl]ethyl-2,5,5-trimethyl-1,3-dioxane (37c)

Obtained from acid 10a (663 mg, 1.85 mmol) and benzylamine (304 )µL, 1.5 equiv.) according to the general procedure as a pale yellow oil, 854 mg (95%). $[\alpha]_D^{22}$ = +73.9 (c=2.90, CH$_2$Cl$_2$). NMR (400 MHz, CDCl$_3$): δ 0.09 (s, 9H), 0.78 (s,3H), 0.94 (d, 3H, J=6.9 Hz), 1.05 (s, 3H, 1.09–1.23 (m, 4H), 1.44 (br d, 1H, J=13.3 Hz), 1.56–2.01 (m, 7H), 2.12–2.18 (m, 1H), 2.31 (dd, 1H, J=6.0, 13.7 Hz), 2.50–2.64 (m, 1H), 2.90–2.98 (br m, 1H), 3.23 (dd, 1H, J=1.8, 11.2 Hz), 3.34 (dd, 1H, J=1.7, 11.4 Hz), 3.40 (d, 1H, J=11.4 Hz), 3.54 (d, 1H, J=11.4 Hz), 4.37 (ddd, 1H, J=5.3, 14.6, 14.6 Hz), 4.42 (ddd, 1H, J=5.3, 14.6, 14.6 Hz), 5.47 (s, 1H), 6.52 (br m, 1H), 7.22–7.36 (m, 5H). IR (CH$_2$Cl$_2$): 3450, 3330, 2960, 2875, 1660, 1510, 1460, 1380, 1218, 1117, 1088, 933, 860 cm$^{-1}$. EIMS: m/e (rel int) 485(13), 470(20), 329(88), 91(100). Anal. Calcd for C$_{29}$H$_{47}$NO$_3$Si: C, 71.71; H, 9.75; N, 2.88. Found: C, 71.58; H, 9.85; N, 2.72.

Example 23C: [1″S,3″S,5″R]-2′-[3″-(2″′-(N-t-Butyl 2″″-acetate))acetamide-6″-methyl-2″Z-trimethylsilylmethylene cyclohexyl]ethyl-2,5,5-trimethyl-1,3-dioxane (37d)

Obtained from acid 10a (889 mg, 2.48 mmol) and glycine t-butyl ester (0.560 g, 4.27 mmol) according to the general procedure. Flash column chromatography with silica gel and EtOAc/hexane provided the desired amide as a white foam, 857 mg (68%). $[\alpha]_D^{22}$ = +40.3 (c=16.2, CH$_2$Cl$_2$). NMR (400 MHz, CDCl$_3$): δ 0.08 (s, 9H), 0.87 (s,3H), 0.93 (d, J=7.0 Hz), 1.07 (s,3H), 1.12–1.20 (br m, 1H), 1.37 (s, 3H), 1.47 (s, 9H), 1.56–1.94 (m, 8H), 2.15 (br t, 1H, J=6.9 Hz), 2.39 (dd, 1H, J=8.1, 13.9 Hz), 2.46 (dd, 1H, J=8.1, 13.9 Hz), 2.82–2.90 br m, 1H), 3.44 (ddd, 2H, J=1.6, 6.3 11.5 Hz), 3.60 (d, 2H, J=11.5 Hz), 3.79 (dd, 1H, J=4.7, 18.3 Hz), 4.01 (dd, 1H, J=4.7, 18.3 Hz), 5.42 (s, 1H), 6.33 (br m, 1H). IR: 3310, 2950, 2870, 1745, 1655, 1605, 1525, 1455, 1370, 1250, 1165, 1120, 1090, 1043, 917, 855, 735 cm$^{-1}$. EIMS: m/e (rel int) 509(7), 494(10), 438(11), 366(10), 353(42), 297(42), 129(100). Anal. Calcd for C$_{28}$H$_{51}$NO$_5$Si: C, 65.97; H, 10.08; N, 2.75. Found: C, 65.57; H, 10.31; N, 2.76.

Example 23D: [1″S,3″S,5″R]-2′-[3″-(2″′-(N-(N′,N′-Dimethylaminoethyl)acetamide))-6″-methyl-2″Z-trimethylsilylmethylenecyclohexyl]ethyl-2,5,5-trime thyl-1,3-dioxane (37f)

Obtained from acid 10a (977 mg, 2.73 mmol) and N,N-dimethylethylenediamine (0.33 mL, 300 mmol) according to the general procedure, except with final alkaline workup (sat. aq. NaHCO$_3$). After flash chromatography with silica gel and 0.5% (58% NH$_4$OH)/5% MeOH/CH$_2$Cl$_2$ was afforded a colorless oil, 900 mg (71%). NMR (400 MHz, CDCl$_3$): δ 0.09 (s, 9H), 0.88 (s, 3H), 0.89–1.05 (m, 6H), 1.06 (s, 3H), 1.45–1.95 (m, 7H), 2.00–2.17 (m, 1H), 2.23 (s, 6H), 2.36 (m, 3H), 3.31 (ddd, 2H, J=5.9, 5.9, 13.0 Hz), 3.43 (d, 2H, J=10.8 Hz), 3.58 (d, 2H, J=10.8 Hz), 5.41 (s, 1H), 6.19 (br m, 1H). IR: 3300, 2960, 2820, 2860, 2770, 1645, 1605, 1550, 1465, 1380, 1253, 1220, 1200, 1120, 1100, 1045, 855 cm$^{-1}$. EIMS: m/e (rel int) 466(1), 396(6), 129(10), 71(70), 58(100). Anal. Calcd for C$_{26}$H$_{50}$O$_3$N$_2$Si: C, 66.90; H, 10.80; N, 6.00. Found: C, 66.59; H, 11.00; N, 5.78.

EXAMPLE 24

General procedure for the preparation of 11-Azaartemisinin Analogs 16

Through a solution of amide in CH$_2$Cl$_2$ (0.04–0.05M) at −78° C. was passed a stream of O$_3$/O$_2$ until a blue color was obtained. Careful monitoring by TLC was routine to gauge the conversion of starting material and minimize overexposure to O$_3$. The resultant mixture was then treated in succession with a solution of BHT (10 mg) in CH$_2$Cl$_2$ (1 mL), silica gel 60 (0.5 wt.: vol. CH$_2$Cl$_2$) and 3M H$_2$SO$_4$ (0.5 vol.: wt. silica gel 60) and allowed to warm to ambient temperature. After 2 days or more, the solid was filtered off and rinsed with CH$_2$Cl$_2$ (2×) and EtOAc (1×). The filtrate was washed over sat. aq. NaHCO$_3$ (2×) and brine (1×), dried over MgSO$_4$ and evaporated under reduced pressure to afford crude product.

Example 24A:
(−)-Octahydro-3,6-dimethyl-3,12-epoxy-11-propyl-12H-pyridino[4.3-j]-1,2-benzodioxepin-10(3H)-one (16b)

Prepared according to the general procedure from amide 37b (206 mg, 0.471 mmol). Purification via flash column chromatography with silica gel and EtOAc/hex and recrystallization from EtOAc/hex afforded white needles, 52 mg (24%), mp 125.0°–125.5° C. $[\alpha]_D^{22} = -15.7$ (c=0.890, CHCl$_3$). 1H NMR (400 MHz, CDCl$_3$): 0.93 (t, 3H, J=7.4 Hz), 1.01 (d, 3H, J=6.2 Hz), 1.04–1.16 (m, 1H), 1.20–1.37 (m, 2H), 1.39 (s, 3H), 1.40–1.79 (m, 7H), 1.95–2.07 (m, 2H), 2.12 (dd, 1H, J=1.3, 17.4 Hz), 2.37–2.47 (m, 1H), 3.14 (dd, 1H, J=6.0, 17.5 Hz), 3.41 (ddd, 1H, J=5.3, 10.0, 13.2 Hz), 3.58 (ddd, 1H, J=6.1, 10.0, 13.2 Hz), 5.28 (s, 1H). IR (CH$_2$Cl$_2$): 2940, 1640, 1065, 1045 cm$^{-1}$. CIMS (NH$_3$): m/e (rel int) 327 (M+NH$_4^+$, 12), 310 (M+H$^+$, 100). Anal. Calcd for C$_{17}$H$_{27}$NO$_4$: C, 65.99; H, 8.80; N, 4.53. Found: C, 65.72; H, 8.83; N, 4.32.

Example 24B:
(−)-Octahydro-11-benzyl-3,6-dimethyl-3,12-epoxy-12H-pyridino[4.3-j]-1,2-benzodioxepin-10(3H)-one (16c)

Prepared according to the general procedure from amide 37c (130 mg, 0.268 mmol). Flash column chromatography with silica gel and EtOAc/hexane afforded 24 mg (25%) white crystals, which recrystallized from EtOAc/hexane, mp 177°–179° C. $[\alpha]_D^{22} = -3.0$ (c=0.500, CH$_2$Cl$_2$). NMR (400 MHz, CDCl$_3$): δ 0.94 (d, 3H, J=6.2 Hz), 0.97–1.12 (m, 1H), 1.15 (s, 3H), 1.17–1.47 (m, 4H), 1.57–1.69 (m, 3H), 1.75–1.82 (m, 1H), 1.89–2.01 (m, 2H), 2.22 (dd, 1H, J=1.4, 17.6 Hz), 2.33–2.42 (m, 1H), 4.60 (d, 1H, J=14.6 Hz), 5.06 (d, 1H, J=14.6 Hz), 5.14 (s, 1H), 7.19–7.39 (m, 5H). IR (CH$_2$Cl$_2$): 2940, 1643, 1135, 1080, 1027, 917 cm$^{-1}$. CIMS (NH$_3$): m/e (rel int) 375 (M+NH$_4^+$, 5), 358 (M+H$^+$, 100). Anal. Calcd for C$_{21}$H$_{27}$NO$_4$: C, 70.56; H, 7.61; N, 3.92. Found: C, 70.87; H, 7.56; N, 3.81.

Example 24C:
(−)-Octahydro-11-(2′-(t-butylacetate))-3,6-dimethyl-3,12-epoxy-12H-pyridino[4.3-j]-1,2-benzodioxepin-10(3H-one (16d)

Preparing according to the general procedure from amide 37d (725 mg, 1.51 mmol). After successive flash column chromatography with silica gel and EtOAc/hexane and EtOAc/CH$_2$Cl$_2$, respectively, was obtained 202 mg (35%) of yellow solid, which was recrystallized from EtOAc/hexane to provide pale yellow hexagonal plates, mp 116°–117° C. $[\alpha]_D^{22} = -13.3$ (c=9.55, CH$_2$Cl$_2$). NMR (400 MHz, CDCl$_3$): δ 1.00 (d, 3H, J=6.3 Hz), 1.02–1.16 (m, 1H), 1.30–1.42 (m, 4H), 1.43–1.56 (m, 15H), w 1.63–1.84 (m, 4H), 1.94–2.07 (m, 2H), 2.18 (dd, 1H, J=1.3, 17.4 Hz), 2.38–2.48 (m, 1H), 3.16 (dd, 1H, J=5.9, 17.4 Hz), 3.94 (d, 1H, J=17.4 Hz), 4.52 (d, 1H, J=17.4 Hz), 5.43 (s, 1H). IR (CH$_2$Cl$_2$): 2930, 1735, 1650, 1367, 1227, 1160, 1135, 1035 cm$^{-1}$. CIMS (NH$_4^+$): m/e (rel int) 399 (M+NH$_4^+$, 7), 382 (M+H$^+$, 30), 326 (100). Anal. Calcd for C$_{20}$H$_{31}$NO$_6$: C, 62.90; H, 8.19; N, 3.67. Found: C, 63.23; H, 8.19; N, 3.63.

Example 24D:
(−)-Octahydro-11-(2′-acetic acid)-3,6-dimethyl-3,12-epoxy-12H-pyridino[4.3-j]-1,2-benzodioxepin-10 (3H)-one (16e)

To a solution of t-butyl ester 16d (135 mg, 0.354 mmol) in CH$_2$Cl$_2$ (10 mL) was added TFA (0.50 mL). After 3 h at ambient temperature, the resultant solution was washed with H$_2$O (4×20 mL) and brine (25 mL), dried over Na$_2$SO$_4$ and concentrated under reduced pressure to a white solid, which recrystallized from EtOAc/hexane to provide 47 mg (41%) of white cubic prisms, mp 169°–172° C. (d), in successive crops. $[\alpha]_D^{22} = -26$ (c=0.730, CHCl$_3$). NMR (400 MHz, CDCl$_3$): δ 1.05 (d, 3H, J=6.2 Hz), 1.07 (dd, 1H, J=3.7, 12.8 Hz), 1.14 (dd, 1H, J=3.7, 12.8 Hz), 1.38 (s, 3H), 1.39–1.61 (m, 3H), 1.68 (ddd, 1H, J=3.1, 6.9, 13.6 Hz), 1.72 (ddd, 1H, J=3.1, 6.9, 13.6 Hz), 1.83 (br dt, 1H, J=4.5, 13.7 Hz), 1.95–2.08 (m, 2H), 2.21 (dd, 1H, J=1.2, 17.6 Hz), 2.43 (ddd, 1H, J=3.6, 14.3, 14.6 Hz), 3.19 (dd, 1H, J=6.2, 17.5 Hz), 4.21 (d, 1H, J=17.4 Hz), 4.52 (d, 1H, J=17.4 Hz), 5.39 (s, 1H). IR (CHCl$_3$): 3500–2150 (br, O-H), 2945, 1725, 1648, 1265–1165, 1138, 1038 cm$^{-1}$. CIMS (NH$_3$): m/e (rel int) 343 (M+NH$_4^+$, 5), 326 (M+H$^+$, 100), 240 (50). Anal. Calcd for C$_{16}$H$_{23}$NO$_6$: C, 59.07; H, 7.13; N, 4.30. Found: C, 59.42; H, 7.32; N, 4.33.

Example 24E:
(−)-Octahydro-3,16-dimethyl-11-(2′-dimethylaminoethyl-3,12-epoxy-12H-pyridino[4.3-j]-1,2-benzodioxepin-10(3H)-one (16f)

To a solution of amine 37f (600 mg, 1.29 mmol) in MeOH (40 mL) was added 10% aq. HCl (1 mL). The MeOH was removed via rotary evaporation under reduced pressure in the cold, and the resultant residue was shaken with sat. aq. NaHCO$_3$ (15 mL) and CH$_2$Cl$_2$ (35 mL). The separated organic layer was washed with sat. aq NaHCO$_3$, dried over K$_2$CO$_3$, and evaporated to a colorless oil, which was placed in MeOH (40 mL), cooled to −78° C. and a stream of O$_3$/O$_2$ was bubbled through. When the TLC monitor indicated that no starting material remained, the resultant mixture was concentrated under reduced pressure at below ambient temperature. Final traces of H$_2$O were removed azeotropically with CH$_2$Cl$_2$ (50 mL) and the resultant residue was placed in CH$_2$Cl$_2$ (40 mL) and TFA (1 mL). After 3 days at ambient temperature, the mixture was washed with sat. aq. NaHCO$_3$(2×30 mL), dried over K$_2$CO$_3$ and evaporated to afford a yellow oil, which was purified via flash column chromatography with SiO$_2$. After elution with 0.5% (58% NH$_4$OH)/5% MeOH/CH$_2$Cl$_2$, 222 mg (51%) of the title compound was obtained as a yellow oil. $[\alpha]_D^{22} = -16.4°$ (c=5.54, CH$_2$Cl$_2$).

$^1$H NMR (400 MHz, CDCl$_3$): δ 1.00 (d, 3H, J=6.2 Hz), 1.03–1.18 (m, 1H), 1.30–1.54 (m, 7H), 1.60–1.79 (m, 3H), 1.94–2.06 (m, 2H), 2.11 (dd, 1H, J=1.4, 17.4 Hz), 2.28 (s, 6H), 2.35–2.51 (m, 2H), 2.61–2.70 (m, 1H), 3.13 (dd, 1H, J=6.0, 17.4 Hz), 3.56 (quintet, 1H, J=6.8 Hz), 3.77 (ddd, 1H, J=5.1, 7.7, 13.5 Hz), 5.45 (s, 1H). 13C NMR: 167.2, 119.2, 103.3, 91.9, 78.5, 77.5, 55.6, 50.1, 44.2, 38.1, 37.6, 36.6, 35.3, 32.7, 32.4, 27.2, 23.7, 18.5. IR: 2980, 2930, 1708, 1465, 1260, 1160, 1039 cm$^{-1}$. CIMS (NH$_4^+$): m/e (rel int) 339 (M+ + NH$_4^+$, 100) 323 (M+ + H$^+$, 15), 307(18), 281(20), 240(17), 117(29). Anal. Calcd for C$_{18}$H$_{30}$N$_2$O$_3$: C, 63.88; H, 8.93; N, 8.28. Found: C, 63.95; H, 9.07; N, 8.13.

Example 24F: Hydrochloride Monohydrate Salt (16g)

To a solution of the amine 16f (68 mg, 0.211 mmol) in 95% EtOH (10 mL) was added 38% HCl (50 μL). The solvent was removed in vacuo to provide a hygroscopic tan foam, which was shown to be the monohydrate by analysis. $[\alpha]_D^{22} = -24.5°$ (c=2.69, CHCl$_3$) NMR (400 MHz): δ 1.00 (d, 3H, J=6.2 Hz), 1.03-1.17 (m, 1H), 1.21-1.53 (m, 10H), 1.60-1.84 (br m, 2H), 1.95-2.19 (m, 2H), 2.39 (br ddd, 1H, J=3.5, 9.7, 13.6 Hz), 2.77-3.00 (br m, 7H), 3.11 (dd, 1H, J=6.2, 17.7 Hz), 3.18-3.36 (m, 2H), 3.74 (ddd, 1H, J=6.3, 9.5, 13.2 Hz), 4.09-4.17 (m, 1H), 5.38 (s, 1H). IR (CHCl$_3$): 2970, 2340 (broad, NH), 1645, 1465 cm$^{-1}$. Anal. Calcd. for C$_{18}$H$_{30}$N$_2$O$_4$: C, 55.02; H, 8.47; N, 7.13. Found: C, 54.88; H, 8.24; N, 7.15.

EXAMPLE 25

(+)-Octahydro-3,6-dimethyl-7β-ethyl-3,12-epoxy-12H-pyrano [4.3-j]-1,2-benzo dioxepin-10(3H)-one (18)

A solution of 41 (270 mg, 0.529 mmol) in CH$_2$Cl$_2$ was cooled to −78° C. and treated with ozone (7 psi, 0.4 L/min, 70 V) until a faint blue color was seen (about 4 min). A solution of BHT (30 mg) in CH$_2$Cl$_2$ (1 mL) was added, followed by silica gel (7.5 g) and 3M H$_2$SO$_4$ (3 mL). The resulting mixture was brought to ambient temperature and stirred for 18 h. The silica gel was removed by filtration and rinsing with EtOAc (50 mL). The filtrate was concentrated in vacuo to afford the butyl ester 42, which was placed in CH$_2$Cl$_2$ (25 mL) and treated with trifluoroacetic acid (0.60 mL). The resultant solution was stirred at room temperature for 2 h. The solution was filtered through silica gel (15 g), rinsing with EtOAc (75 mL). The solvent was removed in vacuo, leaving 300 mg of crude product. This was adsorbed onto 2 g of silica gel and placed on top of a column of 30 g of silica gel 60 (230–400 mesh), eluting via stepwise gradient of hexane/(1% HOAc/EtOAc) from 90/10 to 60/40. After elution with 50 mL of 90/10, 100 mL of 80/20, 100 mL of 70/30, and 92 mL of 60/40, the product was collected from the next 115 mL of 60/40. Evaporation left 64 mg of product containing ~20% deoxy by NMR. This was taken into EtOAc (1 mL) and crystallized to provide 35 mg (20%) of pure product 18, mp 155°-157° C.

NMR (400 MHz): δ 0.98 (d, J=5.9 Hz, 3H), 1.43 (s, 3H), 2.36 (dd, J=7.0, 16.7 Hz, 1H), 2.42 (m, 1H), 2.98 (dd, J=7.0. 16.7 Hz), 3.85 (ddd, J=5.1, 7.0, 7.0 Hz), 5.87 (s, 1H). Anal. Calcd. for C$_{16}$H$_{22}$O$_7$: C, 58.89; H, 6.79. Found: C, 58.52; H, 6.71.

EXAMPLE 26

(1"S, 3"S, 5"R, 2"'R)-2"Z-2'-[3"-(2"'-Butyric acid)6"-methyl-2'-trimethylsilylmethylenecyclohexyl]ethyl-2,5,5-trimethyl-1,3-dioxane (36)

To a solution of diisopropylamine (635 82 L, 4.24 mmol) in dry THF (8 mL) at 0° C. was added n-BuLi (4.24 mmol, 3.01 mL of 1.55M in hexane). The resulting solution was stirred at 0° C. for 15 min and then cooled to −78° C. The acid 10 (840 mg, 2.12 mmol) in dry THF (4 mL) was added via syringe, and the solution was allowed to warm to ambient temperature over 30 min. The solution was heated to 50° C. for 2 h and recooled to 0° C. Ethyl iodide (424 )L, 5.3 mmol) was added and the resulting solution stirred at ambient temperature for 1 h. The solution was treated with aq. NH$_4$ (10 mL) and extracted with EtOAc (3×20 mL). The organic layers were dried (MgSO$_4$) and evaporated in vacuo to give 1.3 g of crude product, which was applied to a column of 25 g of silica gel 60 (230–400 mesh), eluting with (1% HOAc/EtOAc)/hexane (20/80) to give the product 36 (677 mg, 75%) as a colorless gum.

NMR (400 MHz): δ 0.09 (s, 9H, SiCH$_3$), 0.82-0.906 m, 12H), 1.00 (s, 3H), 1.50-1.90 (bm, 1H), 1.22-1.95 (m, 10H), 2.05-2.15 (m, 1H), 2.32-2.41 (m, 1H), 2.64 (ddd, 1H, J=3.1, 11.7, 11.7 Hz), 3.39 (ddd, 2H, J=1.5, 11.2, 11.2 Hz), 3.53 (d, 2H, J=11.7 Hz), 5.29 (s, 1H, =CH). EIMS: m/e (rel int) 424 (5), 194 (28), 180 (26), 161 (25), 160 (25), 129 (100). Exact mass calcd. for C$_{24}$H$_{44}$O$_4$Si: 424.301. Found 424.300.

A solution of 36 (677 mg, 1.59 mmol) in CH$_2$Cl$_2$ (100 mL) was cooled to −78° C. and treated with a stream of ozone (7 psi, 0.4 L/min, 70 V) until a faint blue color was seen (about 8 min). A solution of BHT (50 mg) in CH$_2$Cl$_2$ (1 mL) was added, followed by the addition of silica gel 60 (70–230 mesh) (16 g) at −78° C. The resulting mixture was treated with 3M H$_2$SO$_4$ (6 mL) and brought to ambient temperature and stirred overnight. The mixture was treated with NaHCO$_3$ (6 g) and stirred for 20 min at room temperature. The product was isolated by filtration, rinsing with EtOAc (100 mL). The solvent was removed in vacuo, leaving 630 mg of crude product. This was adsorbed onto 2 g of 230–400 mesh silica gel 60 and applied to a column of 30 g of silica gel 60 (230–400 mesh) eluting with hexane/EtOAc (90/10) to give the product 17 (152 mg, 32%) as a white solid, which was crystallized from hexane to provide white crystals, mp 125°-125.5° C. $[\alpha]_D^{22} = +70.0$ (c=0.10, EtOH).

NMR (400 MHz): δ 0.95 (t, 3H, J=7.5H), 0.98 (d, 3H, J=5.9 Hz), 1.43 (s, 3H), 2.04 (m, 3H), 2.40 (m, 1H), 3.09 (dt, 1H, J=5.5, 9.3 Hz), 5.83 (s, 1H). IR (CHCl$_3$): 3030, 2970, 2930, 2880, 1740, 1385, 1190, 1120, 1040, 1000, 890 cm$^{-1}$. CIMS (NH$_4^+$): m/e 314 (M+NH$_4^+$), 297 (M+H$^+$), 279, 268, 251, 233, 223. Anal. Calcd. for C$_{16}$H$_{24}$O$_5$: C, 64.84; H, 8.16. Found: C, 64.80; H, 8.21.

EXAMPLE 27 t-Butylarteperether (19)

To a solution of dihydroqinghaosu (43) (100 mg, 0.32 mmol) in CH$_2$Cl$_2$ (7 mL) under argon was added dry 4 μ molecular sieves (2.2. g), 3.0M t-BuOOH in isooctane (200 mL), and p-toluenesulfonic acid (20 μg). The mixture was stirred at 23° C. for 30 min, and solid NaHCO$_3$ (ca. 1 g) was added. After 15 min, the mixture was filtered and evaporated. PTLC on 2×1.0-mm silica gel plates, eluting with 15% EtOAc/hexane, gave pure 19 (85 mg or 68% yield), which was crystallized from cold pentane or hexane to give cubic crystals, mp 94°-95° C. $[\alpha]_D^{22} = +157$ (c=0.25, CHCl$_3$).

400 MHz 1H NMR (CDCl$_3$): δ 0.93 (d, J=67.6 Hz, 3H), 0.96 (d, J=7.5 Hz, 3H), 1.24 (s, 9H), 1.42 (s, 3H), 1.64 (dq, J=3.1, 6.5, 13.2 Hz, 1H), 1.75 (dq, J=3.5, 7.3, 13.5 Hz, 1H), 1.85 (ddq, J=3.1, 4.0, 6.8, 13.5 Hz, 1H), 2.01 (dq, J=2.9, 4.8, 14.5 Hz, 1H), 2.77 (ddq, J=4.4, 7.5, 15.2 Hz, 1H), 5.30 (d, J=4.5 Hz, 1H), 5.51 (s, 1H). IR (CDCl$_3$): 1380, 1370, 1100, 1050, 980, 960, 940 cm$^{-1}$. CIMS (NH$_3$): m/e 374 (M+NH$_4$), 311, 284, 267, 249, 239, 221. Anal. Calcd. for C$_{19}$H$_{32}$O$_6$: C, 64.02; H, 9.05. Found: C, 64.33; H, 9.35.

EXAMPLE 28

(+)-Octahydro-3,6-dimethyl-3,12-epoxy-6β-epoxy-7β-ethyl-12H-pyrano[4.3-j]-1,2-benzodioxepin-10(3H)-one (20)

A solution of 17 (132 mg, 0.445 mmol) in methanol (6 mL) at 0° C. was treated with NaBH$_4$ (132 mg, 3.49 mmol). The resulting mixture was stirred at 0° C. for 1 h. The mixture was treated with glacial acetic acid (200 μL) and water (6 mL). The resulting mixture was extracted with CH$_2$Cl$_2$ (3×30 mL) and dried (MgSO$_4$). Evaporation left lactol (129 mg, 97%) as a white solid, which was used without further purification.

A solution of lactol (129 mg, 0.432 mmol) in ethanol (1.5 mL) and benzene (4.5 mL) was treated with BF$_3$.Et$_2$O (20 μL) and then heated to 80° C. for 1 h. After cooling to room temperature, saturated aqueous NaOAc (1.5 mL) and water (1.5 mL) were added with stirring. The phases were separated and the aqueous phase extracted with benzene (2×6 mL). The combined organic phases were dried (MgSO$_4$) and evaporated, leaving 130 mg of crude product. This was applied to a column of silica gel 60 (230-400 mesh) eluting with hexane/EtOAc (90/10) to give 20 (89 mg 63%) and its C6 epimer (17 mg, 12%). Recrystallization of the 89 mg of 20 along with 11 mg from an earlier run from hexane gave 67 mg of material, mp 97°-98° C. $[\alpha]_D^{22} = +220$ (c=0.18, CHCl$_3$).

$^1$H NMR (400 MHz): δ 0.89 (t, 3H, J=7.4 Hz, CH$_2$CH$_3$), 0.96 (d, 3H, J'6.2 Hz, 10-CH$_3$), 1.18 (t, 3H, J=7.0 Hz, OCH$_3$CH$_3$), 1.21-1.43 (m, 3H), 1.45 (s, 3H, 3-CH$_3$), 1.47-1.59 (m, 2H), 1.63 (ddd, 1H, J=3.4, 7.0, 13.0 Hz), 1.69 (ddd, 1H, J=3.7, 7.7, 13.0 Hz), 1.78-1.93 (m, 2H), 2.04 (ddd, 1H, J=3.1, 4.8, 14.5 Hz), 2.3-2.43 (m, 2H), 3.48 (ddd, 1H, J=7.0, 7.0, 11.0 Hz, OCH$_2$), 3.87 (ddd, 1H, J=7.0, 7.0, 11.0 Hz), 13C NMR: 11.3, 15.2, 20.4, 20.5, 26.2, 34.7, 36.5, 37.5, 37.5, 42.7, 52.6, 63.7, 81.0, 88.2, 100.4, 104.0, 4.92 (d, 1H, J=3.5 Hz, H6), 5.43 (s, 1H, H$_{4\alpha}$). IR (KBr): 2940, 1110, 1093, 1040, 1018, 993 cm$^{-1}$. CIMS (NH$_4^+$): m/e (rel int), 344 (M+NH$_4^+$, 5), 28 (100). Anal. Calcd. for C$_{18}$H$_{30}$O$_5$: C, 66.23; H, 9.26. Found: C, 66.23; H, 9.28.

C6 Epimer: Octahydro-3,6-dimethyl-3,12-epoxy-6α-ethoxy-7β-ethyl-12H-pyrano[-4.3-j]-1,2-benzodioxepin-10(3H)-one NMR (400 MHz): δ 0.89 (t, 3H, J=7.3 Hz, CH$_2$CH$_3$), 0.97 (d, 3H, J=6.0 Hz, 10-CH$_3$), 0.99-1.22 (m, 2H), 1.22 (t, 3H, J=7.0 Hz, OCH$_2$CH$_3$), 1.25-1.38 (m, 2H), 1.45 (s, 3H, 3-CH$_3$), 1.48-1.74 (m, 4H), 1.89 (ddd, 1H, J=3.3, 6.4 16.8 Hz), 2.03 (ddd, 1H, J=3.1, 4.4, 14.8 Hz), 2.16 (ddd, 1H, J=4.1, 9.6, 14.9 Hz), 2.39 (ddd, 1H, J=4.0, 13.5, 15.2 Hz), 3.49 (ddd, 1H, J=7.0, 9.6 15.2 Hz, OCH$_2$), 4.02 (ddd, 1H, J=7.0, 9.6 15.2 Hz, OCH$_2$), 4.48 (d, 1H, J=9.3 Hz, H6), 5.35 (s, 1H, H$_{4\alpha}$).

EXAMPLE 29

(+)-Octahydro-3,6-dimethyl-10β-ethoxy-3,12-epoxy-9β-propyl-12H-pyrano[4.3-j]-1,2-benzodioxepine (90)

To a solution of (+)-octahydro-3,6-dimethyl-3,12-epoxy-7β-propyl-12H-pyrano[4.3-j]-1,2-benzodioxepin-10(3H)-one (89, 80 mg, 0.26 mmol) in MeOH (4 mL) at 0° C. was added NaBH$_4$ (80 mg, 2.1 mmol). After 1 h at 0° C., glacial acetic acid (120 μL) and H$_2$O (4 mL) was added and the mixture was extracted with CH$_2$Cl$_2$ (3×20 mL). The combined organic layers were dried over MgSO$_4$ and evaporated to provide 61 mg (75%) of lactol as a white solid, which was used without further purification.

To a solution of lactol (61 mg, 0.20 mmol) in benzene (4.5 mL) and ethanol (1.5 mL) was added boron trifluoride etherate (10 )L). The resultant solution was heated at 80° C. for 1 h, allowed to cool to ambient temperature, treated with saturated aqueous sodium acetate (1.5 mL) and H$_2$O (1.5 mL), and extracted with benzene (2×10 mL). The combined organic layers were dried over MgSO$_4$ and evaporated to give 61 mg (90.∴ crude) of white crystalline solid, which upon recrystallization afforded pure title compound as analytically pure white crystals, mp 109°-111° C. $[\alpha]_D^{20} = +79.3$ (c=0.440, CHCl$_3$). 1H NMR (400 MHz): δ 0.90 (t, 3H, J=7.1 Hz), 0.96 (d, 3H, J=6.3 Hz), 1.19 (t, 3H, J=7.1 Hz), 1.22-1.42 (m, 6H), 1.45 (s, 3H), 1.48-1.59 (m, 3H), 1.62 (ddd, 1H, J=3.3, 6.6, 13.2 Hz), 1.69 (ddd, 1H, J=4.1, 8.2, 14.1 Hz), 1.79-1.93 (m, 2H), 2.04 (ddd, 1H, J=2.9, 4.8, 14.7 Hz), 2.38 (ddd, 1H, J=4.0, 14.5, 14.6 Hz), 2.39-2.48 (brm, 1H),3.58 (dq. 1H, J=7.0, 11.3 Hz), 3.87 (dq, 1H, J=7.1, 11.3 Hz), 4.88 (d, 1H, J=3.5 Hz, H$_{10\alpha}$), 5.43 (s, 1H). 13C NMR: 14.3, 15.2, 19.8, 20.4, 24.5, 24.8, 26.3, 29.8, 34.8, 35.6, 36.5, 37.5, 42.9, 52.7, 63.7, 81.0, 88.2, 100.7, 104.0. CIMS (NH$_4^+$): m/e (rel int) 358 (M+NH$_4^+$, 13), 312 (27, 295 (100, 277 (35), 249 (68).

Also, some of the alternate 10α epimer was isolated:

EXAMPLE 30

Octahydro-3,6-dimethyl-10α-ethoxy-3,12-epoxy-9β-propyl-12H-pyrano[4.3-j]-1,2-benzodioxepine NMR (400 MHz) 0.90 (t, 3H, J=7.3 Hz, 0.96 (d, 3H, J=7.1 Hz), 1.00-1.11 (m, 3H), 1.99-1.42 (m, 7H), 1.22 (t, 3H, J=7.0 Hz), 1.45 (s, 3H), 1.47-1.73 (m, 7H), 1.89 (brm, 1H), 2.03 (ddd, 1H, J=2.9, 4.8, 14.6 Hz), 2.26 (ddd, 1H, J=5.0, 9.8, 18.4 Hz), 2.38 (ddd, 1H, J=4.0, 13.5, 14.6 Hz), 3.50 (dq, 1H, J=7.0, 9.6 Hz), 4.02 (dq, 1H, J=7.1, 9.5 Hz), 4.48 (d, 1H, J=9.2 Hz, H$_{10\beta}$), 5.34 (s, 1H).

EXAMPLE 32

(−)-10a-(3-0-Cholesteroloxycarbonyloxy)dihydroartemisinin (100)

To a solution of dihydroartemisinin (100 mg or 0.352 mmol)in CH$_2$Cl$_2$ (8 mL) under Ar was added DMAP (60 mg or 0.5 mmol) followed by cholesteroylchloroformate (190 mg or 0.42 mmol). After 100 min the bulk of the solvent was evaporated and the residue applied to two 20×20 cm, 1.5 mm SiO$_2$ PTLC plates. The plates were eluted with 10% EtOAc/hexane to give 100 (210 mg or 86% yield) as a glass. Crystallization from hexane afforded a white powder, m.p. 123°-125° C. $[\alpha]_D^{22} = -27.9$ (c=2.85, CDCl$_3$). 1H NMR (400 MHz, CDCl$_3$): δ 0.68 (s, 3H), 0.87 (dd, 6H, J=1.8, 6.6 Hz), 0.91 (d, 3H, J=7.1 Hz), 0.92 (d, 3H, J=6.4 Hz), 0.97 (d, 3H, J=6.0 Hz), 1.01 (s, 3H), 1.43 (s, 3H), 2.39 (m, 2H), 2.59 (ddq, 1H, J=4.5, 7.0, 9.9 Hz), 4.52 (dddd, 1H, J=1.3, 5.5, 10.2, 15.7 Hz), 5.40 (br d, 1H, J=6.3 Hz), 5.44 (s, 1H), 5.59 (d, 1H, J=9.9 Hz). IR (CDCl$_3$): 2950, 2880, 1745, 1450, 1375, 1270, 1260, 1140, 1040, 1000, 900 (br) cm$^{-1}$. DCIMS (NH$_3$): m/e 714 (M+NH$_4$), 386, 369, 284, 267, 249, 239. Anal. Calcd for C$_{43}$H$_{68}$O$_7$: C, 74.10; H, 9.83. Found: C, 74.29; H, 9.96.

EXAMPLE 32

(+)-Octahydro-10b-[2'S,3'-bis(hexadecanoyloxy)prop-1'-yloxy]-3,6,9-trimethyl-3,12-epoxy-12H-pyrano[4.3-j]-1,2-benzodioxep in (101)

To a solution of triphosgene (127 mg or 0.426 mmol) in CH$_2$Cl$_2$ (8 mL) under Ar at 22° C. was added 1,2-dipalmitoyl-sn-glycerol [Sigma Chemical Co., [α]$_D^{22}$=−3.8° (c=1.3, CHCl$_3$); 600 mg or 1.05 mmol] followed by pyridine (85 μL or 83 mg or 1.05 mmol). The mixture was stirred at 22° C. for 60 min whereupon dihydroartemisinin (270 mg or 0.95 mmol) was added at once. Pyridine (95 μL) was added, vigorous gas evolution was noted, and the mixture was stirred 16 h at 22° C., and poured into sat. aq. NaHCO$_3$ (100 mL). The mixture was extracted with EtOAc (1×75 mL). The organic layer was washed with sat. aq. NH$_4$ (3×50 mL), dried over MgSO$_4$, filtered, and the solvent evaporated to give 873 mg of crude product. Flash chromatography on 75 g of silica gel with 10% EtOAc/hexane afforded (at Rf ∼0.3) the product 101 (125 mg, 15%) as an oil. Crystallization from cold hexane gave 101 as a white waxy solid (100 mg), m.p. 49°-50.5° C. [α]$_D^{22}$=64.5 (c=0.44, CHCl$_3$). 1H NMR (400 MHz, CDCl$_3$) shows a 9:1 ratio of isomers at C10b:a, respectively: δ 0.88 (t, 6H, J=7.0 Hz), 0.89 (d, 3H, J=7.0 Hz), 0.96 (d, 3H, J=6.2 Hz), 1.26 (br m, 62H), 1.43 (s, 3H), 1.45-1.68 (m, 10H), 1.74 (br ddd, 2H, J=3.3, 8.2, 12.7 Hz), 1.90 (dddd, 1H, J=1.0, 2.6, 6.0, 13.7 Hz), 2.04 (ddd, 1H, J=2.9, 4.5, 14.5 Hz), 2.32 (m, 6H), 2.64 (ddq, 1H, J=3.3, 4.9, 7.0 Hz), 3.54 (dd, 1H, J=5.8, 10.6 Hz), 3.99 (dd, 1H, J=4.5, 10.6 Hz), 4.13 (dd, 1H, J=6.1, 11.9 Hz), 4.31 (dd, 1H, J=3.8, 11.9 Hz), 4.79 (d, 1H, J=3.3 Hz), 5.25 (dddd, 1H, J=3.8, 4.5, 5.8, 6.1 Hz),5.39 (s, 1H). IR (CHCl$_3$):2930(s), 2860(s), 1735, 1460, 1380, 1220(br), 1165(br), 1115, 1030, 990, 960, 940, 880, 830 cm$^{-1}$. DCIMS (NH$_3$): m/e 852 (M+NH$_4$), 806, 789, 614, 586, 551. Anal. Calcd for C$_{51}$H$_{90}$O$_{11}$: C, 71.90; H, 10.86. Found: C, 71.93; H, 10.72.

EXAMPLE 33

(+)-Octahydro-3,12-epoxy-3,6,9,9-tetramethyl-12H-pyrano [4.3-j]-1,2-benzo dioxepin-10(3H)-one (14)

To a solution of diisopropylamine (60 μL,0.426 mmol) in THF (1 mL) at 0° C. was added n-BuLi (266 μL of 1.60M in hexane). After 10 min at 0° C., the resultant solution was cooled to −78° C. and a solution of (+)-artemisiin (100 mg, 0.355 mmol) in THF (3 mL) was added dropwise over 30 min. After 1 h at −78° C., methyl iodide (55 μL) was added and the resultant mixture was placed in a −40° C. bath. After 90 min between −40° C. and −30° C., saturated aqueous NH$_4$ (15 mL) and 10% HCl (1 mL) was added, and the resultant mixture was extracted with ether (3×15 mL). The combined ethereal layers were washed with saturated aqueous NH$_4$ (15 mL), H$_2$O (3×50 mL), and brine (2×25 mL), dried over Na$_2$SO$_4$ and evaporated to provide 94 mg of yellow semi-crystalline solid, which was purified via flash column chromatography with SiO$_2$. Elution with EtOAc/benzene afforded 39 mg (37%) of which crystals, which recrystallized from hexane to furnish analytically pure white needles, mp 117°-118° C. [α]$_D^{22}$=+73.2 (c=0.645, CHCl$_3$). NMR (400 MHz): δ 0.99 (d, 3H, J=6.0 Hz), 1.06 (dddd, 1H, J=3.6, 11.7, 12.0, 12.0 Hz), 1.19∝1.31 (m, 1H), 1.26 (s, 3H), 1.33-1.53 (m, 3H),1.48 (s, 3H), 1.56 (s, 3H), 1.69 (dd, 1H, J=4.4, 13.7 Hz), 1.76 (ddd, 1H, J=3.3, 6.7, 13.5 Hz), 1.91-2.01 (m, 2H), 2.02-2.09 (m, 1H), 2.37-2.47 (m, 1H), 5.89 (s, 1H). IR (CH$_2$Cl$_2$): 1720, 1095, 1020, 985 cm$^{-1}$. CIMS (NH$_4^+$): m/e (rel int) 314 (M+NH$_4^+$, 90), 297 (M+H$^+$, 40), 279 (92), 251 (50, 233 (45), 233 (100). Anal. Calcd for C$_{16}$H$_{24}$O$_5$: C, 64.84; H, 8.16. Found: C, 64.70; H, 8.03.

EXAMPLE 34

Methylsyn-2[3-(2,2-Dimethoxyethyl)-2E,Z-trimethylsilyl-methy lene]cyclo hexylacetate (50)

As per Schreiber's procedure[11], through a solution of 10-trimethylsilylmethylene bicyclo[4.3.1]-dec-3-ene12 (45, 1.78 g, 7.99 mmol) in dry CH$_2$Cl$_2$ (25 mL) and absolute MeOH (5 mL) at −78° C. was passed a stream of O$_3$/O$_2$. The disappearance of starting material was monitored by periodic TLC (SiO$_2$ in EtOAc/hex) before the mixture was purged with inert gas, treated with pTsOH.H$_2$O (0.13 g, 0.68 mmol), and allowed to warm to ambient temperature over 2 h. The resultant solution was neutralized with NaHCO$_3$ (230 mg), filtered, diluted with dry benzene (10 mL), and concentrated under reduced pressure to 5 mL volume, which was cooled to 0° C. and successively treated with Et$_3$N (1.67 mL) and Ac$_2$O (2.26 mL). After 15 min at 0° C., the mixture was allowed to warm to ambient temperature. After 6 h, the resultant solution was washed with 0.1N HCl (3×35 mL) and 10% aq. NaOH (3×30 mL), dried over Na$_2$SO$_4$, and evaporated to provide 2.77 g of pale yellow oil, which was further purified via flash-column chromatography with silica gel. After elution with EtOAc/hexane, acetal ester 50 was obtained as a colorless oil, 0.99 g (39.2% yield), which consisted of a 1:1 mixture of E:Z isomers by NMR.

NMR (400 MHz): δ 0.079, 0.096 (2s, 9H, —Si(CH$_3$)$_3$), 0.72-1.70 (m, 5.5H), 1.77 (bd, 0.5H, J=11.6 Hz), 1.89 (ddd, 0.5H, J=14.5, 10.9, 6.5 Hz), 2.24 (ddd, 0.5H, J=16.0, 2.8, 0.7 Hz, —CH$_2$ CH (OMe)$_2$), 2.46 (ddd, 1.5H, J=26.4, 14.5, 9.0 Hz, —CH$_2$CO$_2$Me), 2.68 (dd, 1H, J=15.4, 12.3 Hz, —CH$_2$CO$_2$Me), 2.81 (bm, 0.5H), 3.12 (bm, 0.5H), 3.27 (s, 1.5H, —CH(OCH$_3$)$_2$), 3.29 (s, 1.5H, —CH(OCH$_3$)$_2$), 3.32 (s, 1.5H, —CH(OCH$_3$)$_2$), 3.63 (s, 1.5H, —CO$_2$CH$_3$), 3.66 (s, 1.5H, —CO$_2$CH$_3$), 4.29 (t, 0.5H, J=7.3 Hz, —CH(OMe)$_2$), 4.35 (dd, 0.5H, J=7.3, 4.9 Hz, —CH(OMe)$_2$), 5.23 (bs, 1H, =CH(SiMe$_3$)). IR (neat): 2960, 2940, 2870, 2840, 1742, 1608, 1440, 1370, 1293, 1250, 1195, 1175, 1150, 1130, 1083, 1060, 870, 845 cm$^{-1}$. CIMS: (NH$_4^+$) m/e (rel int): 328, (28), 327, (100) for each of two components observed by GC.

EXAMPLE 35 syn-2[3-(2,2-Dimethoxyethyl)-2E,Z, trimethylsilylmethylene] cyclohexylacetic Acid (51)

To a solution of methyl ester 50 (516 mg, 1.63 mmol) in absolute MeOH (15 mL) was added freshly prepared 6N KOH (4 mL). The resultant yellow solution was degassed with argon, refluxed for 90 min, allowed to cool to ambient temperature, stirred with sat. aq. NH$_4$(15 mL), and extracted with Et$_2$O (4×15 mL). The combined ethereal layers were washed with sat. aq. NH$_4$ (2×35 mL), dried over Na$_2$SO$_4$, and evaporated to give a cloudy oil, 378 mg, which was purified via flash-column chromatography with silica gel. After elution with HOAc/EtOAc/hexane and subsequent azeotropic removal of HOAc with CCl$_4$, 338 mg (68.7% yield) of acid 51 was obtained as a colorless oil. NMR (400 MHz) showed a mixture of diastereomers present.

NMR (400 MHz): δ 0.084, 0.099 (2s, 9H, —Si(CH$_3$)$_3$), 0.73–1.82 (m, 5.5H), 1.87 (ddd, 0.5H, J=5.1, 12.4, 14.5 Hz), 2.31 (dd, 0.5H, J=2.2, 16.7 Hz, —CH—CH=), 2.42–2.50 (m, 1H, —CH—CH=), 2.55 (dd, 0.5H, J=8.0, 14.5 Hz, —CH-CH=), 2.72 (dd, 1H, J=11.6, 15.3 Hz, —CH$_2$CO$_2$H), 2.82 (bm, 0.5H, —CH$_2$CO$_2$H), 3.12 (bm, 0.5H, —CH$_2$CO$_2$H), 3.27 (s, 1.5H, —CH(OCH$_3$)$_2$), 3.29 (s, 1.5H, —CH(OCH$_3$)$_2$), 3.30 (s,1.5H —CH(OCH$_3$)$_2$), 3.32 (s,1.5H, —CH(OCH$_3$)$_2$), 4.31 (t, 0.5H, J=6.5 Hz, —CH(OMe)$_2$), 4.37 (dd, 0.5H, J=6.5, 7.3 Hz, —CH(OMe)$_2$), 5.25 (s, 0.5H, =CH(SiMe$_2$)), 5.27 (s, 0.5H, =CH(SiMe$_3$)). IR (neat): 3000, 2950, 2875, 2840, 1710, 1610, 1250, 1130, 1090, 1060, 870, 845 cm$^{-1}$. CIMS: of TMS esters, m/e (rel int) 385 (M+NH$_4$+; 3), 308 (35), 290 (100) for each of two components observed by GC.

EXAMPLE 36

Octahydro-3,11-epoxy-11H-pyrano[4.3-j]-1,2-benzodioxan-9(3H) -one (23)

To a stirring suspension of dimethyl acetal 51 (330 mg, 0.915 mmol) and 230–400 mesh silica gel 60 (0.85 g) in CH$_2$Cl$_2$ (10 mL) was added a freshly prepared solution of 10% aq. oxalic acid (0.20 mL). After 18 h, the silica gel was filtered off and rinsed with CH$_2$Cl$_2$ (35 mL). The filtrate was concentrated in vacuo to 287 mg of yellow oil, which was further purified via flash-column chromatography with silica gel. After elution with HOAc/EtOAc/hexane, 258 mg of aldehyde-acid 52 as a yellow oil was obtained and used immediately. NMR (400 MHz) showed a 1:1 mixture of vinylsilane geometrical isomers was present.

NMR (400 MHz): δ 0.099, 0.096 (2s, 9H, —Si(CH$_3$)$_3$), 0.83–1.81 (m, 6H), 2.29 (dd, 0.5H, J=2.2, 16.7 Hz, —CH—CH=), 2.41–2.62 (m, 2.5H, —CH$_2$CH0, —CH—CH=), 2.69 (dd, 1H, J=11.6, 15.3 Hz, —CH$_2$CO$_2$H), 2.75–2.90 (m, 1H, —CH$_2$CO$_2$H, —CH$_2$CHO), 2.97 (bm, 0.5H, —CH$_2$CHO), 3.12 (bm, 0.5H, —CH$_2$CO$_2$H), 3.25 (bm, 05H, —CH$_2$CHO), 5.31 (s, 0.5H, =CH(SiMe$_3$)), 5.33 (s, 0.5H, =CH(SiMe$_3$)), 9.66 (t, 0.5H, J=2.4 Hz, —CHO), 9.72 (dd, 0.5H, J=2.4, 6.8 Hz, —CHO).

Through a solution of aldehyde-acid 52 in dry CH$_2$Cl$_2$ (30 mL) at −78° C. was passed a stream of O$_3$/O$_2$ from a Welsbach generator (6.0 psi, 70 V, 0.4 L/min) for 2 min. After the resultant solution was purged with argon, Amberlyst™ 15 (200 mg) was added and the mixture was allowed to warm to ambient temperature. After 20 h, the resin was filtered off, and the filtrate was concentrated in vacuo to 128 mg of yellow oil, which was further purified via flash-column chromatography with silica gel and ethyl acetate/hexane. In this fashion 119 mg (58% yield) of lactone 23 as a pale yellow oil was obtained. Crystallization from ethyl acetate/hexane provided analytically pure microprisms, mp 97.5°–98.0° C.

NMR (400 MHz): δ 1.24–1.48 (3H, m), 1.63 (1H, ddd, J=2.1, 5.5, 13.6 Hz, H$_{4\alpha}$), 1.73–1.97 (4H, bm), 2.21 (1H, dd, J=1.0 18.7 Hz, H8a), 2.33 (1H, m, H$_{4\alpha}$), 2.48 (1H, ddd, J=2.6, 10.6, 13.6 Hz, H$_{4\beta}$, 2.94 (1H, dd, J=8.0, 18.7 Hz, H8$\beta$), 5.44 (AB, system, 1H, J=2.1, 2.6 Hz, H$_3$), 6.06 (s, 1H, H11). IR (KBr): 2950, 1740, 1205, 1080, 1038 cm$^{-1}$. CIMS: m/e (rel int) 243 (100)(M+NH$_4$+), 228, (11), 181 (10). Anal. Calcd. for C$_{11}$H$_{14}$O$_5$: C, 58.40; H, 6.24. Found: C, 58.18; H, 6.33.

EXAMPLE 37 t-Butyldimethylsilylcyclohexenylmethyl Acetate (54)

To a solution of the alcohol 53[1] (2.5 g, 11.1 mmol) in dry ether (25 mL) at 22° C. under argon was added pyridine (1.8 mL), followed by acetic anhydride (1.3 mL or 1.2 eq) and DMAP (100 mg). The mixture was stirred overnight and poured into sat. aq. NH$_4$. The resulting mixture was extracted with ether (3×75 mL) and sat. aq. NH$_4$ (2×250 mL). The combined organic layer was dried over MgSO$_4$, filtered, and evaporated to give crude 54. Distillation at 120° C. (0.6 mmHg) gave 2.57 g of 54 (87%) as a colorless oil.

NMR (400 MHz): δ 0.034 (s, 3H), 0.052 (s, 3H), 0.88 (s, 9H), 2.01 (s, 3H), 5.07 (s, 1H), 5.49 (bs, 1H). IR (neat): 1740, 1470, 1370, 1230, 1020, 835, 780 cm$^{-1}$. GC-EIMS: m/e 268 (M+), 225, 211. Anal. Calcd. for C$_{15}$H$_{28}$SiO$_2$ C, 67.11; H, 10.51. Found: C, 67.29; H, 10.71.

EXAMPLE 38

2'Z-t-Butyldimethylsilylmethylidenecyclohexylacetic Acid (55)

To a 0° C. solution of dry diethylamine (1.45 mL, 14 mmol) in THF (30 mL) was added 1.55M n-BuLi (9 mL, 14 mmol). After 15 min, the reaction was cooled to −78° C., and a solution of the ester 54 (2.5 g, 9.33 mmol) in THF (7 mL) was added dropwise (15 min). The reaction mixture was then allowed to warm slowly to 22° C. over 4 h and stirred for 72 h. The mixture was then heated at 50° C. for 4 h, cooled to 22° C., and poured into sat. aq. NH$_4$Cl. The resultant mixture was extracted with CHCl$_3$ (3×50 mL). The organic layers were dried (MgSO$_4$), filtered, and evaporated to give crude 55. Flash chromatography on silica gel (180 g) with 20% EtOAc (1% HOAc)/hexane gave 55 (21.5 g, 86%) as a colorless glass.

NMR (400 MHz): δ 0.035 (s, 3H), 0.042 (s, 3H), 0.85 (s, 9H), 2.05 (m, 1H), 2.31 (m, 1H), 2.40 (m, 1H), 2.58 (m, 2H), 5.04 (s, 1H). IR (neat): 1710, 1615, 1460, 1450, 1410, 1300, 1250, and 840 cm$^{-1}$. EIMS: m/e 253 (M - Me), 211 (M-tertbutyl). CIMS(NH$_3$): m/e 286 (M+NH$_4$), 269 (M+H). Exact mass for C$_{15}$H$_{28}$SiO$_2$-CH$_3$: Calcd., 253.162. Found, 253.162. For C$_{15}$H$_{28}$SiO$_2$-tertbutyl: Calcd., 211.115. Found, 211.117.

EXAMPLE 39

1'R-Butyl-2Z-tertbutyldimethylsilylmethylenecyclohexylacetic Acid (28)

To a solution of dry diisopropylamine (0.59 mL, 4.21 mmol) in THF (15 mL) at 0° C. under argon was added 2.8M n-BuLi (1.55 mL, 4.21 mmol). After 15 min, the reaction mixture was cooled to −78° C., and the acid 55 (500 mg, 1.87 mmol) in THF (5 mL) was added dropwise. The reaction mixture was warmed to 22° C., then heated at 50° C. for 2 h and cooled to −78° C., at which point purified n-butyl iodide (0.5 mL) was added. After 2 h at 22° C., the reaction mixture was poured into sat. aq. NH$_4$Cl and extracted with EtOAc. The organic layers were dried over MgSO$_4$, filtered, and the solvent removed to afford crude 57 (650 mg). Flash chromatography on silica gel (75 g) with 20% EtOAc (1% HOAc)/hexane gave pure 57 as a waxy solid (563 mg, 93%).

NMR (400 MHz): δ 0.042 (s, 3H), 0.054 (s, 3H), 0.86 (s, 9H), 1.74 (m, 1H), 1.94 (ddd, J=4, 4, 13 Hz, 1H), 2.27 (dt, J=3, 13 Hz, 1H), 2.37 (broad dt, J=3, 11 Hz, 1H), 2.67 (ddd, J=4, 4, 11 Hz, 1H), 5.18 (s, 1H). EIMS: m/e 309 (M-Me), 267 (M-tertbutyl). CIMS (NH$_3$): m/e 342 (M+NH$_4$), 325 (M+H), 211. Exact mass for C$_{18}$H$_{30}$O$_2$-Si-Me: Calcd., 309.225. Found, 309.226. For C$_{18}$H$_{30}$O$_2$ Si-tertbutyl: Calcd., 267.178. Found, 267.179.

EXAMPLE 40

1β-tert-Butyldimethylsilyloxy-4β-butyl-8aα-hydroperoxy-4aα-hexahydroiso chroman-3-one (58)

A solution of the acid 57 (560 mg, 1.73 mmol) in MeOH (20 mL) at −78° C. was treated with a stream of O$_3$/O$_2$ (7 psi, 0.5 L/min, 70 V) for 8 min. The TLC was examined (20% EtOAc/hexane-SiO$_2$) for 57 (absent), then argon was passed through the solution. The solvent was evaporated (bath temp. below 10° C.), and the residue was placed under high vacuum for 24 h. After another 48 h at 5° C., the residue was flash-chromatographed on silica gel (50 g) with 10% EtOAc/hexane to give pure 58 (355 mg, 55%) as an oil.

NMR (90 MHz): δ 0.16 (s, 3H), 0.20 (s, 3H), 0.93 (s, 9H), 2.70 (m, 1H), 5.70 (s, 1H). IR (neat): 1750 cm$^{-1}$. CIMS(NH$_3$): m/e 390 (M+NH$_4$), 373 (M+H), 357, 346, 339, 327, 313, 242, 226. Exact mass for C$_{19}$H$_{35}$O$_3$Si-OOH: Calcd., 339.235. Found, 339.237. For C$_{19}$H$_{35}$O$_3$-Si-tertbutyl: Calcd., 315.163. Found, 315.164.

EXAMPLE 41

7-Butyl-3,3-dimethyl-4aH,6H-hexahydro-1,2,4-trioxino[6.5-j] benzopyran-6-one (26)

To a solution of the hydroperoxide 58 (330 mg) in acetone (20 mL) under argon at 22° C. was added TFA (2.5 mL). After 24 h the mixture was poured into water (100 mL) and extracted with hexane (100 mL). The hexane layer was washed with sat. aq. NaHCO$_3$ (3×75 mL), dried over MgSO$_4$, filtered, and evaporated to give crude 26 (250 mg). PTLC on silica gel (3×1.5-mm plates) with 10% EtOAc/hexane gave pure 26 (141 mg, 52%). Crystallization from cold pentane gave crystals, mp 60°-62° C.

$^1$H NMR (400 MHz, DMSO-d$_6$, 100° C.): δ 0.89 (t, J=6.8 Hz, 3H), 1.40 (bs, 3H), 1.48 (bs, 3H), 1.93 (dt, J=4.5, 13 Hz, 1H), 2.32 (bs, 1H), 2.92 (m, 1H), 3.00 (m, 0.5 H), 5.74 (s, 1H). 13C NMR (DMSO-$_6$, at 100° C.); d 12.9, 21.2, 21.3, 22.5, 23.3, 24.1, 25.4, 28.2, 30.4, 37.9, 40.6, 77.5, 93.3, 102.1, 170.4. IR (CHCl$_3$): 1740, 1390, 1180, 1110, 1090, 1000 cm$^{-1}$. CIMS(NH$_3$) m/e: 316 (M+NH$_4$+), 300, 299, (M+H+), 257, 240, 223, 212. Anal. Calcd. for C$_{16}$H$_{26}$O$_5$: C, 64.41; H, 8.78. Found: C, 64.67; H, 9.06.

EXAMPLE 41

(±)-Hexahydro-3,3-dimethyl-4aH,6H-1,2,4-trioxino-[6.5-j][2] benzopyran-6-one (25)

Through a solution of 2'Z-t-butyldimethylsilylmethylenecyclohexylacetic acid (55, 1.00 g, 3.73 mmol) in absolute MeOH (100 mL) at −78° C. was passed O$_3$/O$_2$ for 10 min, whereupon starting material was absent by TLC (SiO$_2$ in HOAc/EtOAc/hex). The reaction mix was purged with argon, allowed to warm to 10° C., and concentrated in vacuo to a yellow oil, which was allowed to sit at 1 mm Hg for 15 h at ambient temperature prior to purification via flash-column chromatography with SiO$_2$. Elution with HOAc/EtOAc/hex allowed isolation of 1β-t-butyldimethylsiloxy-8aα-hydroperoxy-5aα,7,8aα-hexahydroisochroman-3-one (60) as a yellow, semicrystalline oil, 186 mg (17%), which was routinely used without further purification.

The hydroperoxide 60 (140 mg, 0.486 mmol) was placed in acetone (5 mL) and treated with TFA (1.0 mL). More TFA (0.25 mL) was added after 6 h. After 30 h, the reaction was quenched with sat. aq. NaHCO$_3$ (30 mL) and extracted into EtOAc (4×15 mL). The combined EtOAc layers were washed with sat. aq. NaHCO$_3$ (25 mL) and brine (50 mL), dried over Na$_2$SO$_4$, and evaporated to yellow oil, which was purified via successive flash-column and thin-layer chromatography with SiO$_2$. Elution with EtOAc/hexane afforded 30 mg of 25 as colorless oil, which crystallized from hex, mp 106°-107° C.

$^1$H NMR (400 MHz, DMSO-d$_6$, 90° C.): δ 1.17-1.42 (m, 2H), 1.42-1.57 (m, 7H), 1.57-1.73 (m, 3H), 2.00-2.47 (bm, 2H), 2.75 (dd, 1H, J=5.8, 17 Hz), 5.65 (s, 1H). IR (CH$_2$Cl$_2$): 2945, 1748, 1380, 1210, 1120, 1050, 1000 cm$^{-1}$. CIMS (NH$_4$+): m/e (rel int) 260 (M+NH$_4$+, 28), 243 (M+H+, 7), 186 (22), 174 (19), 157 (20), 156 (100), 139 (93). Anal. Calcd. for C$_{12}$H$_{12}$O$_5$: C, 59.49; H, 7.49. Found: C, 59.64; H, 7.64.

EXAMPLE 42

2-(2'E-t-Butyldimethylsilylmethylidenecyclohexyl)-2-methylpropionic Acid (63)

To a solution of diisopropylamine (1.24 mL, 8.89 mmol) in dry THF (25 mL) at 0° C. was added dropwise n-BuLi (5.56 mL of 1.60M in hexane). After 10 min at 0° C., a solution of monomethyl acid 62 (1.14 g, 4.04 mmol) in THF (5 mL) was added via cannula. The resultant orange solution was allowed to warm to ambient temperature, then heated in an oil bath to 60° C. After 20 h, the resultant red solution was treated with MeI (0.90 mL), whereupon a yellow solution was obtained. A yellow suspension formed after cooling to ambient temperature over 30 min. The suspension was stirred with 10% aq. HCl (15 mL). The organic layer was reserved, and the aqueous layer further extracted with CHCl$_3$ (4×15 mL). The combined organic layers were washed with 10% aq. HCl (15 mL) and freshly prepared 20% aq. NaHS$_2$O$_3$ (2×25 mL), dried over Na$_2$SO$_4$, and evaporated to provide 1.35 g of a yellow semi-crystalline solid, which was further purified upon flash chromatography with silica gel. After elution with HOAc/EtOAc/hex, 905 mg (76%) of desired gem-dimethyl acid 63 as pale yellow crystals, mp 113°-114° C., was obtained along with 121 mg (10% recovery) of starting material.

NMR (400 MHz): δ 0.02 (s, 3H, Si(CH$_3$)), 0.03 (s, 3H, Si(CH$_3$)), 0.83 (s, 9H, (H$_3$C)$_3$CSi), 1.21 (s, 6H, CH$_3$), 1.32-1.83 (m, 6H, CH$_2$), 2.04 (ddd, 1H, J=5.0, 9.8, 12.8 Hz, =C—CH$_2$—), 2.36 (dt, 1H, J=5.0, 12.8 Hz) =C—CH$_2$—), 2.42 (dd, 1, J=4.4, 8.8 Hz, =C—CH), 5.10 (s, 1H, =CH). IR (CH$_2$Cl$_2$): 3300-2100, 1700 cm$^{-1}$. EIMS: m/e (rel int): 281 (2, M-CH$_3$), 239 (78), 147 (23), 75 (100), 73 (25). Anal. Calcd. for C$_{17}$H$_{32}$O$_2$Si: C, 68.86; H, 10.88. Found: C, 69.14; H, 11.06.

EXAMPLE 43

(±)-1β-t-Butyldimethylsilyloxy-4,4-dimethyl-8aα-hydroperoxy-5aα,7,8aα-hexahydro-isochroman-3-one (64)

Through a solution of 2-(2'E-t-butyldimethylsilylmethylidenecyclohexyl)-2-methylpropionic acid (63, 900 mg, 3.00 mmol) in absolute MeOH (100 mL) at −78° C. was passed O$_3$/O$_2$ until a blue color persisted. The resultant solution was carefully concentrated in vacuo to a yellow oil, which was stored under argon at −15° C. for two days before purification via flash-column chromatography with silica gel. Elution with HOAc/EtOAc/hex provided isochroman-3-one 64 as white crystals, 0.19 g (50%), mp 116°–116.5° C.

$^1$H NMR (400 MHz): δ 0.15 (s, 3H, SiCH$_3$), 0.16 (s, 3H, SiCH$_3$), 0.89 (s, 9H, (CH$_3$)$_3$C), 1.21 (s, 3H, CH$_3$), 1.22 (s, 3H, CH$_3$), 1.33 (dddd, 1H, J=6.1, 8.0, 8.2, 13.9 Hz), 1.42–1.49 (m, 1H), 1.50–1.64 (bm, 4H), 1.82 (bd, 1H, J=12.9 Hz), 2.05–2.17 (m, 2H), 5.53 (s, 1H, OCHO), 7.89 (bs, 1H, OOH). IR (CH$_2$Cl$_2$): 3520, 3300 (broad), 2950, 2870, 1725, 1393, 1185, 1103, 1030, 1008, 850 cm$^{-1}$. CIMS: (NH$_4^+$): m/e (rel int) 357 (M+NH$_4^+$, 2), 345 (M+H$^+$, 5) 214 (100). Anal. Calcd. for C$_{17}$H$_{32}$O$_5$Si: C, 59.27; H, 9.36. Found C, 59.68; H, 9.38.

EXAMPLE 44

(±)Hexahydro-3,3,7,7-tetramethyl-4aH,6H-1,2,4-trioxino [6.5-j][2]benzopyran-6-one (27)

To a solution of hydroperoxide 64 (74 mg, 0.22 mmol) in acetone (10 mL) was added TFA (0.50 mL). Additional TFA aliquots (0.25 mL) were added at 24 and 30 h. After 48 h, sat. aq. NaHCO$_3$ (35 mL) was carefully added and the resultant mix extracted with EtOAc (4×15 mL). The organic layers were combined, washed with sat. aq. NaHCO$_3$ (35 mL) and brine (2×50 mL), dried over Na$_2$SO$_4$, and evaporated to provide 54 mg of yellow oil, which was purified via flash-column chromatography with silica gel. Elution with EtOAc/hexane afforded 23 mg (39%) of 27 as white platelets, which were recrystallized from hexane to give white prisms, mp 116°–117° C.

$^1$H NMR (400 MHz): δ 1.06–1.93 (bm, 1H), 1.26 (s, 3H), 1.28 (s, 3H), 1.38 (bs, 3H), 1.49–1.73 (m, 9H), 1.90 (bd, 1H, J=12.8 Hz), 2.78 (bd, J=12.5 Hz), 5.22 (s, 1H). IR (CH$_2$Cl$_2$): 2955, 1733, 1388, 1215, 1170, 1135, 1100, 1055, 1013, 995 cm$^{-1}$. CIMS (NH$_4^+$): m/e (rel int) 288 (M+NH$_4^+$, 6), 271 (M+H$^+$, 2), 189 (100), 167 (65). Anal. Calcd. for C$_{14}$H$_{22}$O$_5$: C, 62.20; H, 8.20. Found: C, 62.52; H, 8.31.

EXAMPLE 45 t-Butyldimethylsilylcyclohexenylmethyl Hemisuccinate (65)

To a solution of alcohol 53 (2.57 g, 11.4 mmol) in Et$_2$O (25 mL) was added in succession DMAP (100 mg), pyridine (1.8 mL), and succinic anhydride (1.37 g). The resultant suspension was diluted with CH$_2$Cl$_2$ (100 mL). After 12 h, more pyridine (1.8 mL) and succinic anhydride (1.37 g) were added. After 3 days, the mix was stirred with 5% HCl (75 mL) and extracted with CHCl$_3$ (3×100 mL). The combined organic layers were washed with 5% aq. HCl (50 mL) and brine (100 mL), dried over Na$_2$SO$_4$, and evaporated to give a pale brown oil, which was purified via flash-column chromatography with SiO$_2$. Elution with HOAc/EtOAc/hex provided 1.05 g (28%, 64% based on recovery of 53) of hemisuccinate 65 as a colorless oil.

NMR (400 MHz): δ-0.05 (s, 3H, SiCH$_3$), 0.04 (s, 3H, SiCH$_3$), 0.87 (s, 9H, C(CH$_3$)$_3$), 1.42–1.67 (m, 4H, —CH$_2$CH$_2$) 1.80–2.09 (m, 4H, —CH$_2$CO$_2$), 2.58–2.73 (m, 4H, =CH—CH$_2$), 5.10 (s, 1H, CO$_2$CHSi), 5.48 (s, 1H, =CH). IR (neat): 3500–2200, 2940, 2870, 1740, 1720, 1250, 1160 cm$^{-1}$. EIMS: m/e (rel int) 326 (3), 225 (23), 131 (25), 75 (37), 73 (100).

EXAMPLE 46

(±)Erythro-3-carboxy-2(2'E-t-butyldimethylsilylmethylenecyclohexyl) propionic Acid (66)

To a solution of diethylamine (0.33 mL) in THF (5 mL) at 0° C. was added dropwise n-BuLi (2.0 mL) of 1.60M in hexane). After 15 min at 0° C., the solution was cooled to −78° C., and a solution of hemisuccinate 65 (417 mg, 1.28 mmol) in THF (2 mL) was added dropwise via cannula and allowed to slowly warm to ambient temperature overnight. After 15 h, the resultant yellow solution was stirred with sat. aq. NH$_4$Cl (35 mL) and 10% aq. HCl (10 mL) and extracted with CHCl$_3$ (3×25 mL). The combined layers were washed with brine (35 mL), dried over Na$_2$SO$_4$, and evaporated to afford a yellow crystalline solid, which was recrystallized from EtOAc to provide 66 as colorless crystals, mp 179°–180° C.

NMR (400 MHz, DMSO-d$_6$): δ 0.02 (s, 3H, SiCH$_3$), 0.03 (s, 3H, SiCH$_3$), 0.84 (s, 9H, C(CH$_3$)$_3$), 1.36–1.65 (m, 6H, CH$_2$CH$_2$), 2.07–2.15 (m, 1H, HO$_2$CCH)2.33–2.52 (m, 4H, HO$_2$CCH$_2$, =CH—CH$_2$), 3.01 (ddd, 1H, J=10.9, 7.6, 3.7 Hz, =CH—CH), 5.03 (s, 1H, =CH). IR (nujol): 3480–2110, 1710 cm$^{-1}$. CIMS: m/e (rel int) 344 (M+NH$_4^+$; 10), 327 (M+H$^+$, 45), 211 (100). Anal. Calcd. for C$_{17}$H$_{30}$O$_4$Si: C, 62.54; H, 9.26. Found: C, 62.66; H, 9.41.

EXAMPLE 47

(+)Hexahydro-7(2'-acetic acid)-3,3-dimethyl-4aH,6H-1,2,4-trioxino[6.5-j][2]benzopyran-6-one (28)

Through a solution of diacid 66 (595 mg, 1.83 mmol) in absolute MeOH (75 mL) at −78° C. was passed O$_3$/O$_2$ for 6 min, whereupon starting material was absent by TLC (SiO$_2$ in HOAc/EtOAc/hex). The resultant solution was purged with argon, allowed to warm to 0° C., and concentrated under reduced pressure to a colorless foam, which was allowed to set for 24 h prior to purification via flash-column chromatography. Elution with HOAc/EtOAc/hex led to the isolation of 185 mg (27%) of hydroperoxyisochromanone 67 as an unstable white foam, which was used immediately without further purification.

NMR (90 MHz): δ 0.19 (s, 6H, SiCH$_3$), 0.093 (s, 9H, SiC(CH$_3$)$_3$), 1.10–2.09 (m, 9H), 2.30–3.05 (m, 3H), 5.66 (s, 1H). IR (CH$_2$Cl$_2$): 3500, 3550–2000 (broad), 2937, 1745, 1721, 848 cm$^{-1}$.

To a solution of the hydroperoxide 67 (160 mg, 0.428 mmol) in acetone (10 mL) was added TFA (0.75 mL). More TFA aliquots (0.25 mL) were added at 1, 19, 23, 27, 30, and 33 h. After 6 days, the resultant brown solution was diluted with brine (30 mL) and H$_2$O (enough to dissolve solids) and extracted with CHCl$_3$. The combined organic layers were washed with brine (4×35 mL), dried over Na$_2$SO$_4$, and evaporated to give a brown oil, which was purified via flash-column chromatography with SiO$_2$. Elution with HOAc/EtOAc/hex led to isolation of desired acetonide 28 as a white foam, 29 mg (23%), which crystallized from EtOAc/hex, mp 159°–160° C.

NMR (400 MHz, DMSO-d$_6$, 95° C.): δ 1.32–1.59 (m, 10H), 1.60–1.76 (bm, 2H), 1.98 (quintet, 1H, J=7.2 Hz), 2.59 (dd, J=4.8, 14.4 Hz), 2.62 (dd, 1H, J=4.8, 14.4 Hz), 2.90–3.15 (bm, 4H), 5.51 (s, 1H). IR CH$_2$Cl$_2$): 3260–2280 (broad), 1757, 1722, 1052 cm$^{-1}$. CIMS (NH$_4^+$): m/e (rel int) 318 (M+NH$_4$+, 3), 301 (M+H+, 7), 283 (5), 244 (30), 214 (100).

EXAMPLE 48

(4aS,7R,7aS,10R,11aR) Hexahydro-3,3,7,10-tetramethyl-4aH,6H-1,2,4-trioxino[6.5-j][2]benzopyran-6-one (29i)

To a solution of N'-3'R-methylcyclohexylimine p-toluenesulfonyl hydrazide (73) (from R-pulegone, 19.0 g, 67.8 mmol) in dry TMEDA (100 mL) at −78° C. was added n-BuLi (100 mL of 2.7M in hexane). The resultant mix was allowed to warm to ambient temperature. After 90 min, the mix was cooled to 0° C. and dry DMF (50 mL) was added. After 30 min, the mixture was poured into sat. aq. NH$_4$Cl and extracted with Et$_2$O (3×). The combined ethereal layers were washed with sat. aq. NH$_4$Cl, sat. aq. NaHCO$_3$ (2×), H$_2$O (2×), and brine, dried over MgSO$_4$, filtered through SiO$_2$, and evaporated at below ambient temperature to provide an oil, which was purified after flash-column chromatography with SiO$_2$ (Et$_2$O/hexane) and subsequent distillation at aspirator pressure (~50 mm Hg), bp 120° C., to afford 2.9 g (34%) of oil. The TLC and 1H NMR (400 MHz) spectrum indicated that a 1:1 mix of double-bond isomeric aldehydes, 5R-methyl-cyclohexenecarboxaldehyde (74) and 3R-methylcyclohexenecarboxaldehyde (75), had been obtained. This mixture was typically used without further purification, but in some experiments, each isomer was enriched via rigorous flash-column chromatography with SiO$_2$ (Et$_2$O/hex) and partially characterized.

3R-Methylcyclohexenecarboxaldehyde (74)

NMR (90 MHz): d 0.93-2.64 (m, 10H), 6.61 (m, 1H, =CH), 9.30 (s, 1H CHO).

5R-Methylcyclohexenecarboxaldehyde (75)

NMR (90 MHz): d 0.93-1.95 (m, 8H), 2.00-2.69 (bm, 2H), 6.75 (m, 1H, =CH), 9.40 (s, 1H, CHO).

To a solution of 5R-methylcyclohexenecarboxaldehyde (74) (380 mg, 3.06 mmol) in Et$_2$O (10 mL) at −78° C. was added a solution of tris(trimethylsilyl)aluminum-(III) etherate[1] (3 mL of 1.4M in pentane). After a few minutes, the mixture was treated in succession with DMAP (10 mg) and proprionic anhydride (1 mL) and allowed to warm to ambient temperature. After 3 days, the reaction was stirred with aq. sodium potassium tartrate. The separated organic layer was washed with sat. aq. NH$_4$C$_{14}$ and sat. aq. NaHCO$_3$, dried over Na$_2$SO$_4$, and evaporated to provide 650 mg of oil, which was purified via flash-column chromatography. Elution with EtOAc/hex led to the isolation of 450 mg (58%) of diasteromeric 5'R-methylcyclohexenyltrimethylsilylmethyl proprionate (76) as an oil.

NMR (400 MHz): 0.02 (s, 9H, SiCH$_3$), 0.92, 0.93 (2d, 3H, J=6.4 Hz, 3'-CH$_3$), 1.12, 1.13 (2t, 3H, J=7.6 Hz, CH$_2$CH$_3$), 1.44-1.78 (m, 4H), 1.80-2.23 (m, 3H), 2.32, 2.33 (2q, 2H, J=3.4 Hz), 4.93, 4.96 (2s, 1H, SiCHO$_2$C), 5.38, 5.43 (2bs, 1H, =CH). IR (neat): 2860, 2820, 1743, 1255, 1190, 848 cm$^{-1}$. EIMS: m/e (rel int) 254 (10), 225 (10), 197 (33), 131 (20), 73 (100). Exact Mass Calcd. for C$_{14}$H$_{26}$O$_2$Si: 254.170. Found: 254.170.

To a solution of diethylamine (385 mL, 3.7 mmol) in THF (5 mL) at −78° C. was added n-BuLi (1.38 mL of 2.7M in hexane). The solution was allowed to warm to 0° C. over 15 min, then recooled to −78° C., and a solution of proprionate 76 (430 mg, 1.69 mmol) in THF (5 mL) was added. The resultant solution was allowed to warm to ambient temperature overnight. The reaction was stirred with sat. aq. NH$_4$Cl (150 mL) and 5N HCl (1 mL) and extracted with CHCl$_3$ (3×). The combined organic layers were washed with brine, dried over Na$_2$SO$_4$, and evaporated to obtain 510 mg of crude product, which was purified after flash-column chromatography with SiO$_2$. Elution with HOAc/EtOAc/hex provided 288 mg (67%) of oil, which was primarily erythro-2(2'E,Z-t-butyldimethylsilylmethylene-3'R-methylcycl ohexyl) propionic acid (77) as determined by 400 MHz 1H NMR (approximately 50% desired isomer) and used without further purification.

Through a solution of vinylsilane acid 77 (275 mg, 0.92 mmol) in absolute MeOH (40 mL) at −78° C. was passed O$_3$/O$_2$ for 5 min, whereupon a blue color persisted. The mixture was purged with argon, concentrated in vacuo at 17° C., and stored under high vacuum at ambient temperature overnight. The resultant residue was placed in acetone (10 mL) and treated with TFA (1.9 mL). After 7 h, the mixture was stirred with H$_2$O and extracted with EtOAc (2×). The combined organic layers were washed with sat. aq. NaHCO$_3$, dried over Na$_2$SO$_4$, and evaporated to give 139 mg of crude material, which was purified via thin-layer chromatography with SiO$_2$. Development with EtOAc/hex provided 23 mg (11%) of trioxane 29i as white crystals from cold pentane, mp 106°-108° C. [α]$_D^≅$ = −112.7 (c=0.14, CHCl$_3$).

1H NMR (DMSO-d$_6$, 120° C.): δ 0.80 (d, 3H, J=7.5 Hz, 10-CH$_3$), 1.16 (d, 3H, J=7.1 Hz, 7-CH$_3$), 1.41 (bs, 3H, 3-CH$_3$), 1.48 (bs, 3H, 3-CH$_3$), 1.50-1.65 (m, 5H 5H), 237 (bt, 1H, J=5.8 Hz), 2.21 (bm, 1H), 2.33 (bm, 1H), 3.08 (bm, 1H), 5.67 (s, 1H, H$_{4α}$). IR (nujol): 1753 cm$^{-1}$. Anal. Calcd. for C$_{14}$H$_{22}$O$_5$: C, 62.20; H, 8.20. Found: C, 62.34; H, 8.12.

EXAMPLE 49

2S-(1'-t-Butyldimethylsilyloxy-2'R-propyl)-5R-methyl-1-E/Z-trimethylsilyl methylenecyclohexane (114)

To solution of dry pentane (200 mL) and methoxydimethylsilyltrimethylsilylmethane (4.5 mL or 20 mmol) under argon at −78° C. was added 1.7M t-BuLi (11.8 mL or 20 mmol). The mixture was warmed to 23° C. and stirred 120 min, recooled to −78° C., and treated with the ketone 113 (5.6 g or 18 mmol) dissolved in pentane (50 mL). The mixture was allowed to warm slowly to 23° C. while stirring overnight. The reaction mixture was poured into sat. aq. NH$_4$Cl (500 mL), washed with additional portions of NH$_4$Cl (2×500 mL), dried over MgSO$_4$, filtered, and the solvent evaporated to give a light yellow oil. Flash chromatography on silica gel (150 g) with 5-20% EtOAc/hexane gave the desired product 114 (1.21 g or 19% yield) as a colorless oil. While the product 114 was most conveniently used as a 60:40 E/Z mixture, the isomers could be separated by SiO$_2$, PTLC eluting with hexane. In this manner, 380 mg of 114 gave 203 mg of isomer 114a and 127 mg of 114b. For 114a, 1H NMR (400 MHz, CDCl$_3$): δ 0.06 (s, 6H), 0.10 (s, 9H), 0.84 (d, 3H, J=6.8 Hz), 0.91 (s, 9H), 1.22 (br dddd, 1H, J=2.4, 4.1, 4.5, 13.3 Hz), 1.61 (ddd, 1H, J=4.1, 4.1, 13.8 Hz), 1.67 (m, 1H), 1.74 (br d, 1H, J=13.0 Hz), 1.82 (dddd, 1H, J=4.7, 4.7, 13.7, 13.7 Hz), 1.97 (m, 1H), 2.07 (m, 1H), 2.34 (br d, 1H, J=10.6 Hz), 2.52 (ddd, 1H, J=1.3, 5.3, 12.5 Hz), 3.54 (dd, 1H, J=5.7, 9.9 Hz), 3.65 (dd, 1H, J=3.2, 9.9 Hz), 5.15 (d, 1H, J=1.1 Hz). IR: 1615, 1260, 1120, 1100, 875, 850, 780 cm$^{-1}$. EIMS: (m/e) 354 (M+), 339 (M-CH$_3$), 297 (M- tBu), 222, 211, 209, 182. Anal. Calcd for $C_{20}H_{42}Si_{2O}$: C, 67.72; H, 11.93. Found: C, 68.01; H, 12.17. For Isomer 114b, 1H NMR (400 MHz, CDCl$_3$): δ 0.047 (s, 6H), 0.10 (s, 9H), 0.9 (s, 9H), 0.91 (d, 3H, J=6.6 Hz), 0.93 (d, 3H, J=6.6 Hz), 1.05-1.25 (m, 2H), 1.66 (m, 1H), 1.76 (dd, 1H, J=8.8, 12.6 Hz), 1.83 (m, 2H), 1.90 (dq, 1H, J=3.5, 6.6 Hz), 2.41 (ddd, 1H, J=1.1, 4.2, 12.5 Hz), 3.42 (dd, 1H, J=6.8, 9.7 Hz), 3.68 (dd, 1H, J=3.5, 9.7 Hz),5.14 (s, 1H). IR: 1615, 1250, 1100, 840, 780 cm$^{-1}$. EIMS: (m/e) 354 (M+), 339 (M-CH$_3$), 297 (M-tBu), 251, 222, 211, 209, 182. Anal. Calcd for $C_{20}H_{42}Si_{2O}$: C, 67.72; H, 11.93. Found: C, 67.19; H, 12.07.

EXAMPLE 50

2S-(2'R-Propionyl)-5R-methyl-1E/Z-trimethylsilylmethylenecyclohexane (115)

Isomer 114a (190 mg or 0.54 mmol) and 114b (110 mg or 0.31 mmol) were each separately dissolved in THF (5 mL) and treated, at 22° C. under Ar, with 1.1 mL and 0.7 mL, respectively, of 1.0M Bu$_4$NF in THF (Aldrich Chemical Co.). After 2.5 h at 22° C., the separate reactions were each poured into water and extracted with Et$_2$O (3×25 mL). The combined organic layers were washed with sat. aq. NaHCO$_3$ (3× 50 mL), dried over MgSO$_4$, filtered, and evaporated to give the crude alcohols, 130 and 75 mg respectively, which were used without further purification as follows. The alcohols a and b (130 mg and 75 mg) were each dissolved in dry DMF (6 and 4 mL) and treated separately, at 22° C. under Ar, with pyridinium dichromate (700 mg and 400 mg). The mixtures were stirred 18 h at 22° C. and then poured into water (100 mL) and extracted with ether (3×25 mL). The combined organic phases were washed with sat. aq. NH$_4$Cl:5N HCl (9:1, 2×50 mL), and sat. aq. NaCl (2×50 mL), dried over MgSO$_4$, filtered, and the solvent evaporated to give the crude acids 115a (125 mg) and 115b (71 mg). PTLC of both acids on 1.5 mm SiO$_2$ plates with 10% EtOAc/hexane produced each of the pure acids: 115a (114 mg or 84%) as a white crystalline solid, m.p. 75°-77° C.. 1H NMR (400 MHz, CDCl$_3$): δ 0.14 (s, 9H), 0.91 (d, 3H, J=7.0 Hz), 1.09 (d, 3H, J=6.9 Hz), 1.29 (br d, 1H, J=15.3 Hz) 1.52 (br d, 1H, J=12.5 Hz), 1.73 (ddd, 1H, J=4.5, 4.5, 10 Hz), 1.77 (br d, 1H, J=12.8 Hz), 1.90 (dddd, 1H, J=4.2, 4.2, 13.7, 13.7 Hz), 2.10 (br m, 1H), 2.43 (ddd, J=1.5, 5.3, 12.9 Hz, 1H) 2.73 (br dd, 1H, J=3.0, 10.0 Hz), 2.91 (br dq, 1H, J=7.0, 12.0 Hz), 5.25 (s, 1H). Anal. Calcd for C$_{14}$H$_{26}$SiO$_2$: C, 66.09; H, 10.30. Found: C, 65.80; H, 10.41. PTLC also gave acid 115b (62 mg or 78%) as a colorless oil. 1H NMR (400 MHz, CDCl$_3$): 0.11 (s, 9H), 0.93 (d, 3H, J=6.6 Hz), 1.16 (d, 3H, J=6.5 Hz), 5.15 (s, 1H). Anal. Calcd for C$_{14}$H$_{26}$SiO$_2$: C, 66.09; H, 10.30. Found: C, 65.85; H, 10.32.

EXAMPLE 51

(−)-4ab,7a,7aa,10β-Hexahydro-3,3,7β,10a-tetramethyl-4aH,6H-trioxino[6.5-j][2]-benzopyran-6-one (29)

The acids 115 were ozonized, either as mixtures or as the separate isomers with identical results, as follows. To a −78° C. solution of acid 115 (260 mg, 1.02 mmol) in methanol (8 mL) was bubbled ozonized oxygen from an OREC ozone generator (0.6 L/min, 7 p.s.i., 65 V, 0.7 amps) until a faint blue-grey color was observed (about 4 min). The −78° C. solution was purged with argon until the color was gone, the stir bar was removed and the mixture evaporated to dryness by rotary evaporation (bath temperature <20° C.). The mixture was evaporated to dryness from hexane (10 mL) twice, and placed under vacuum (0.2 mm Hg) for 30 min. The residual glass was dissolved in CH$_2$Cl$_2$ (3 mL), to which was sequentially added acetone (3 mL) and Amberlyst TM 15 (275 mg). The mixture was stirred at 22° C. under Ar for 18 h and then filtered. The filtrate was evaporated to give crude 29 (233 mg). Purification on one SiO$_2$ PTLC plate, eluting with 10% EtOAc/hexane, gave pure 29 (68 mg or 25% yield) as a white solid which was recrystallized from cold hexane, m.p. 109°-110° C. [α]$_D^{22}$=−94.5° (c=0.145, CHCl$_3$). 1H NMR (400 MHz, CDCl$_3$) was temperature dependent. At 23° C., the spectra was broad, while at −10° C., a clean 2:1 mixture was observed: δ 0.98 and 1.00 (2d, 3H, J=6.4 Hz), 1.19 and 1.23 (2d, 3H, J=7.2 Hz), 1.41 and 1.57 (2s, 3H), 1.64 and 1.65 (s, 3H), 2.02 and 2.68 (ddd, 1H, J=2.0, 4.0, 13.5 Hz), 3.10 and 3.55 (2dq, 1H, J=5.0, 7.2 Hz), 5.61 and 5.70 (2s, 1H). IR (Nujol): 1755, 1215, 1180, 1100, 1030, 1010, 880, 840 cm$^{-1}$. DCIMS-NH$_3$: (m/e) 288 (M+NH$_4$), 271 (M+H), 255, 230, 212, 195, 184, 167. Anal. Calcd for C$_{14}$H$_{22}$O$_5$: C, 62.20; H, 8.20. Found: C, 61.90; H, 8.02.

EXAMPLE 52

(−)-4aβ,7a,7aa,10β-Hexahydro-3β7,β,10a-trimethyl-4aH,6H-trioxino[6.5-j][2]- benzopyran-6-one (116)

The acid 115 was ozonized as described above for 29, and treated identically except that acetaldehyde was substituted for acetone and the ensuing cyclization was complete in a few hours. The purification product 116 was crystallized from hexane, m.p. 102°-103° C. (lit.13 m.p. 95°-96° C.). No rotation was given, we found [α]$_D^{22}$=−19.3° (c= 0.28, CHCl$_3$). The NMR was in accord with the reported spectra 13.

EXAMPLE 53

(−)-Hexahydro-3,3,10a,11β-tetramethyl-4aH,6H-1,2,4-trioxino-[6.5-j]benzopyran-6-one (30)

To a solution of cyclohexylisopropylamine (15.5 g, 18 mL, 0.11 mol) in THF (150 mL) at 0° C. was added n-BuLi (41 mL of 2.7M in hex). After 15 min, (+)-R-pulegone (16.25 mL, 0.100 mol) was added dropwise. After 30 min at 0° C., MeI (9 mL, 0.144 mol) was added. After 90 min at 0° C., the resultant mixture was stirred with H$_2$O and extracted with pet. ether (30–60). The combined organic layers were washed with sat. aq. NH$_4$Cl (3×) and evaporated to provide crude material, which was purified after distillation at aspirator pressure (~50 mmHg), bp (135°-145° C.). In this manner, 15.1 g (91%) of an oil was obtained, which was mostly 2-methylpulegone (78) with a small amount of 3,5-dimethyl-2(2-propenyl)cyclohexanone, as determined by NMR (90 MHz) and in agreement with that previously observed by Reusch et al.[6] This material was used without further purification.

Crude 2-methylpulegone (78, 13 mL, 90 mmol), H$_2$O (25 mL), and 38% HCl (25 mL) were heated in a distillation apparatus at 130° C.. Initially acetone was collected, and thereafter over 3 h the dimethylcyclohexanone azeotrope with water distilled at 105° C. The organic layer of the distillate was separated, dried over K$_2$CO$_3$, and distilled, by 172°-178° C., to provide 8.14 g (72%) of colorless oil, which was determined to be a mixture of desired trans:cis-dimethylcyclohexanones 81 and 80 in a ratio of 1.96:1, respectively, by 1H NMR (400 MHz). This oil was used without further purification.

NMR (400 MHz) of 81: δ 0.00 (d, 3H, J=6.5 Hz, 3-CH₃), 1.02 (d, 3H, J=6.1 Hz, 2-CH₃). IR (neat): 2970, 2940, 2880, 1720, 1455 cm⁻¹. EIMS: m/e (rel int) 126 (45), 55 (100). Exact mass Calcd. for $C_8H_{14}O$: 126.1045. Found: 126.1044.

A solution of (2S,3R)2,3-dimethylcyclohexanone 81 (7.95 g, 63.1 mmol) and p-toluenesulfonylhydrazide (12 g, 65 mmol) in THF (125 mL) was allowed to stir overnight. When the solvent was removed in vacuo, 18.5 g (100%) of N'-[(2S,3R)2,3-dimethylcyclohexylimino]-p-toluenesulfonylhydrazide (82) was obtained as a crude solid, which was spectrally characterized and used without further purification.

NMR (90 MHz): δ 0.70–2.85 (m, 17H), 7.10–7.52 (m, 2H, ArH), 7.55–7.95 (m, 2H, ArH). IR (melt): 3230 (broad), 2940, 2890, 1605, 1455, 1400, 1340, 1175, 1095, 1010, 930, 825 cm⁻¹. EIMS: m/e (rel int) 294 (7), 139 (100).

To a solution of N'-[(2S,3R)2,3-dimethylcyclohexylimino]-p-toluenesulfonyl hydrazide (82, 6.5 g, 22.1 mmol) in TMEDA (45 mL) at −78° C. was added n-BuLi (33 mL of 2.7M in hex). The resultant mixture was allowed to warm to ambient temperature. After 90 min, the mix was cooled to 0° C. and dry DMF (10 mL) was added. After 90 min the reaction contents were poured into stirring sat. aq. NH₄Cl and extracted with Et₂O (3×). The combined ethereal layers were washed with sat. aq. NH₄Cl (2×) and brine, dried over MgSO₄, and evaporated below ambient temperature to afford an oil, which was initially passed as an ethereal solution through $SiO_2$ and fractionally distilled at aspirator pressure (~50 mmHg). In this manner, 1.05 g of oil, by 135° C., was obtained and shown to be a 7:3 mix, respectively, of 6S:6R 5,6-dimethylcyclohexene carboxaldehydes 83 by NMR (400 MHz). This mixture was submitted to further transformation without additional purification.

NMR (400 MHz) of (5R,6S)5,6-dimethylcyclohexene carboxaldehyde: δ 0.89 (d, 3H, J=6.7 Hz, 3 —CH₃), 1.06 (d, 3H, J=6.9 Hz, 2 —CH₃), 1.15–1.90 (m, 4H), 2.15–2.63 (m, 2H), 6.73 (t, 1H, J=7.1 Hz, =CH), 9.37 (s, 1H, CHO). IR (neat): 2969, 2925, 2885, 1685, 1642, 1378 cm⁻¹.

To a solution of (5R,6S) 5,6-dimethylcyclohexene carboxaldehyde (83, 1.0 g, 7.25 mmol) in Et₂O at −78° C. was added a solution of tris(trimethylsilyl)aluminum-(III) etherate[1] (6 mL of 1.4M in pentane). After a few minutes, acetic anhydride (1.5 mL, 15.9 mmol) and DMAP (50 mg) were added and the reaction mixture allowed to warm to ambient temperature overnight. The resultant mix was poured into H₂O. The separated organic layer was washed with aq. sodium potassium tartrate (333), sat. aq. NH₄Cl, and sat. aq. NaCl, dried over Na₂SO₄, and evaporated to give an oil that was purified via flash-column chromatography with $SiO_2$. Elution with hexane provided 1.4 g (76%) of oil, which was a mixture of diastereomeric 5,6-dimethylcyclohexenyl(trimethylsilyl)methyl acetates 84, as confirmed by 1H NMR (400 MHz) and GLC analysis. This mixture was used without further purification.

NMR (400 MHz): δ 0.021, 0.028, 0.039, 0.043 (4s, 9H, SiCH₃), 2.01, 2.03, 2.04, 2.05 (4s, 3H, O2CCH₃). IR (neat): 1742 cm⁻¹. EIMS: m/e (rel int) 254 (2), 117 (100). Exact mass Calcd. for $C_{14}H_{26}SiO_2$: 254.1702. Found: 254.1703.

To a solution of diethylamine (5.4 mL) in THF (100 mL) at −78° C. was added n-BuLi (20 mL of 2.7M in hexane). After 45 min, a solution of a diastereomeric mixture of (5R)5,6-dimethylcyclo-hexenyl-(trimethylsilyl)methyl acetate (84, 5.88 g, 23.1 mmol) in THF (40 mL) was added dropwise via cannula. The reaction was allowed to warm to 22° C. over several hours. After 65 h, at ambient temperature, the reaction mix was stirred with sat. aq. NH₄Cl (150 mL) and 5N HCl (1 mL) and extracted with CHCl₃ (3×). The combined organic layers were washed with brine and evaporated to give an oil, which was purified via flash-column chromatography with $SiO_2$ to provide, after stepwise gradient elution with HOAc/EtOAc/hex, 1.66 g (28%) of (2'E,Z,1'S,3'S,4'R)3',4'-dimethyl- 2'(trimethylsilylmethylene)cycloh exylacetic acids 85 as an oil. This material was used without further purification.

NMR (400 MHz): δ 0.062 (s, 9H, SiCH₃), 0.88 (d, 1.5H, J=6.8 Hz, CH₃), 0.91 (d, 1.5H, J,=7.2 Hz, CH₃), 0.95 (d, 1.5 H, J,=7.4 Hz), 1.14 (d, 1.5H, J=7.5 Hz, CH₃), 1.22–1.46 (m, 2H), 1.52–1.92 (m, 3H), 2.32–2.64 (m, 4H), 5.22–5.25 (m, 0.5H, =CH), 5.32 (s, 0.54, =CH).

Through a solution of vinylsilane acid 85 (675 mg, 2.66 mmol) in CH₂Cl₂ (30 mL) at −78° C. was passed O₃/O₂ for 10 min, whereupon a blue color persisted. The reaction was purged with argon, and the resultant decolorized mixture was diluted with acetone (5 mL) and treated with TFA (0.6 mL) The reaction was allowed to warm to 22° C. After 20 h, the mixture was partitioned between EtOAc and H₂O. The separate aqueous layer was extracted with more EtOAc (2×). The combined organic layers were evaporated to give a material that was purified via thin-layer chromatography with $SiO_2$. After two developments with EtOAc/hex, the title trioxane 30 was isolated as a colorless oil, 160 mg (22%), which proved to be a hydrate ($C_{14}H_{22}O_5 \cdot 1/4$ H₂O) by analysis. $[\alpha]_D^{22} = -52.8$ (c=0.58, CHCl₃).

NMR (400 MHz): 0.89 (d, 3H, J=7.2 Hz, CH₃), 1.05 (d, 3H, J=8.0 Hz, CH₃), 1.30–1.48 (bm, 3H), 1.57 (bs, 3H, 3-CH₃) 1.62 (bs, 3H, 3-CH₃), 1.63–1.84 (m, 2H), 1.97–2.09 (bm, 1H), 2.58 (quintet, 1H, J=9.4 Hz), 2.80–2.95 (m, 1H), 5.50 (s, 1H, H₄s). IR (CHCl₃): 2945, 1758, 1388, 1188, 1060 cm⁻¹. EIMS: m/e (rel int) 238 (M+ −O₂, 1), 180 (M+ −acetone, −O₂, 33), 83 (85), 69 (60), 55 (83), 43 (100). CIMS (NH₄³⁰): m/e (rel int) 288 (M+NH₄⁺, 22), 271 (M+H⁺, 6), 167 (100). Anal Calcd. for $C_{14}H_{22}O_5 \cdot 1/4H_2O$: C, 61.18; H, 8.07. Found: C, 61.31; H, 7.98.

EXAMPLE 54

(2'E,Z,1R,1'S,3'S,4'R)-2-[3,',4'-Dimethyl-2'-(trimethylsilylmethylene)cyclohexyl] propionic Acid (86)

To a solution of diisopropylamine (0.90 mL, 6.4 mmol) in THF (20 mL) at −78° C. was added n-BuLi (2.4 mL of 2.7M in hexane). The solution was allowed to warm to 0° C. and, after 15 min at 0° C., recooled to −78° C., whereupon a solution of (2'EZ,1'S,3'S,4'R)3'-4''-dimethyl-2-(trimethyl-silylmethylene)cyclohexenylacetic acid (85, 743 mg, 2.92 mmol) in THF (7 mL) was added. The reaction was allowed to warm to ambient temperature and then heated at 50° C. for 2 h, before cooling to −78° C. and subsequent treatment with methyl iodide (0.54 mL, 8.5 mmol). The mixture was allowed to warm to ambient temperature and after 90 min was poured into sat. aq. NH₄Cl (250 mL) and 5N HCl (5 mL) and extracted with CHCl₃ (3×75 mL). The combined organic layers were dried over MgSO₄ and evaporated to give a crude product, which was purified via flash-column chromatography with $SiO_2$. Elution with EtOAc/hexane provided 760 mg (97%) of the title diastereomers 86 as a pale yellow oil.

NMR (400 MHz): δ 0.084, 0.088 (2s, 9H, $SiCH_3$), 0.85–0.97 (m, 5H), 1.01–1.21 (m, 6H), 1.22–1.33 (m, 1H), 1.35–1.47 (m, 1H), 1.48–1.95 (m, 4H), 2.25–2.43 (m, 1.5H), 2.57 (ddd, 0.5H, J=5.0, 7.1 7.2 Hz), 2.74 (ddd, 0.5H, J=7.0, 12.9, 13.4 Hz), 2.80 (ddd, 0.5H, J=7.0, 12.9, 13.4 Hz), 5.20 (s, 0.5H, =CH), 5.29 (s, 0.54, =CH).IR (neat): 3600–2250, 1713, 1610, 1470, 1255, 1225, 900, 850 $cm^{-1}$. EIMS: m/e (rel int) 268 (2) 75 (57), 73 (100). Exact mass Calcd. for $C_{15}H_{28}SiO_2$: 268.1859. Found: 268.1860.

EXAMPLE 55

(+)-Hexahydro-3,3,7,10α,11β-pentamethyl-4aH,6H-1,2,4-trioxino-[6.5-j][2] benzopyran-6-one (31)

Through a solution of vinylsilane acid (86, 700 mg 2.61 mmol) in $CH_2Cl_2$, (30 ML) at −78° C. was passed $O_3/O_2$ until a blue-gray coloration appeared. The color disappeared upon purging with argon, and acetone (15 mL) and TFA (2 mL) were added. The reaction was allowed to warm to ambient temperature over 40 min and, after 22 h, was stirred with sat. aq. $NaHCO_3$ and extracted with hexane (3×50 mL). The combined organic layers were washed with sat. aq. $NaHCO_3$, dried over $MgSO_4$, and evaporated to a crude material, which was purified via successive (2×) thin-layer chromatography with $SiO_2$. After development in EtOAc/hexane, the resultant colorless oil slowly crystallized from cold pentane to afford 45 mg (6%) of 31 as white crystals, mp 67°–69° C.. $[\alpha]_D^{22} = +18.12$ (c=0.275, $CHCl_3$).

NMR (400 MHz, DMSO-d6, 90° C.): δ 0.92 (d, 3H, J=7.2 Hz, $CH_3$), 1.05 (d, 3H, J=7.2 Hz, $CH_3$), 1.10 (d, 3H, J=7.2 Hz, $CH_3$), 1.40 (s, 3H, 3-$CH_3$), 1.47 (s, 3H, 3-$CH_3$), 1.52–1.75 (m, 3H), 1.82–2.05 (m, 4H), 3.48 (m, 1H, H7a), 5.74 (s, 1H, H4α). IR ($CHCl_3$): 2960, 2940, 1740, 1385, 1175 $cm^{-1}$. CIMS ($NH_4^+$): m/e (rel int) 302 ($M+NH_4^+$,5), 285 ($M+H^+$, 6), 209 (58), 191 (60), 181 (100). Anal. Calcd. for $C_{15}H_{24}O_5$: C, 63.36; H, 8.51. Found: C, 63.61; H, 8.59.

EXAMPLE 56

3R-Methyl-2R-[2′-(2″,5″,5″-trimethyldioxanyl)ethyl]-1E/Z-tri-methylsilyl methylenecyclohexane (89)

To a dry 500 mL 3-necked round-bottom flask equipped with Ar inlet, stopper, septum, and magnetic stirrer was added pentane (200 mL) and methoxydimethylsilyltrimethylsilylmethane (10 mL or 47 mmol). The mixture was cooled to 0° C. and a pentane solution of t-butyl lithium was added (28 mL of 1.7M or 47 mmol) over a 5 min period. The mixture was warmed to 22° C. and stirred 2 h. The resultant yellow solution was cooled to −78° C. and a solution of ketone 6 (11.4 g or 42.5 mmol) in pentane (100 mL), was added via cannula over 10 min. The reaction mixture was allowed to warm slowly to 22° C. and left overnight. The reaction mixture was poured into sat. aq. $NH_4Cl$ (500 mL) and then washed with additional sat. aq. $NH_4Cl$ (2×500 mL). The pentane was then washed with sat. aq. NaCl (500 mL), dried over $MgSO_4$, filtered, and the solvent evaporated to afford 17.6 g of yellow oil. Gradient elution flash chromatography on silica gel (150 g) was carried out with 5→20% EtOAc/hexane. Polar material eluted from the column weighed 1.57 g and appeared to be a tertiary alcohol adduct of t-BuLi with 6. The starting ketone was recovered to provide 6.38 g of 6. The desired olefin 89 (5.23 g or 36.4% yield) was isolated as a light yellow oil. Based on recovered recyclable starting material, the yield of 89 was 83%. 1H NMR (400 MHz, $CDCl_3$) indicates a 3:1 ratio of isomers: δ 0.096 and 0.0128 (2s, 9H), 0.90 and 0.93 (2d, 3H, J=6.5 Hz), 0.93 and 0.95 (2s, 3H), 0.96 and 0.98 (2s, 3H), 1.36 and 1.39 (2s, 3H), 3.49 (m, 4H), 5.11 and 5.12 (2s, 1H). IR: 2950, 2860, 1610, 1450, 1370, 1250, 1210, 1190, 1090, 1050, 1020, 865, 840, and 690 $cm^{-1}$. EIMS: (m/e) 338 (M+), 323 (M-Me), 234, 194, 179, 162, 141, 129, 107. Exact mass. Calcd for $C_{20}H_{38}SiO_2$: 338.2641. Found 338.2634. Anal. Calcd for $C_{20}H_{38}SiO_2$: C, 70.94; H, 11.31. Found: C, 70.87; H, 11.33.

EXAMPLE 57

(+)-3R-Methyl-2R-(3′-oxobutyl-1Z-trimethylsilylmethylenecyclohexane (90)

To a well-stirred solution of the ketal 89 (4.5 g or 13.31 mmol) in $CH_2Cl_2$ (175 mL) at 22° C. under Ar was added 230–400 mesh silica gel (24 g) followed by 10% aq. oxalic acid (5 mL). The mixture was vigorously stirred until the oxalic acid/$H_2O$ was absorbed onto the support, and then allowed to stir for 18 h. The mixture was filtered and the silica gel washed with EtOAc (300 mL). The combined organic layers were washed with sat. aq. $NaHCO_3$ (3×100 mL), dried over $MgSO_4$, filtered, and the solvent evaporated to give 3.67 g of yellow oil. Gradient elution flash chromatography on silica gel (175 g) with hexane (1L), 1% EtOAc/hexane (1L), 2% EtOAc/hexane (1L), and 3% EtOAc/hexane (1L) collecting 25×50 mL fractions gave in fractions 4–8: 1.53 g of isomerically pure 90. $[\alpha]_D^{21} = +15.7$ (c=1.65, $CHCl_3$). 1H NMR (400 MHz, $CDCl_3$): δ 0.098 (s, 9H), 0.91 (m, 2H), 0.93 (d, J=7.0 Hz, 3H), 1.27 (m, 2H), 1.52 (m, 1H), 1.6–1.9 (m, 3H), 2.12 (s, 3H), 2.04–2.22 (m, 2H), 2.35 (m, 2H), 5.06 (s, 1H). IR: 2950, 2920, 2860, 1720, 1610, 1450, 1400, 1360, 1250, 1165, 1050, 870, 840, and 690 $cm^{-1}$. DCIMS-$NH_3$ (m/e): 253 (M+H), 235, 219, 194, 181, 163, 143. DCIMS-$NH_3$ exact mass. Calcd for $C_{15}H_{29}SiO$ (M+H): 253.1988. Found: 253.1976. Anal. Calcd for $C_{15}H_{28}SiO$: C, 71.36; H, 11.18. Found: C, 71.08; H, 11.31. Fractions #9–15 were an E/Z mixture predominating in 90 (Z), and weighed 1.08 g. The total product was 2.61 g or 78% yield.

EXAMPLE 58

(+)-3a,6a-Dimethyl-3β-methoxyoctahydrobenzo-1,2-dioxepin-9aβ-carboxaldehyde (92)

Through a −78° C. solution of the vinylsilane 90 (E/Z mixture from above) (0.78 g or 3.1 mmol) in methanol (25 mL) was bubbled ozonized oxygen (0.5 L/min, 7.5 p.s.i., 70 V) until a faint blue-grey color persisted (about 18 min). The solution was purged with a stream of argon and when the color of excess ozone was gone, the mixture was treated with boron trifluoride etherate complex (200 μL) and warmed to 22° C. After 90 min at 22° C. under Ar, the reaction mixture was poured into sat. aq. $NaHCO_3$ (250 mL). The mixture was extracted with EtOAc (3×75 mL), dried over $MgSO_4$, filtered, and the solvent evaporated to give 658 mg of a colorless glass. Flash chromatography on silica gel (20 g) with 7% EtOAc/hexane gave 92 (440 mg or 59% yield) as a colorless oil which slowly solidified and was recrystallized from cold hexane, m.p. 100°–102° C. $[\alpha]_D^{23} = +317$ (c=1.18, $CDCl_3$).

NOESY, DQCOSY, HETCOR, APT, single frequency decoupling, and Eu(fod)3 NMR experiments were performed in order to make assignments to the 1H NMR (400 MHz, CDCl$_3$): δ 0.90 (m, 1H, H9a), 0.94 (d, 3H, J=6.4 Hz, 8a-Me), 1.19 (d, 3H, J=1.2 Hz, 4β-Me), 1.25 (m, 2H, H10β/7a), 1.32 (dddd, 1H, J=3.8, 12.1, 14.0, 14.0 Hz, H11a), 1.52 (dddd, 1H, J=1.3, 11.8, 11.8, 14.5 Hz, H6β), 1.68 (m, 2H, H9β/11β), 1.85 (dddd, 1H, J=1.2, 3.0, 7.8, 14.6 Hz, H5β), 1.93 (br d, 1H, J=11.4 Hz, H10α), 1.97 (br d, 1H, J=11.4 Hz, H6a), 2.08 (ddd, J=1.3, 7.8, 14.6 Hz, H5a), 2.18 (dddq, 1H, J=4.0, 6.4, 11.4, 11.4 Hz, H8β), 3.34 (s, 3H, 4a-OMe), 9.51 (d, 1H, J=2.8 Hz, long range W-coupling to 7a). IR: 2940, 2865, 2720, 2700, 1740, 1450, 1375, 1270, 1250, 1210, 1190, 1165, 1110, 1085, 1065, 1000, 900, 880, 835, 770, and 740 cm$^{-1}$. Anal. Calcd for C$_{13}$H$_{22}$O$_4$: C, 64.44; H, 9.14. Found: C, 64.28; H, 9.34. DCIMS-NH$_3$: (m/e) weak 260 (M+NH$_4$), strong 228 (260-CH$_3$OH), 220, 211 (M-O$_2$+H), 206, 195, 189, 183, 171, 165.

EXAMPLE 59

(+)-12-Acetoxy-4,8-dimethyl-2,3,13-trioxatricyclo[5.4.2.1,4 0.1,7]tridecane (93)

Through a −78° C. solution of the silane 90 (175 mg or 0.69 mmol) in MeOH (8 mL) was bubbled ozonized oxygen (0.5 L/min, 7.5 p.s.i., 70 V) until a faint bluegrey color occurred. The solution was purged with Ar and rotary evaporated (bath temp. <20° C.). Hexane was added (10 mL) and then rotary evaporated, the process repeated, and the product was placed under high vacuum (30 min, 0.05 mm Hg) to provide the dioxetane 5R-(3-oxobutyl)-6R-methyl-3RS-trimethylsilyloxy-1,2-dioxa-4S-spiro[5.3]nonane (91). 1H NMR (400 MHz, CDCl$_3$): δ 0.20 (s, 9H), 1.00 (d, 3H, J=6.4 Hz), 2.17 (s, 3H), 6.08 (s, 1H). IR (film): 2960, 2940, 2880, 1720, 1450, 1410, 1380, 1360, 1260, 1170, 1080, 1000, 960, 880–850 (br), and 760 cm$^{-1}$.

The product 91 was dissolved in CH$_2$Cl$_2$ (2 mL) under Ar, and acetic anhydride (2 mL) and Amberlyst TM 15 (200 mg) were added. After 100 min heptane was added (75 mL), and the mixture was filtered. The solvent was evaporated and the crude product placed on a PTLC plate (1.5 mm SiO$_2$). Elution with benzene afforded pure 93 (56 mg or 30% yield) as a colorless oil. [α]$_D^{21}$ = +9.3 (c=1.5, hexane). 1H NMR (400 MHz, CDCl$_3$): δ 6.44 (s, 1H, H12β), 2.39 (ddd, 1H, J=4.0, 13.2, 14.5 Hz, H5a), 2.20 (s, 3H), 2.14 (m, 1H, H11β), 2.02 (ddd, 1H, J=3.0, 4.8, 14.5, H5β), 1.91 (dddd, 1H, J=1.2, 3.5, 6.6, 16.7 Hz, H6a), 1.62 (m, 2H, H9β/10a), 1.48 (m, 2H, H6β/8β), 1.39 (s, 3H, 4-Me), 1.39 (m, 1H, H7a), 1.25 (m, 2H, H11a/10β), 0.98 (m, 1H, H9a), 0.97 (d, J=6.3 Hz, 8-Me). 13C NMR (CDCl$_3$): 170.4 (—OAc), 104.5 (C4), 88.3 (C12), 83.1 (C1), 51.6 (C7), 37.6 (—OAc), 36.1 (C5), 34.6 (C11), 33.9 (C6), 25.9 (Me), 24.9 (C10), 22.1 (C9), 21.4 (C8), 20.1 (Me). IR: 2940, 2880, 1750, 1450, 1360, 1240, 1230, 1210, 1165, 1140, 1100, 1070, 1010, 970, 880, 840 cm$^{-1}$. DCIMS (NH$_3$): m/e 288 (M+NH$_4$), 271 (M+H), 228, 211 (M-OAc), 195, 183, 169, 151, 139. HRDCIMS (NH$_3$). Calcd for C$_{14}$H$_{22}$O$_5$: 271.1545. Found: 271.1549. Anal. Calcd for C$_{14}$H$_{22}$O$_5$: C, 62.20; H, 8.20. Found C, 62.53; H, 8.25.

EXAMPLE 60

4,8-Dimethyl-(+)-12-propionyloxy-2,3,13-trioxatricyclo[5.4.2 ,0] tridecane (8a,9-secoartemisinin, 94)

To a solution of the aldehyde 92 (250 mg or 1.03 mmol) in CH$_2$Cl$_2$ (2 mL) under Ar at 22° C. was added propionic anhydride (6 mL) and Amberlyst TM 15 (300 mg). The mixture was stirred overnight, filtered, and poured into 1% aq. NaOH (100 mL). The mixture was extracted with ether (3×50 mL) and the combined organic layers were washed with 1% aq. NaOH (2×50 mL). The organic layer was dried over MgSO$_4$, filtered, and the solvent evaporated to afford crude 94 (186 mg). PTLC on two 1.5 mm thickness SiO$_2$ plates with 7% ether/pentane gave pure 94 (63 mg or 22% yield) as a colorless oil. [α]$_D^{22}$ = +26.3 (c=1.90, hexane). 1H NMR (400 MHz, CDCl$_3$): δ 0.96 (m, 1H), 0.98 (d, 3H, J=6.2 Hz), 1.20 (t, 3H, J=7.5 Hz), 1.2–1.6 (m, 7H), 1.38 (s, 3H), 1.90 (dddd, 1H, J=1.1, 3.0, 7.0, 16.8 Hz), 2.02 (ddd, 1H, J=3.0, 4.9, 14.6 Hz), 2.14 (m, 1H), 2.39 (ddd, 1H, J=4.0, 13.4, 14.6 Hz), 2.46 (q, 1H, J=7.5 Hz), 6.45 (s, 1H). IR: 2940, 2880, 1745, 1450, 1380, 1355, 1270, 1210, 1190, 1130, 1110, 1080, 1035, 990, 970, 910, 880, 840, and 810 cm$^{-1}$. DCIMS-NH$_3$: (m/e) 302 (M+NH$_4$), weak 285 (M+H), 260, strong 228, 211, 195, 183, 165, 147. Anal. Calcd for C$_{15}$H$_{24}$O$_5$: C, 63.36; H, 8.51. Found: C, 63.85; H, 8.48.

EXAMPLE 61

4,8-Dimethyl-12-methoxy-2,3,13-trioxatricyclo[5.4.2.0] tridecane (97)

To a solution of the aldehyde 92 (129 mg) in benzene (5 mL) and methanol (2 mL) under Ar at 22° C. was added triethylorthoacetate (1 mL) and BF$_3$.OEt$_2$ (100 μL). The orange-red mixture was stirred 18 h, poured into sat. aq. NaHCO$_3$ (50 mL), and extracted with EtOAc (100 mL) The organic layer was washed with sat. aq. NaHCO$_3$ (2×100 mL), dried over MgSO$_4$, filtered, and the solvent evaporated to give a yellow oil. PTLC (two 1.5 mm thickness SiO$_2$ plates) with benzene gave recovered 92 (43 mg) and tricyclic 97 (31 mg or 38% yield, based on recovered starting material) as a 3:1 mixture of isomers (12a:12β) as seen in the 1H NMR (400 MHz, CDCl$_3$): δ 0.92 (d, J=6.4 Hz, minor isomer), and 0.97 (d, J=6.08 Hz, major isomer of 3H), 1.40 (s, 3H), 1.89 (m, 1H), 2.0 (m, 1H), 2.39 (m, 2H), 3.51 (s, 3H), 4.91 (s, minor isomer), 4.95 (s, major isomer of 1H). IR: 2930, 2880, 1450, 1380, 1350, 1100, 1020, 880, 840 cm$^{-1}$. DCIMS-NH$_3$: (m/e) 228 (M-O$_2$+NH$_4$), 211 (M-O$_2$+H), 195, 183, 177, 165, 151.

EXAMPLE 62

4,8-Dimethyl-12-hydroxy-2,3,13-trioxatricyclo[5.4.2.0]-tridecane (95)

To the dioxetane 91, freshly prepared as described above for 93 (derived from 1.18 g of 90), was added THF (45 mL) and 1M aq. HCl (5 mL). The mixture was stirred under Ar for 75 min and poured into sat. aq. NaHCO$_3$ (400 mL). The mixture was extracted with EtOAc (3×100 mL). The combined organic layers were washed with sat. aq. NaHCO$_3$ (100 mL), dried over MgSO$_4$, filtered, and the solvent evaporated to give 0.94 g of a colorless oil. Flash chromatography on silica gel (30 g) with 20% EtOAc/hexane gave 95 (528 mg or 50% yield) as a colorless oil that was a complex mixture. The ratio from the NMR of 95:95a:95b was 1:2:1, respectively. 1H NMR (400 MHz, CDCl$_3$): δ 0.93 (d, J=6.6 Hz, Me), 1.28 (s, Me), 1.42 (s, Me), 2.14 (s, Me), 3.38 (d, J=13.0 Hz), 5.28 (d, J=13 Hz), 9.48 (d, J=2.8 Hz), 9.50 (d, J=2.7 Hz). IR (film): 3400, 2940, 2860, 2700, 1740, 1710, 1450, 1380, 1210, 1170, 1080, 1020, 955, 880, 840 cm$^{-1}$. DCIMS-NH$_3$ (m/e): 246

EXAMPLE 63

(−)-12-Benzyloxycarbonyloxy-4,8-dimethyl-2,3,13-trioxatricyclo [5.4.2.0]tridecane (96)

To a solution of the alcohol 95 (200 mg or 0.88 mmol) in $CH_2Cl_2$ (5 mL) at 22° C. under Ar was added benzylchloroformate (150 μL or 1.0 mmol) followed by 4-(N,N-dimethylamino)pyridine (150 mg or 1.2 mmol). The solution turned yellow and gave off gas ($CO_2$). After 1 h, the reaction mixture was poured into sat. aq. $NH_4Cl$ (100 mL) and extracted with EtOAc (3×50 mL). The combined organic layers were washed with sat. aq. $NH_4Cl$ (2×50 mL), sat. aq. NaCl (50 mL), dried over $MgSo_4$, filtered, and evaporated to give a yellow oil. PTLC on two 1.5 mm thickness $SiO_2$ plates with 20% EtOAc/hexane gave the product 96 as a colorless oil (69 mg or 22% yield) which contained a minor isomeric contaminant (9:1 ratio by NMR) that was removed by trituration from hexane followed by recrystallization from hexane/$CH_2Cl_2$, m.p. 110° C. $[\alpha]_D^{22} = -17.5°$ (c=0.37, $CDCl_3$). 1H NMR (400 MHz, $CDCl_3$): δ 0.98 (d, 3H, J=6.2 Hz), 1.0 (m, 1H), 1.2–1.7 (m, 7H), 1.40 (s, 3H), 1.91 (dddd, 1H, J=1.0, 3.3, 6.2, 16.3 Hz), 2.03 (ddd, 1H, J=3.1, 4.9, 14.8 Hz), 2.20 (m, 1H), 2.40 (ddd, 1H, J=4.0, 13.2, 14.8 Hz), 5.24 (s, 2H), 6.31 (s, 1H), 7.38 (m, 5H). IR ($CHCl_3$): 3000, 2940, 2880, 1745, 1455, 1385, 1270, 1225, 1175, 1140, 1100, 1070, 1055, 1035, 955, 940 910, 880, 840 cm$^{-1}$. DCIMS-$NH_3$: (m/e) 380 (M+$NH_4$), 363 (M+H), 303, 228, 211, 195, 183, 165, 151. Anal. Calcd for $C_{20}H_{26}O_6$: C, 66.28; H, 7.23. Found: C, 66.41; H, 7.14.

EXAMPLE 64

4R,8R-Dimethyl-1S-hydroxymethyl-4β-methoxy 2,3-dioxabicyclo-[5.4.0]undecane (117)

To a solution of the aldehyde 92 (352 mg or 1.45 mmol) in MeOH (35 mL) under Ar at 0° C. was added solid $NaBH_4$ (350 mg or 9.2 mmol). After about 5 min (the reaction was done by TLC) the mixture was poured into sat. aq. $NH_4Cl$ (200 mL) and extracted with $Et_2O$ (3×50 mL). The combined organic layers were washed with sat. aq. $NH_4Cl$ (2×75 mL), brine (50 mL), dried over $MgSO_4$, filtered, and the solvent was evaporated to afford the alcohol 117 as a colorless oil (335 mg or 95% yield) which was sufficiently pure for direct use.

EXAMPLE 65

(+)-4,8-Dimethyl-2,3,13-trioxatricyclo[5.4.2.0]-tridecane (118)

The crude alcohol 117 (305 mg or 1.25 mmol) was dissolved in $CH_2Cl_2$ (25 mL) and treated with pTsOH.-$H_2O$ (30 mg). After brief warming to dissolve the acid, the mixture was stirred at 21° C. for 30 min and poured into sat. aq. $NaHCO_3$. The mixture was extracted with $Et_2O$ (2×50 mL). The ether layers were washed with $NaHCO_3$ (2×50 mL) dried over $MgSO_4$, filtered, and the solvent evaporated to give crude 118 which was purified by flash chromatography on $SiO_2$ (4 cm diam × 6") with 5% EtOAc/hexane to give 118 (246 mg or 79% yield) as an oil which solidified on standing and could be recrystallized from cold pentane, m.p. 69°-71° C. $[\alpha]_D^{22} = +88.8°$ (c=1.02, $CDCl_3$). 1H NMR (400 MHz, $CDCl_3$): δ 0.98 (d, 3H, J=6.1 Hz), 1.33 (s, 3H), 1.80 (m, 1H), 1.88 (ddd, 1H, J=3.3, 6.1, 16.7 Hz), 2.00 (ddd, 1H, J=3.3, 4.9, 14.6 Hz), 2.42 (ddd, 1H, J=3.8, 13.4, 14.6 Hz), 4.03 (dd, 1H, J=1.5, 11.0 Hz), 4.19 (d, 1H, J=11.0 Hz). IR: 2910, 2870, 1450, 1370, 1210, 1170, 1150, 1070, 1040, 900, 870, 840 cm$^{-1}$. DCIMS-$NH_3$: (m/e) 230 (M+$NH_4$), 213 (M+H), 200, 195, 183.

EXAMPLE 66

2-t-Butylperoxy-2-ethylbutanol (88)

To a solution of m-chloroperbenzoic acid (1.8 g of 80%, 10.5 mmol) in dry $CH_2Cl_2$ (35 mL) at 0° C., was added 2-ethylbutene (1.0 mL, 8.2 mmol). After 1 h at 0° C., the solid was filtered off and washed with pentane. To the filtrate was added a solution of t-butyl hydroperoxide (11 mL of 3M in isopentane). The solution was cooled to 0° C. and p-toluenesulfonic acid (50 mg) was added. After 90 min, the reaction contents were poured into cold 10% aq. KOH and extracted with $Et_2O$ (100 mL). The ethereal layer was washed with $H_2O$ (2×100 mL), dried over $MgSO_4$, and evaporated below room temperature behind an explosion shield to give 2-(t-butylperoxy)-2-ethylbutanol (88) as a colorless oil, 1.6 g, (80%), which was not stored but was used immediately without further purification.

NMR (90 MHz): δ 0.70–0.93 (m, 6H, $CH_3$), 1.21, 1.22 (2s, 9H, ($CH_3$)3C), 1.33–1.75 (m, 4H, $CH_2$), 3.56 (bm, 2H, $\underline{CH_2}$OH).

EXAMPLE 67

2-t-Butylperoxy-2-ethylbutyl proprionate (32)

To a solution of crude peroxide alcohol 88 (800 mg, 4.2 mmol) and pyridine (0.5 mL) in $CH_2Cl_2$ (15 mL) was added proprionic anhydride (0.58 mL, 4.5 mmol). After 10 min, DMAP (12 mg) was added. After 21 h, the reaction was poured into 5% aq. NaOH (100 mL) and extracted with hexane (100 mL). The separated hexane layer was washed with 5% aq. NaOH (100 mL) and sat. aq. $NH_4Cl$ (3×50 mL), dried over $MgSO_4$, and evaporated below room temperature behind an explosion shield to give a crude oil, which was purified via flash-column chromatography with $SiO_2$. After gradient elution with EtOAc/hexane, 2-t-butylperoxy-2-ethylbutyl proprionate (32) was obtained as a colorless oil, 594 mg (57%).

$^1$H NMR (400 MHz): δ 0.87 (t, 6H, J=7.6 Hz, $CH_3$), 1.15 (t, 3H, J=8.0 Hz, $O_2CCH_2\underline{CH_3}$), 1.20 (s, 9H, ($CH_3$)3C), 1.49 (dd, 2H, J=7.4, 14 Hz, $CH_2$), 1.53–1.71 (m, 2H, $CH_2$), 2.34 (q, 2H, J=7.6 Hz, $02C\underline{CH_2}$), 4.14 (s, 2H, $CH_2O_2C$). 13C NMR: d 7.3 (2), 9.2, 23.8 (2), 26.5 (3), 27.7, 64.6, 78.5, 82.7, 174.3. IR (neat): 2990, 1747, 1200 cm$^{-1}$. Anal Calcd. for $C_{13}H_{26}O_4$: C, 63.38; H, 10.64. Found: C, 63.15; H, 10.43.

EXAMPLE 68

2-t-Butylperoxy-2-ethylbutyl Butyrate (33)

To a solution of crude 2-t-butylperoxy-2-ethylbutanol 88 (800 mg, 4.2 mmol) and pyridine (0.5 mL) in $CH_2Cl_2$, (15 mL) was added butyric anhydride (0.73 mL, 4.5 mmol). After 10 min, DMAP (12 mg) was added. After 21 h, the reaction was poured into 5% aq. NaOH (100 mL) and extracted with hexane. The separated hexane layer was washed with 5% aq. NaOH (100 mL) and sat. aq. $NH_4Cl$ (3×50 mL), dried over $MgSO_4$, and evaporated below room temperature to afford a crude product, which was purified via flash-column chromatography with $SiO_2$. After gradient elution with EtOAc/hexane, 2-t-butylperoxy-2-ethylbutyl butyrate (33) was isolated as a colorless oil, 440 mg (40%).

$^1$H NMR (400 MHz): δ 0.87 (t, 6H, J=7.6 Hz, CH$_3$), 0.96 (t, 3H, J=7.2 Hz, O$_2$CCH$_2$C$\underline{H}_3$), 1.20 (s, 9H, C(CH$_3$)$_3$), 1.46-1.73 (m, 8H) 2.31 (t, 2H, J=7.6 Hz, O$_2$CCH$_2$), 4.14 (s, 2H, CO$_2$C H$_2$). 13C NMR: d 7.3 (2), 13.7, 18.5, 23.8 (2), 26.5 (3), 36.4, 64.5, 78.5, 82.7, 173.6. IR (neat): 2980, 2940, 1743, 1462, 1365, 1205, 1185 cm$^{-1}$. Anal. Calcd. for C$_{14}$H$_{28}$O$_4$1/10 C$_6$H$_{14}$: C, 65.24; H, 11.02. Found: C, 65.18; H, 11.06.

What is claimed is:

1. A compound of the formula

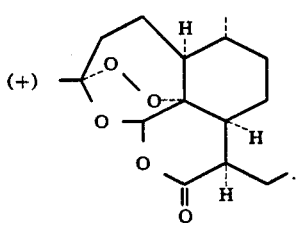

(+)

2. A compound of the formula

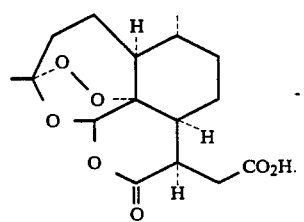

3. A compound of the formula

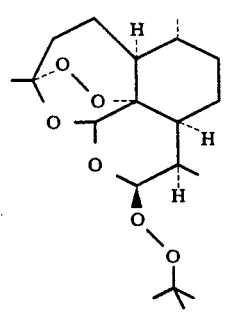

4. A compound of the formula

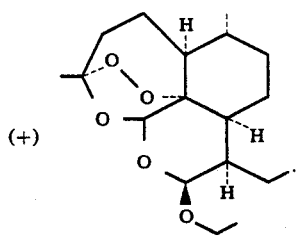

(+)

5. A compound of the formula

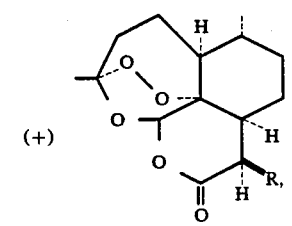

(+)

where R is a 2 to 20 carbon linear or branched alkyl or a 7 to 12 carbon hydrocarbyl aralkyl.

6. The compound of claim 5 wherein R is n-propyl.
7. The compound of claim 5 wherein R is n-hexyl.
8. The compound of claim 5 wherein R is isopropyl.
9. The compound of claim 5 wherein R is —CH$_2$—CH$_2$—CH$_2$—C$_6$H$_5$.
10. The compound of claim 5 wherein R is isoamyl.
11. The compound of claim 5 wherein R is —CH$_2$—C$_6$H$_5$.
12. A compound of the formula

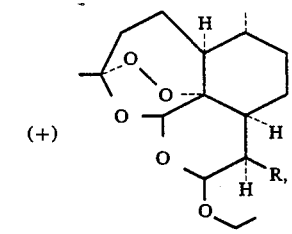

(+)

wherein R is 1 to 20 carbon linear or branched alkyl or a 7 to 12 carbon hydrocarbyl aralkyl.

13. The compound of claim 12 wherein R is n-propyl.

* * * * *